United States Patent
Qiu et al.

(10) Patent No.: US 8,872,422 B2
(45) Date of Patent: Oct. 28, 2014

(54) DINAPHTHYL ETHYLENE DERIVATIVCE, PROCESS FOR PREPARING IT, FILM PREPARED FROM IT, AND OLED INCLUDING THE FILM

(75) Inventors: Yong Qiu, Beijing (CN); Han Chen, Beijing (CN); Yinkui Li, Beijing (CN)

(73) Assignees: Tsinghua University, Beijing (CN); Beijing Visionox Technology Co., Ltd., Beijing (CN)

( * ) Notice: Subject to any disclaimer, the term of this patent is extended or adjusted under 35 U.S.C. 154(b) by 806 days.

(21) Appl. No.: 12/011,897

(22) Filed: Jan. 30, 2008

(65) Prior Publication Data

US 2008/0220286 A1    Sep. 11, 2008

(30) Foreign Application Priority Data

Jan. 31, 2007  (CN) .......................... 2007 1 0063411

(51) Int. Cl.
*C09K 11/06* (2006.01)
*H01L 51/54* (2006.01)
(Continued)

(52) U.S. Cl.
CPC ............ *C07D 333/08* (2013.01); *C07D 333/24* (2013.01); *C07C 15/58* (2013.01); *C07C 13/567* (2013.01); *C07D 309/34* (2013.01); *C07C 255/09* (2013.01); *C07C 211/54* (2013.01); *C07C 45/46* (2013.01); *C07C 15/62* (2013.01); *C07C 45/68* (2013.01); *C07D 233/96* (2013.01); *C07D 413/14* (2013.01); *C07D 219/06* (2013.01); *C07C 15/38* (2013.01); *C07D 209/08* (2013.01); *C07C 15/60* (2013.01); *C07D 403/10* (2013.01); *C07D 209/44* (2013.01); *C07D 213/68* (2013.01); *C07C 251/86* (2013.01); *C07D 209/86* (2013.01); *C07D 207/323* (2013.01); *C07C 2101/10* (2013.01); *C07C 2103/26* (2013.01); *C07C 211/58* (2013.01); *C07C 2103/24* (2013.01); *C07C 43/285* (2013.01); *C07D 213/74* (2013.01); *H01L 51/0052* (2013.01); *C07C 2102/08* (2013.01); *H01L 51/5012* (2013.01); *C07C 2103/50* (2013.01); *C07C 17/10* (2013.01); *C07D 251/24* (2013.01); *C07D 309/32* (2013.01); *C07C 245/10* (2013.01); *C07C 2103/97* (2013.01); *C07C 17/16* (2013.01); *C07D 271/107* (2013.01); *C07C 25/22* (2013.01); *C07D 215/06* (2013.01); *C07D 277/66* (2013.01); *C07D 307/54* (2013.01); *C07D 471/22* (2013.01); *C07D 221/14* (2013.01); *C07C 22/08* (2013.01); *C07C 17/2635* (2013.01); *C07C 43/225* (2013.01); *C07D 307/91* (2013.01); *C07C 13/465* (2013.01); *C07D 401/04* (2013.01); *C07C 2103/90* (2013.01); *C07C 13/72* (2013.01); *C07C 45/292* (2013.01); *C07C 255/52* (2013.01); *C07D 471/06* (2013.01); *C07D 235/20* (2013.01); *C07C 45/00* (2013.01); *C07D 307/66* (2013.01); *C07C 2103/18* (2013.01); *C07C 13/15* (2013.01); *Y10S 428/917* (2013.01)
USPC ........... 313/504; 428/690; 428/917; 313/506; 257/40; 257/E51.05

(58) Field of Classification Search
None
See application file for complete search history.

(56) References Cited

U.S. PATENT DOCUMENTS

| 4,356,429 A | 10/1982 | Tang | ............................. 313/503 |
| 4,769,292 A | * 9/1988 | Tang et al. | ..................... 428/690 |

(Continued)

FOREIGN PATENT DOCUMENTS

| CN | 1388800 A | 1/2003 |
| CN | 1827732 A | 9/2006 |

(Continued)

OTHER PUBLICATIONS

Stenger-Smith et al., Makromolekulare Chemie, (1989), vol. 190, pp. 2995-3003.*

(Continued)

*Primary Examiner* — Jennifer Chriss
*Assistant Examiner* — Brett A Crouse
(74) *Attorney, Agent, or Firm* — Ballard Spahr LLP

(57) ABSTRACT

The present invention relates to a dinaphthyl ethylene derivative of formula (I), a process for preparing it, a film prepared from it useful in the manufacture of an organic light emitting device (OLED), an OLED including the film, and the use of the dinaphthyl ethylene derivative in the manufacture of an OLED.

(I)

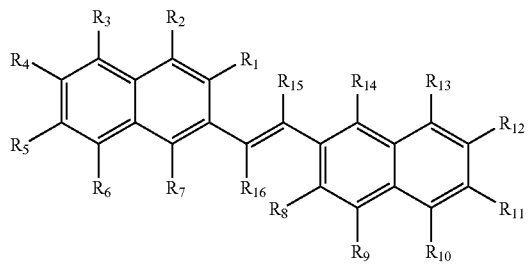

Wherein $R_1$ to $R_{16}$ are defined as in the specification.

4 Claims, 2 Drawing Sheets

(51) Int. Cl.

| | |
|---|---|
| C07D 333/24 | (2006.01) |
| C07C 15/58 | (2006.01) |
| C07C 13/567 | (2006.01) |
| C07D 309/34 | (2006.01) |
| C07C 255/09 | (2006.01) |
| C07C 211/54 | (2006.01) |
| C07C 45/46 | (2006.01) |
| C07C 15/62 | (2006.01) |
| C07C 45/68 | (2006.01) |
| C07D 233/96 | (2006.01) |
| C07D 413/14 | (2006.01) |
| C07D 219/06 | (2006.01) |
| C07C 15/38 | (2006.01) |
| C07D 209/08 | (2006.01) |
| C07C 15/60 | (2006.01) |
| C07D 403/10 | (2006.01) |
| C07D 209/44 | (2006.01) |
| C07D 333/08 | (2006.01) |
| C07D 213/68 | (2006.01) |
| C07C 251/86 | (2006.01) |
| C07D 209/86 | (2006.01) |
| C07D 207/323 | (2006.01) |
| C07C 211/58 | (2006.01) |
| C07C 43/285 | (2006.01) |
| C07D 213/74 | (2006.01) |
| H01L 51/00 | (2006.01) |
| C07C 17/10 | (2006.01) |
| C07D 251/24 | (2006.01) |
| C07D 309/32 | (2006.01) |
| C07C 245/10 | (2006.01) |
| C07C 17/16 | (2006.01) |
| C07D 271/107 | (2006.01) |
| C07C 25/22 | (2006.01) |
| C07D 215/06 | (2006.01) |
| C07D 277/66 | (2006.01) |
| C07D 307/54 | (2006.01) |
| C07D 471/22 | (2006.01) |
| C07D 221/14 | (2006.01) |
| C07C 22/08 | (2006.01) |
| C07C 17/263 | (2006.01) |
| C07C 43/225 | (2006.01) |
| C07D 307/91 | (2006.01) |
| C07C 13/465 | (2006.01) |
| C07D 401/04 | (2006.01) |
| C07C 13/72 | (2006.01) |
| C07C 45/29 | (2006.01) |
| C07C 255/52 | (2006.01) |
| C07D 471/06 | (2006.01) |
| C07D 235/20 | (2006.01) |
| C07C 45/00 | (2006.01) |
| C07D 307/66 | (2006.01) |
| C07C 13/15 | (2006.01) |
| H01L 51/50 | (2006.01) |

(56) References Cited

U.S. PATENT DOCUMENTS

| | | | | |
|---|---|---|---|---|
| 5,536,949 | A | * | 7/1996 | Hosokawa et al. ............ 257/40 |
| 2006/0147750 | A1 | * | 7/2006 | Ujiie et al. .................... 428/690 |
| 2006/0222888 | A1 | | 10/2006 | Lee et al. ...................... 428/690 |
| 2006/0269781 | A1 | | 11/2006 | Lai et al. ....................... 428/690 |

FOREIGN PATENT DOCUMENTS

| | | | |
|---|---|---|---|
| CN | 101009363 | 8/2007 | |
| JP | 63-158556 | * 7/1988 | ............... G03G 5/06 |
| JP | 2006124333 | 5/2006 | |
| JP | 2008-18896 | 10/2008 | |
| WO | WO 2007/123137 A1 | 11/2007 | |

OTHER PUBLICATIONS

Chen et al., "Ortho-Substituent Effect on Fluorescence and Electroluminescence of Arylamino-Substituted Coumarin and Stilbene," *Org. Lett.*, 5(8):1261-1264 (2003).

Danel et al., "Blue-Emitting Anthracenes with End-Capping Diarylamines," *Chem. Mater.* 14(9):3860-3865 (2002).

Guan et al., "High-Performance Blue Electroluminescent Devices Based on 2-(4-biphenylyl)-5-(4-carbzaole-(9-yl)phenyl-1, 3, 4-oxadiazole," *Chem. Commun.*, 2708-2709(2003).

Yeh et al., "Readily Synthesised Arylamino Fumaronitrile for Non-Doped Red Organic Light-Emitting Diodes," *Chem. Commun.*, 2632-2633 (2003).

Yu et al., "Diaminoanthracene Derivatives as High-Performance Green Host Electroluminescent Materials," *Chem. Mater.* 14(9):3958-3963 (2002).

* cited by examiner

DINAPHTHYL ETHYLENE DERIVATIVCE, PROCESS FOR PREPARING IT, FILM PREPARED FROM IT, AND OLED INCLUDING THE FILM

CROSS REFERENCE TO RELATED APPLICATIONS

The present application claims priority to Chinese Patent Application No. 200710063411.5, filed Jan. 31, 2007, which application is incorporated herein fully by this reference.

BACKGROUND OF THE INVENTION

1. Technical Field of the Invention

The present invention relates to a dinaphthyl ethylene derivative, a process for preparing it, a film prepared from it useful in the manufacture of an organic light emitting device (abbreviated as OLED hereinbelow), an OLED including the film, and the use of the dinaphthyl ethylene derivative in the manufacture of an OLED.

2. Description of the Related Art

OLED came into being in the 1960s. In 1963, P. Pone et al first observed the light emitting phenomenon of anthracene crystal. However, its driving voltage was as high as 400 V, and for that reason this phenomenon failed to attract sufficient human attention. In 1987, an amorphous film diode, an organic light emitting device, was made of Alq3 and HTM-2 by sublimation coating by C. W. Tang et al in Kodak., and its driving voltage was as low as less than 20 V. From then on, OLED began to attract much attention the world wide (see U.S. Pat. No. 4,356,429). OLED features high brightness, wide angle, quick electric response, low driving voltage, low energy consumption, full color, high contrast, light weight, easy making and so on. Thus, it is widely used as panel luminance diode, for example, in flat panel display and light pan.

OLED comprises two electrodes and at least one organic film disposed between them. The organic film is made from an electroluminescent compound. Typically, electroluminescent compound with a structure of D-π-X (D means Donor Group) contributes to form an OLED having a high efficiency of fluorescence. Additionally, the emission wavelength of the OLED depends on X: the compound wherein X represents a strong donor group, such as a diaminoanthracene derivative synthesized by Cheng C. H. (see Chem. Mater., 2002, 14:3958), forms an OLED usually emitting green light; the substance wherein X represents a weak donor group, such as a coumarin derivative synthesized by Chen C. T. (see Org. lett., 2003, 5: 1261), a anthracyl arylamine synthesized by Lin J. T. (see Chem. Mater., 2002,14:3860), or a carbazolyl oxadiazole synthesized by Huang C. G. (see Chem. Commun., 2003, 2708), forms an OLED emitting blue light; the substance wherein X represents a strong acceptor group, such as a NPAFN derivatives (see Chem. Commun., 2003, 2632), forms an OLED emitting red light. On the other hand, the π bridge is also important. A too large π bridge renders the emission wavelength of the resulting OLED longer, a phenomenon which in turn negatively affects color purity of the OLED. Conversely, a too small π bridge reduces the current efficiency of the OLED. For instance, an electroluminescent compound with a diphenyl ethylene group forms an OLED showing bad performance in terms of current efficiency and life span (see CN1388800A).

SUMMARY OF THE INVENTION

The object of this invention is to provide a novel electroluminescent compound. The compound is capable of forming an OLED features high color purity, high fluorescence yield, and high electric luminance yield; in addition, the compound is easy to synthesize and can easily form films. In addition, the compound is capable of forming an OLED having an emission wavelength which changes with the substituting groups and substituted positions in the compound.

The compound according to the invention is a dinaphthyl ethylene derivative represented by the following formula (I):

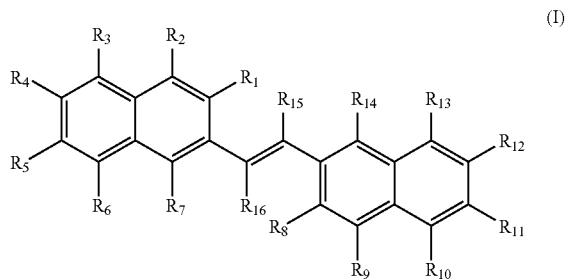

(I)

Wherein $R_1$ to $R_{16}$ each independently represent a hydrogen atom, a fluorine atom, a cyano, a substituted or unsubstituted alkyl group, alkoxy group, amino group, alkylthio group, aryl group, aromatic heterocyclic group, aromatic fused ring group, aromatic fused heterocyclic group or arylamino group, and at least one of $R_1$ to $R_{14}$ is not a hydrogen atom.

Another object of the invention is to provide a process for preparing the dinaphthyl ethylene derivative represented by the above formula (I), comprising one of the following processes a), b), c) and d):

a) reacting a compound of formula (I-a) with a compound of formula (I-b) in the presence of $TiCl_4$ and Zn in an inert solvent under an inert gas atmosphere, and then optionally introducing the substituents where necessary;

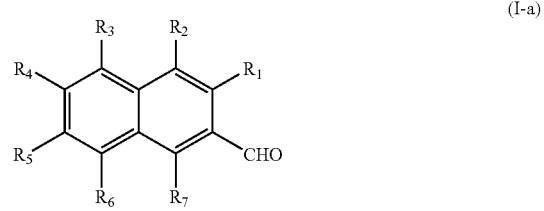

(I-a)

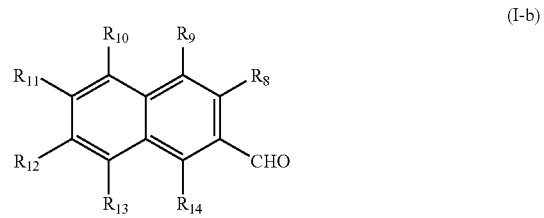

(I-b)

Wherein $R_1$-$R_{14}$ are defined as above;

b) reacting a compound of formula (I-a') with a compound of formula (I-b') in the presence of $TiCl_4$ and Zn in an inert solvent under an inert gas atmosphere, and then optionally introducing the substituents where necessary;

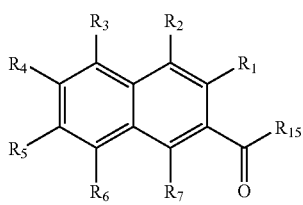
(I-a')

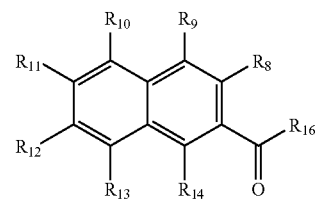
(I-b')

Wherein $R_1$-$R_{16}$ are defined as above;

c) reacting a compound selected from the group consisting of compounds of formula (I-a), formula (1-a'), formula (1-b) and formula (1-b') above with a compound of formula (I-c), in the presence of an alkali in an inert solvent, and then optionally introducing the substituents where necessary;

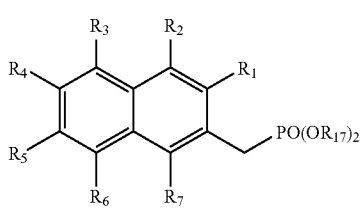
(I-c)

Wherein $R_1$-$R_7$ are defined as above, and
$R_{17}$ is a linear or branched alkyl containing 1-6 carbon atoms; and d) reacting a compound of formula (I-d) with a compound of formula (I-e) in the presence of an alkali metal or alkali-earth metal alcoholate and $I_2$ in an inert solvent, and then optionally introducing the substituents where necessary,

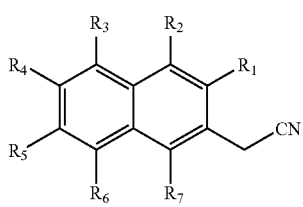
(I-d)

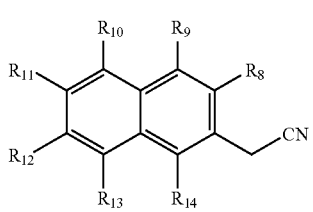
(I-e)

Wherein $R_1$-$R_{14}$ are defined as above.

A further object of the invention is to provide a film prepared from the dinaphthyl ethylene derivative represented by the above formula (I) wherein the symbols are defined as above, said film useful in the manufacture of an OLED; the film is supported on a substrate and is deposited, by a known process, including evaporation or sputtering, on the substrate.

A still further object of the invention is to provide an OLED, including a film prepared from the dinaphthyl ethylene derivative represented by the above formula (I) wherein the symbols are defined as above.

A still further object of the invention is to provide the method of use of the dinaphthyl ethylene derivative represented by the above formula (I) wherein the symbols are defined as above in the manufacture of an OLED.

OLEDs including a film prepared from the dinaphthyl ethylene derivative of the present invention show excellent performances, such as high color purity and high luminescent efficiency.

DETAILED DESCRIPTION OF PREFERRED EMBODIMENTS

Figure 1:
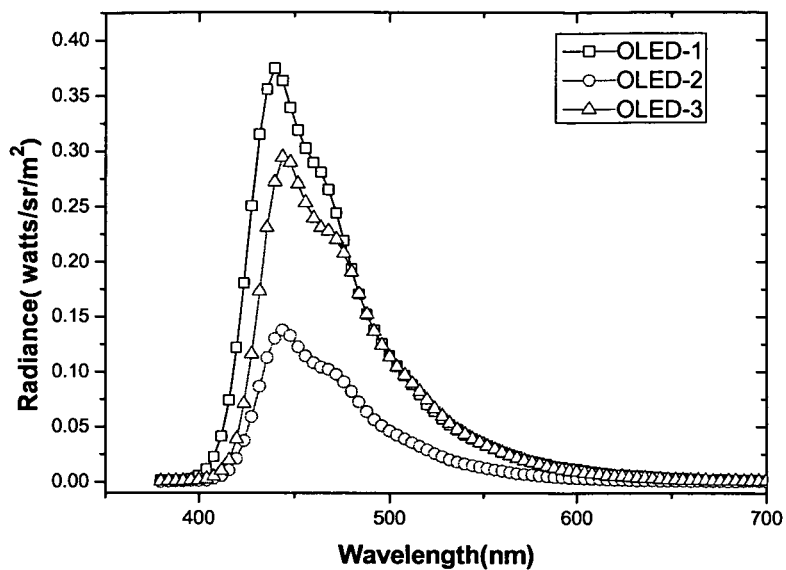
FIG. 1 shows the electroluminescence spectra of OLED-1 to OLED-3.

The dinaphthyl ethylene derivative according to the invention is represented by the following formula (I):

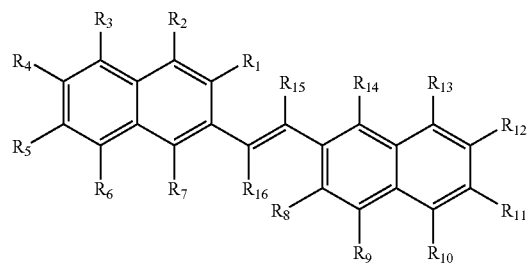
(I)

Wherein $R_1$ to $R_{16}$ each independently represent a hydrogen atom, a fluorine atom, a cyano, a substituted or unsubstituted alkyl group, alkoxy group, amino group, alkylthio group, aryl group, aromatic heterocyclic group, aromatic fused ring group, aromatic fused heterocyclic group or arylamino group, and at least one of $R_1$ to $R_{14}$ is not a hydrogen atom.

In a preferred embodiment of the present invention, in the above formula (I), $R_1$ to $R_{16}$ each independently represent a hydrogen atom, a fluorine atom, a cyano group, a substituted or unsubstituted alkyl group having 1 to 30 carbon atoms, a substituted or unsubstituted alkoxy group having 1 to 30 carbon atoms, a substituted or unsubstituted amino group having 2 to 30 carbon atoms, a substituted or unsubstituted alkylthio group having 1 to 30 carbon atoms, a substituted or unsubstituted aryl group having 6 to 20 carbon atoms, a substituted or unsubstituted aromatic fused ring group having 6 to 20 carbon atoms, a substituted or unsubstituted aromatic heterocyclic group having 4 to 20 carbon atoms, a substituted or unsubstituted aromatic fused heterocyclic group having 4 to 20 carbon atoms or a substituted or unsubstituted arylamino group having 6 to 30 carbon atoms, and at least one of $R_1$ to $R_{14}$ is not a hydrogen atom.

In a further preferred embodiment of the present invention, $R_1$ to $R_{16}$ are each independently selected from the groups consisting of hydrogen atom, fluorine atom, cyano group, methyl, ethyl, isopropyl, tert-butyl, methoxy, ethoxy, isopropoxy, tert-butoxy, N,N-dimethyl amino, N,N-diethyl amino, methylthio, ethylthio, isopropylthio, tert-butylthio, phenyl, biphenyl, naphthyl, anthryl, pyrenyl, fluorenyl, naphthacenyl, pyridyl, quinolyl, benzothiophenyl, benzofuranyl, indolyl, benzimidazolyl, benzothiazol, N-methyl-N-phenylamino, N,N-diphenylamino, N-phenyl-N-(1-naphthyl)amino, N-phenyl-N-(2-naphthyl)amino, N,N-di(1-naphthyl)amino, N,N-di(2-naphthyl)amino or carbazolyl group, pyrrolyl, thiophenyl, furanyl, pyrazolyl, imidazolyl, oxazolyl, thiazolyl, pyridyl, quinolyl, isoquinolyl, carbazolyl, phenanthridinyl, benzothiophenyl, benzofuranyl, benzimidazolyl, benzoxazolyl, benzothiazolyl, thiadiazole, oxadiazolyl, pyrimidinyl, pyrazinyl, pyridazinyl, azabenzothiophenyl, indolyl, thiaindolyl, thiaisoindolyl, thiaindazolyl and pyrazoloquinolyl, and at least one of $R_1$ to $R_{14}$ is not a hydrogen atom.

A still further preferred dinaphthyl ethylene derivative of the invention is one represented by the following formula (II):

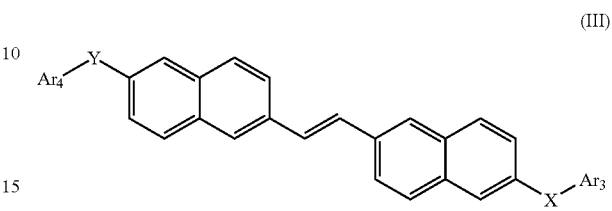

(II)

Wherein $Ar_1$ and $Ar_2$ each independently represent a hydrogen atom, a substituted or unsubstituted aryl group, aryl-vinyl group, aromatic fused ring group, aromatic fused ring-substituted vinyl group, arylamino group, fused ring group having at least one nitrogen atom or heterocyclic group having at least one nitrogen atom.

In a particularly preferred embodiment of the invention, in the above formula (II), $Ar_1$ and $Ar_2$ each independently represent a hydrogen atom, a substituted or unsubstituted aryl group having 6 to 20 carbon atoms, aryl-vinyl group having 8 to 40 carbon atoms, aromatic fused ring group having 6 to 30 carbon atoms, aromatic fused ring-substituted vinyl group having 14 to 60 carbon atoms, arylamino group having 6 to 30 carbon atoms, fused ring group having at least one nitrogen atom and 6 to 30 carbon atoms or heterocyclic group having at least one nitrogen atom and 6 to 30 carbon atoms.

In a more particularly preferred embodiment of the invention, in the above formula (II), $Ar_1$ and $Ar_2$ each independently represent a phenyl, biphenyl, naphthyl, anthryl, pyrenyl, fluorenyl, naphthacenyl, phenylvinyl, naphthylvinyl, anthrylvinyl, fluorenylvinyl, phenanthrylvinyl, biphenylvinyl, diphenylvinyl, phenylnaphthylvinyl, N-methyl-N-phenylamino, N,N-diphenylamino, N-phenyl-N-(1-naphthyl)amino, N-phenyl-N-(2-naphthyl)amino, N,N-di(1-naphthyl)amino, N,N-di(2-naphthyl)amino, substituted or unsubstituted quinoxalinyl or carbazolyl group.

Another still further preferred dinaphthyl ethylene derivative of the invention is one represented by the following formula (III):

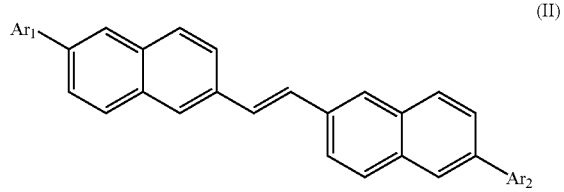

(III)

Wherein X and Y are independently selected from the group consisting of methylene, aromatic 5 or 6-membered ring having 1 to 3 hetero atoms and 4 to 20 carbon atoms, aromatic fused ring having 1 to 3 hetero atoms and 6 to 20 carbon atoms, and at least one of X and Y is not a methylene; and $Ar_3$ and $Ar_4$ represent a hydrogen atom, fluorine atom, carbonyl group, cyano group, acyloxy, vinylidene, a substituted or unsubstituted alkyl group having 1 to 30 carbon atoms, a substituted or unsubstituted alkoxy group having 1 to 30 carbon atoms, a substituted or unsubstituted amino group having 2 to 30 carbon atoms, a substituted or unsubstituted alkylthio group having 1 to 30 carbon atoms, a substituted or unsubstituted aryl group having 6 to 20 carbon atoms, aromatic fused ring group having 6 to 20 carbon atoms or arylamino group having 6 to 30 carbon atoms.

In a particularly preferred embodiment of the invention, in the above formula (III), X and Y are independently selected from the group consisting of methylene, pyrrolyl, thiophenyl, furanyl, pyrazolyl, imidazolyl, oxazolyl, thiazolyl, pyridyl, quinolyl, isoquinolyl, carbazolyl, phenanthridinyl, benzothiophenyl, benzofuranyl, benzimidazolyl, benzoxazolyl, benzothiazolyl, oxadiazolyl, pyrimidinyl, pyrazinyl, pyridazinyl, indolyl, and at least one of X and Y is not a methylene; and $Ar_3$ and $Ar_4$ are independently selected from the group consisting of a hydrogen atom, fluorine atom, carbonyl group, cyano group, acyloxy, vinylidene, methyl, ethyl, isopropyl, tert-butyl, methoxy, ethoxy, isopropoxy, tert-butoxy, N,N-dimethyl amino, N,N-diethyl amino, methylthio, ethylthio, isopropylthio, tert-butylthio, phenyl, biphenyl, naphthyl, anthryl, pyrenyl, fluorenyl, naphthacenyl, N-methyl-N-phenylamino, N,N-diphenylamino, N-phenyl-N-(1-naphthyl)amino, N-phenyl-N-(2-naphthyl)amino, N,N-di(1-naphthyl)amino, N,N-di(2-naphthyl)amino or carbazolyl group, p-carbazolyl phenyl group or p-N,N-diphenylamino phenyl.

In a more particularly preferred embodiment of the invention, in the above formula (III), X, Y, $Ar_3$ and $Ar_4$ are as follows:

| X | Y | $Ar_3$ | $Ar_4$ |
|---|---|---|---|
| ![pyrrole with CH3] | ![benzothiophene with S] | H, F | phenyl |

-continued
| X | Y | Ar₃ | Ar₄ |
|---|---|---|---|
| 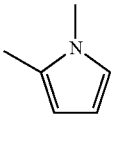 | 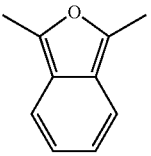 |  | 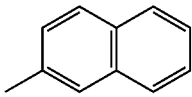 |
| 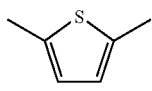 | 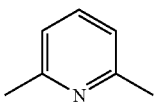 | 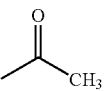 | 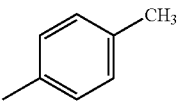 |
| 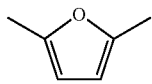 | 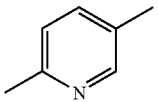 | 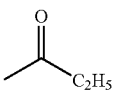 | 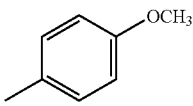 |
| 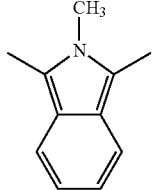 | 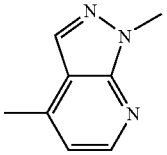 |  |  |
| 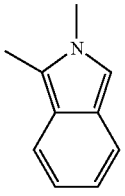 | 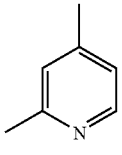 |  | 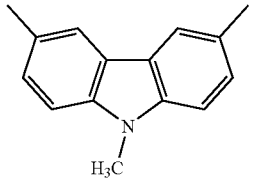 |
| 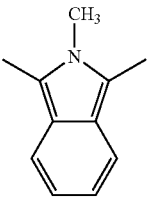 | 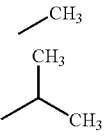 | 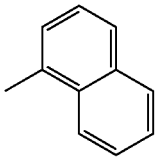 | 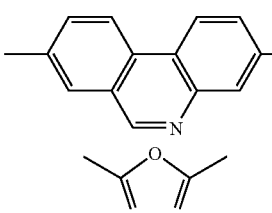 |
| 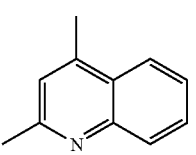 | 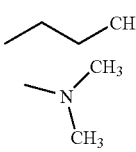 | 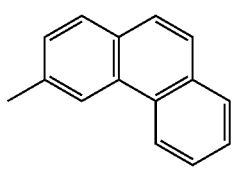 | 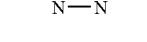 |
|  |  |  | 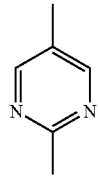 |
| 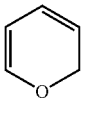 | 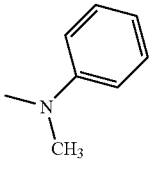 | | 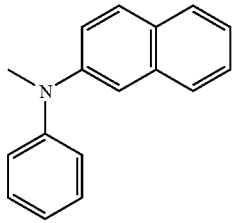 |

-continued
| X | Y | Ar₃ | Ar₄ |
|---|---|---|---|
| 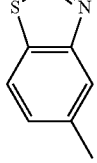 |  | 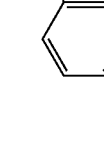 | 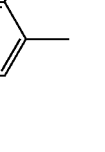 |
| 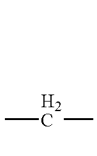 | |  | 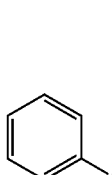 |
| | |  |  |
| | | 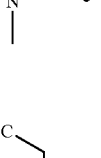 |  |
| | |  | 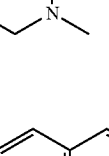 |
Specifically, as the dinaphthyl ethylene derivative of the invention, the following compounds can be listed:
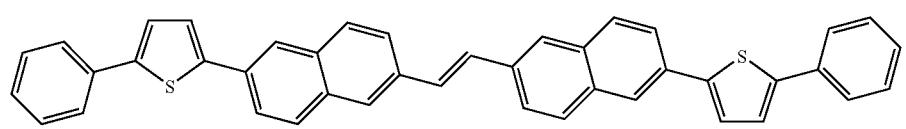
C1
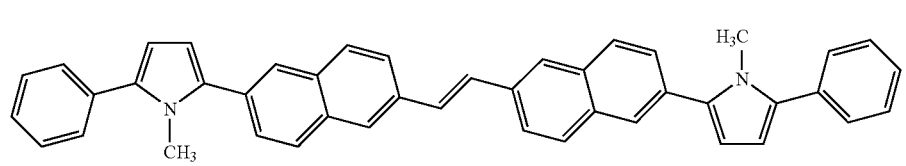
C2

-continued
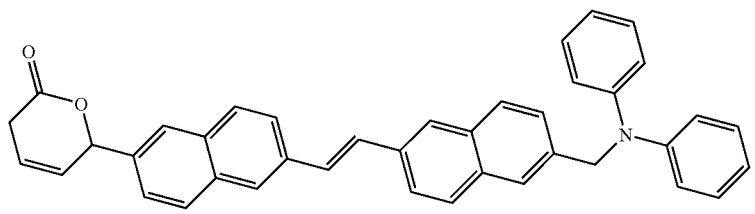
C3
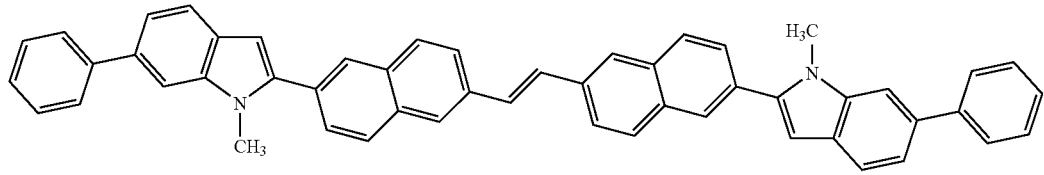
C4
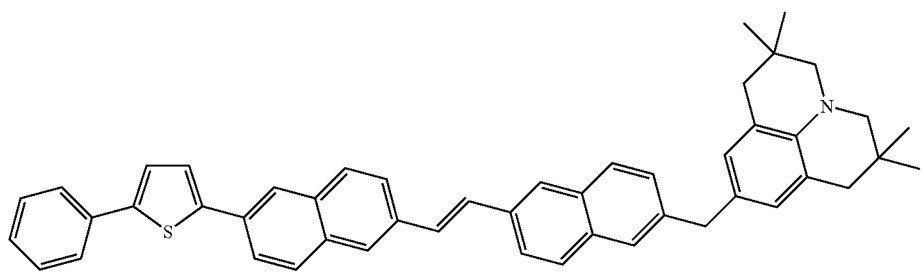
C5
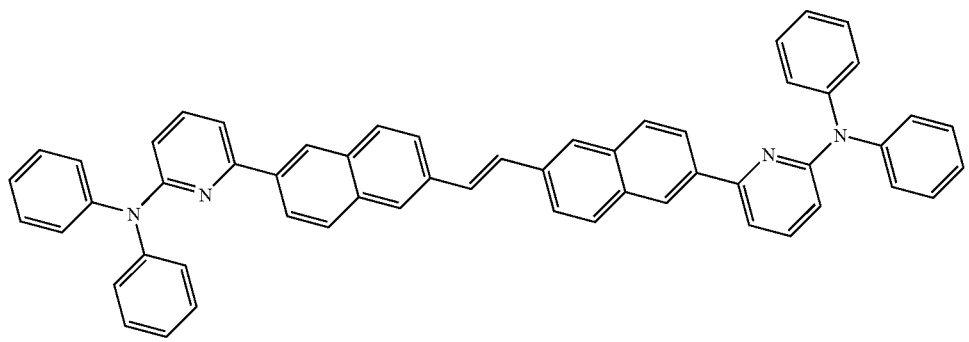
C6
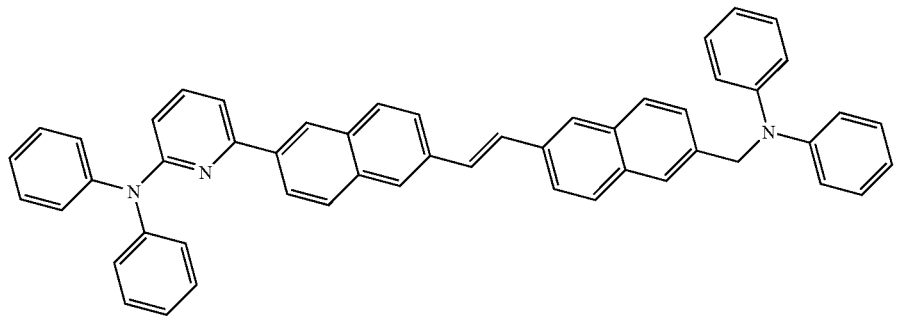
C7
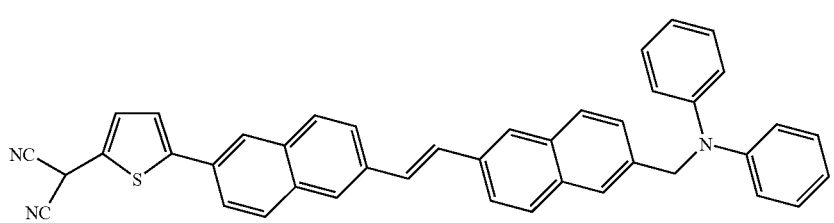
C8

-continued
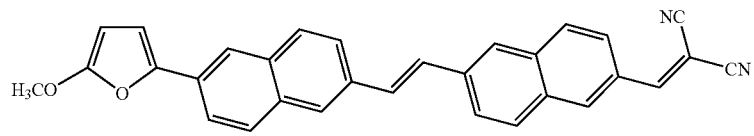
C9
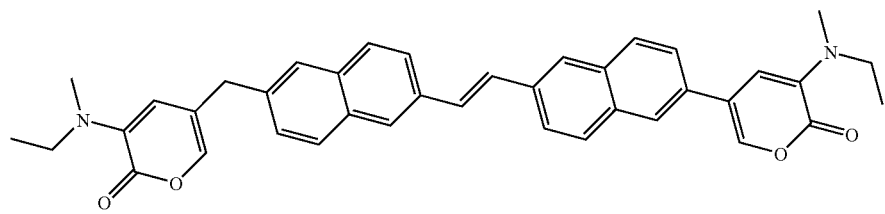
C10
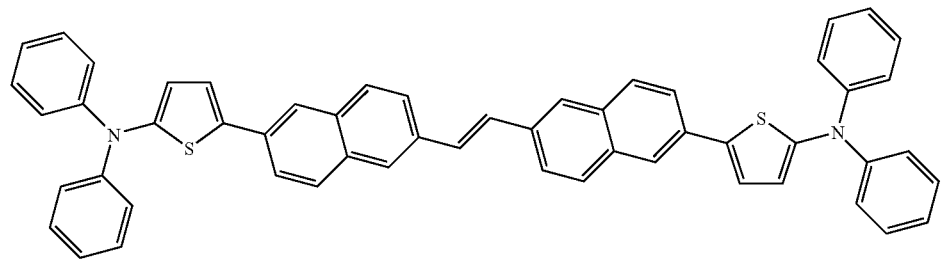
C11
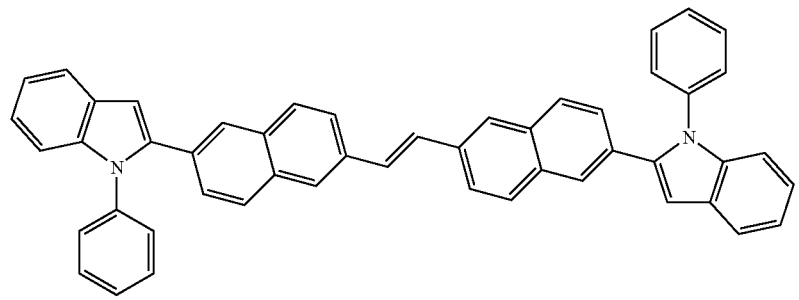
C12
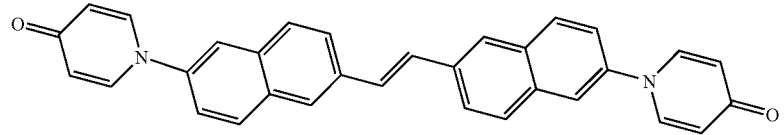
C13
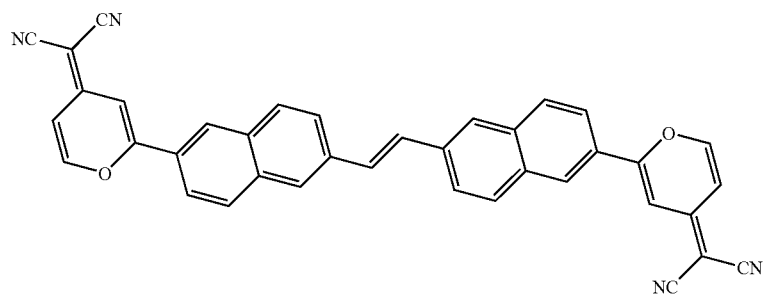
C14

-continued
C15
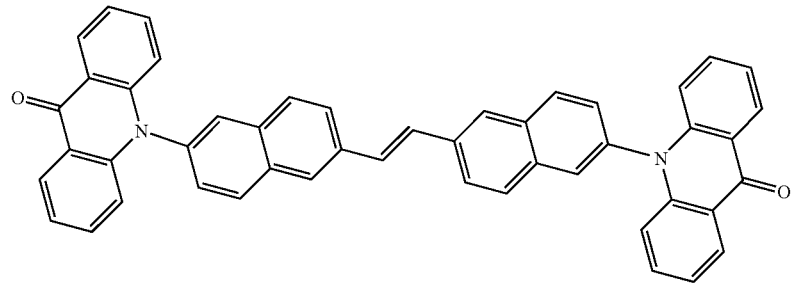
C16
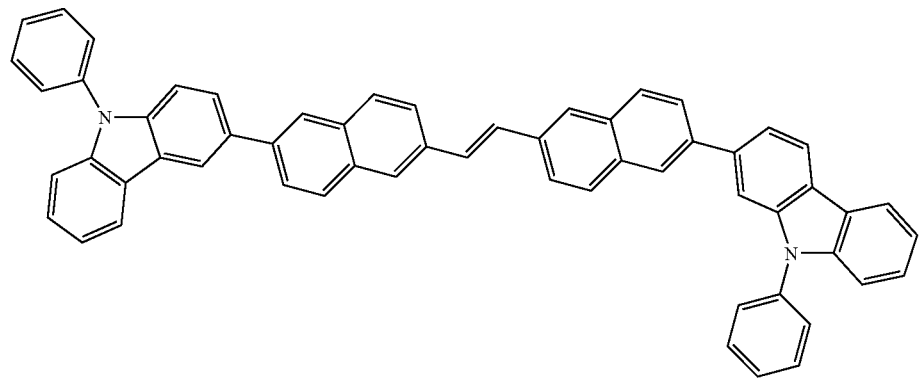
C17
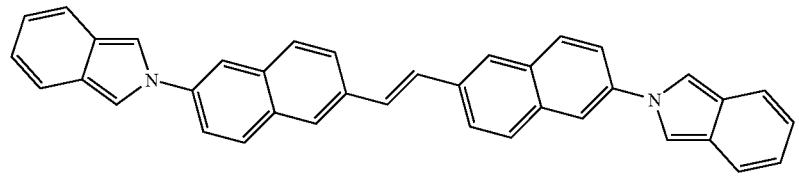
C18
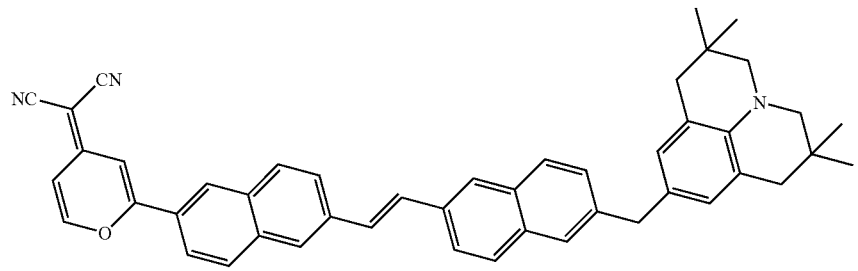
C19
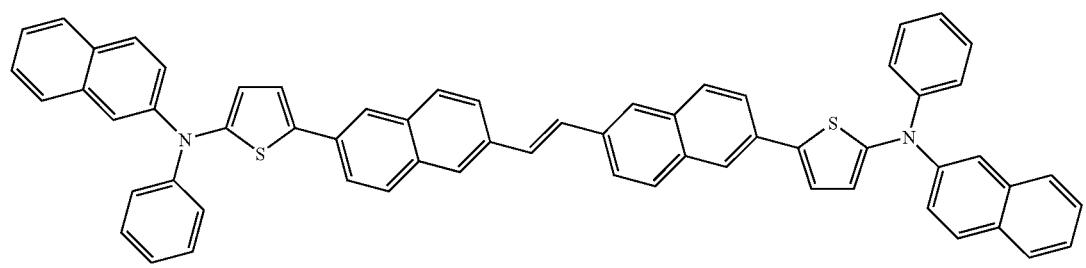

C20
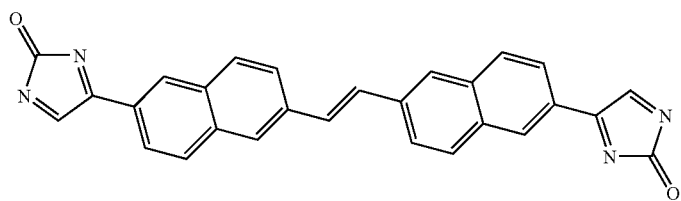
C21
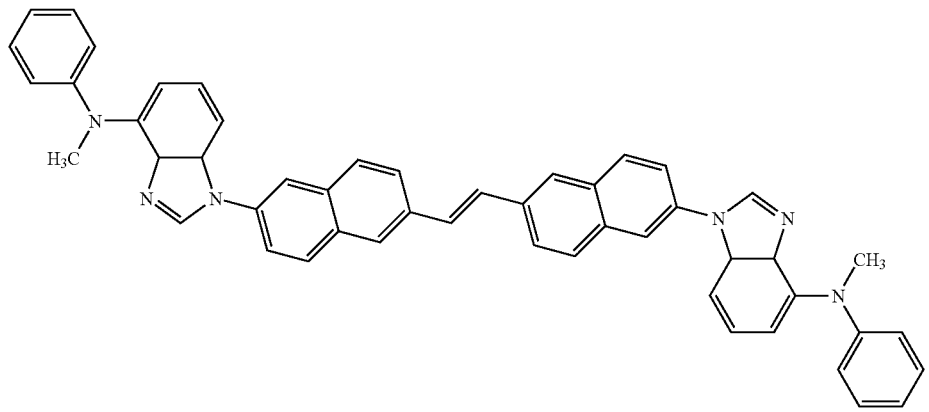
C22
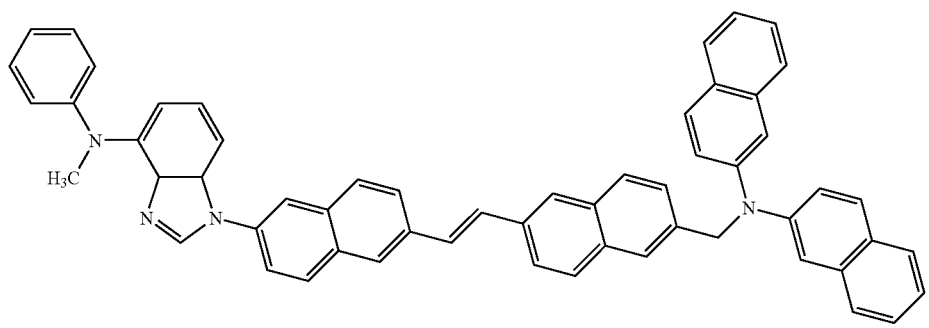
C23
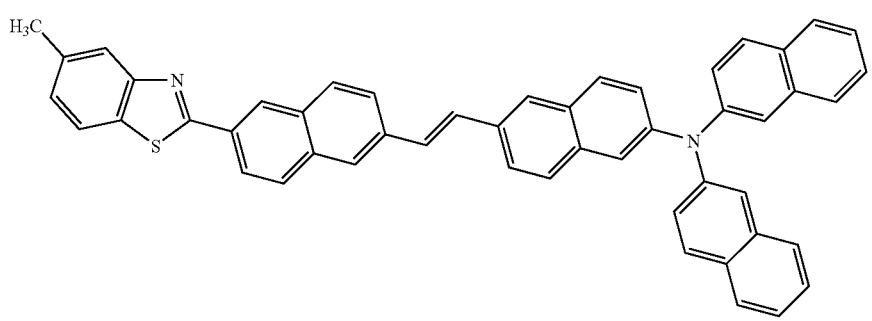
C24
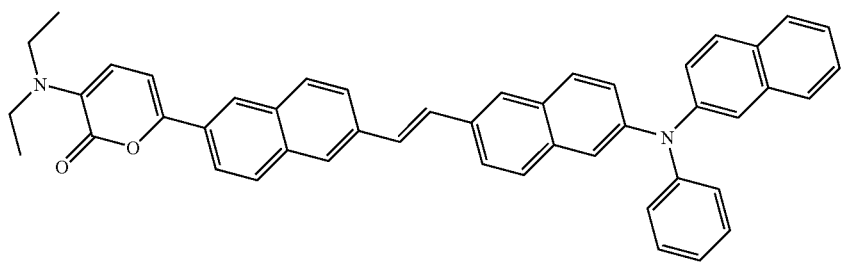

-continued
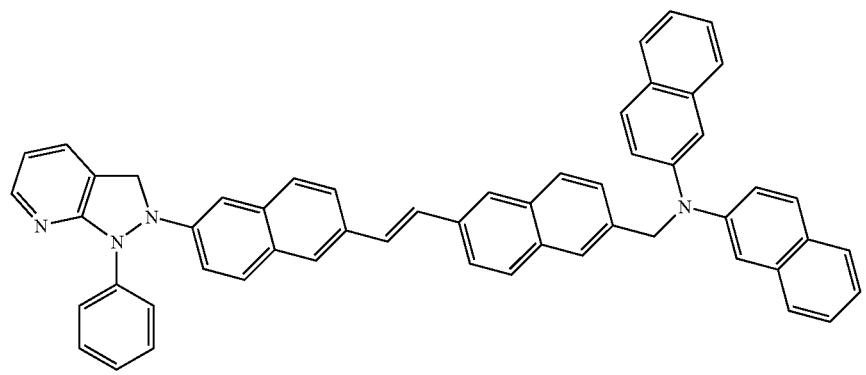
C25
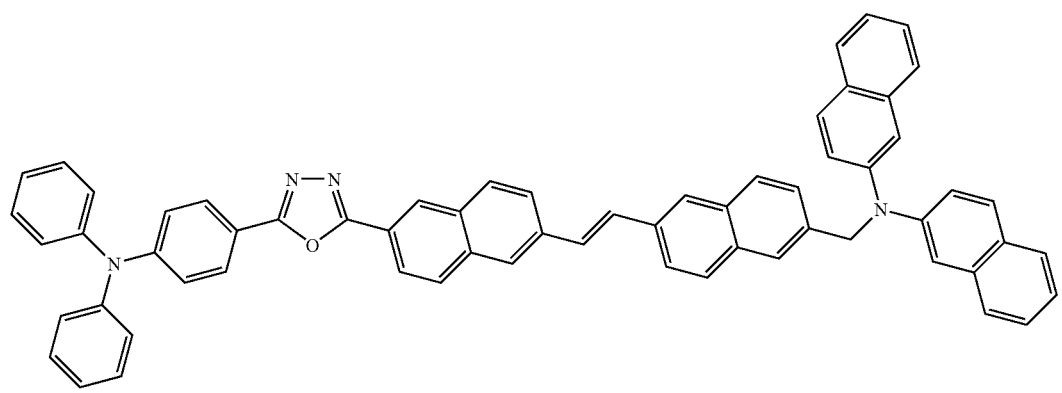
C26
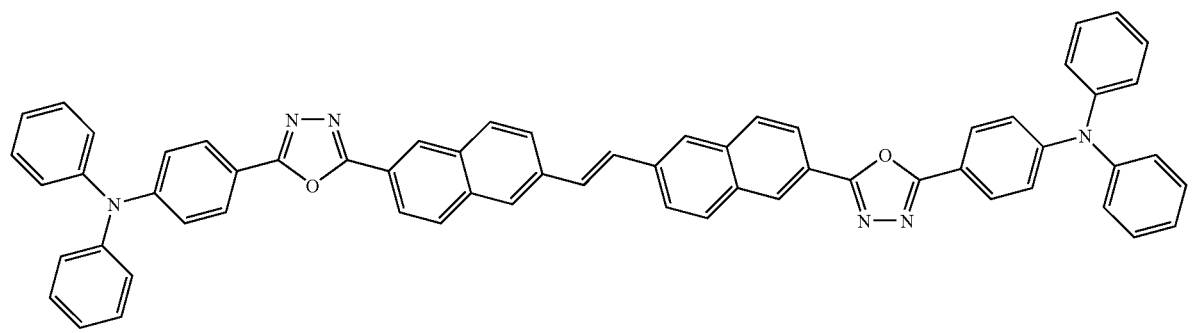
C27
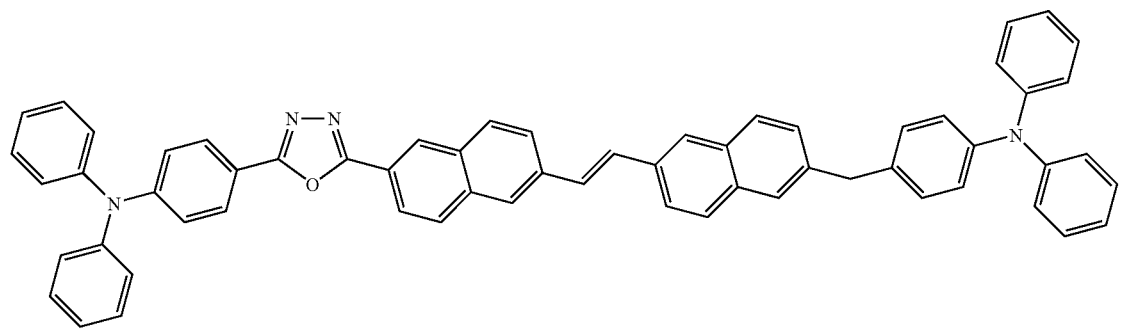
C28

-continued
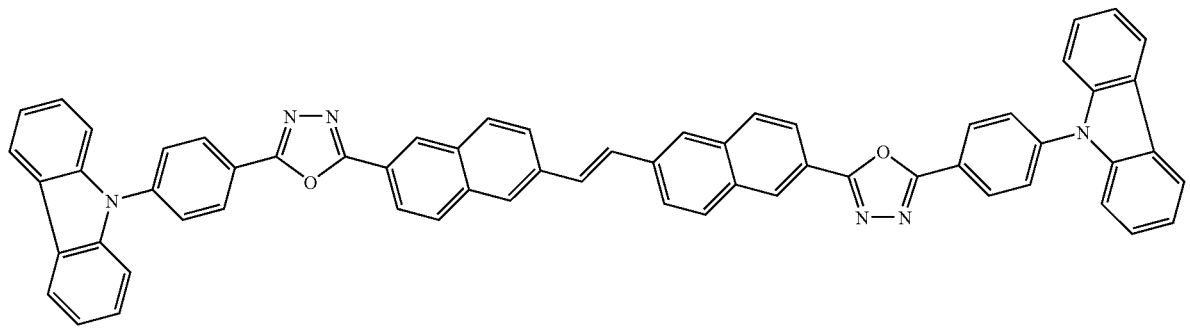
C29
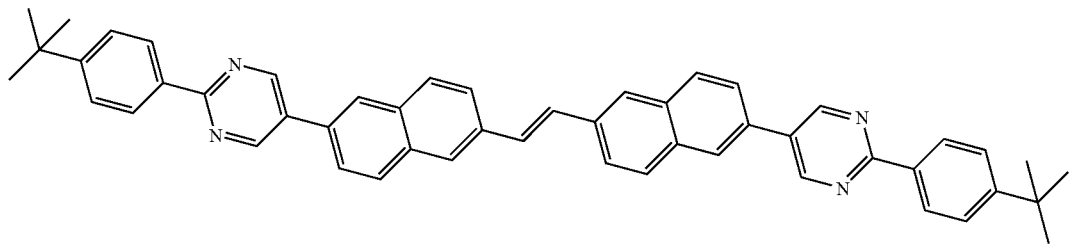
C30
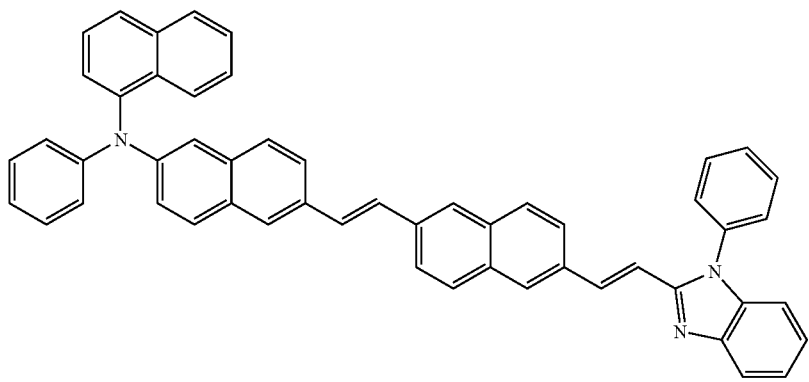
C31
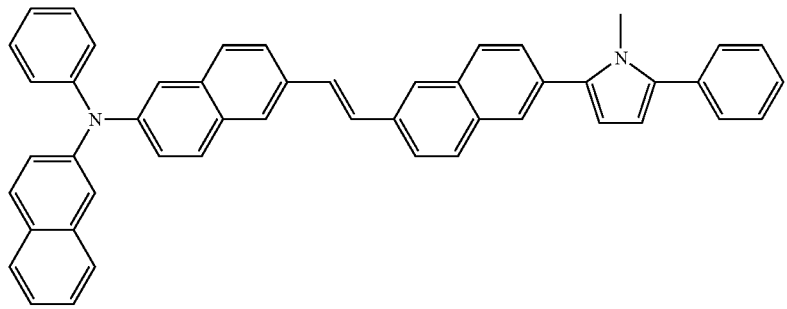
C32
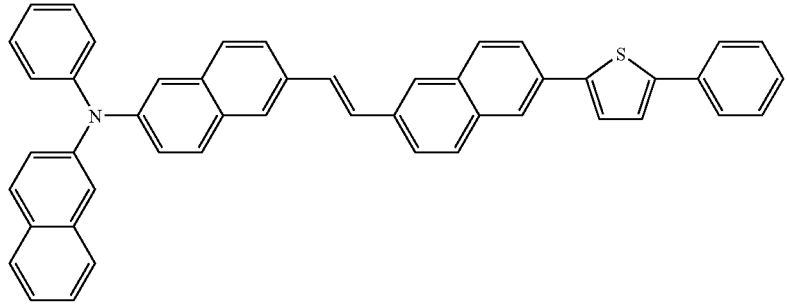
C33

-continued
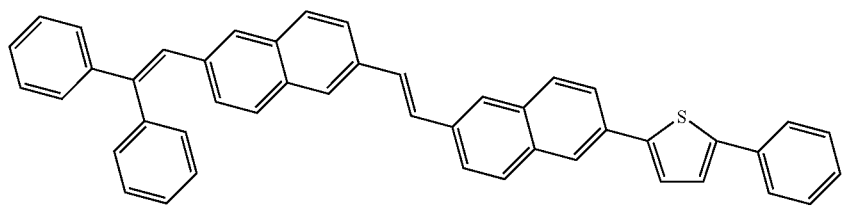
C34
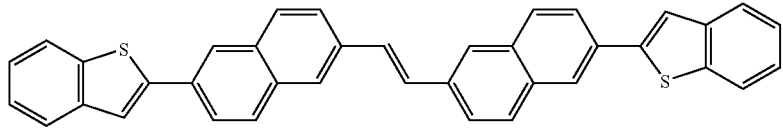
C35
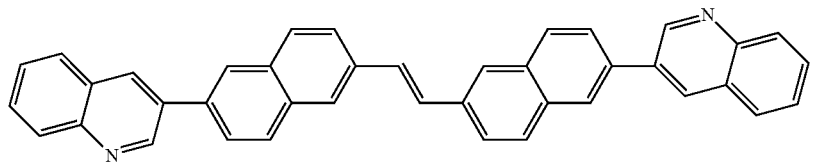
C36
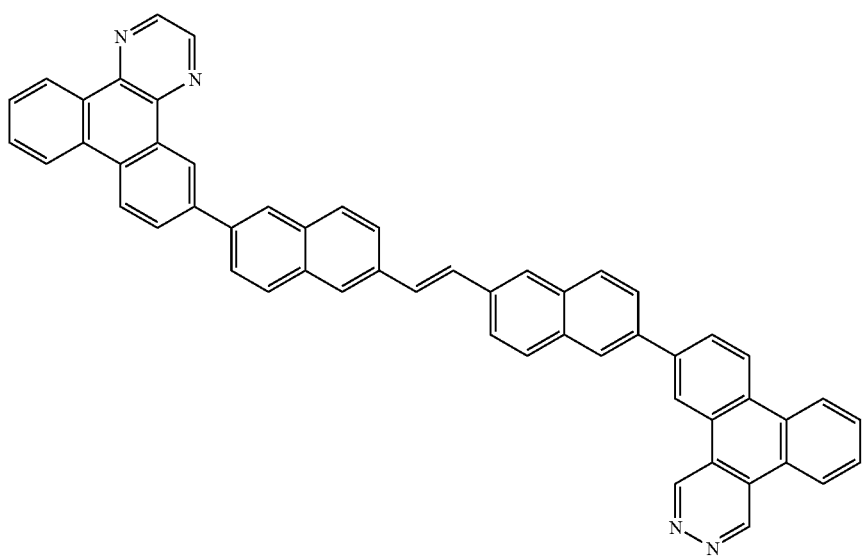
C37
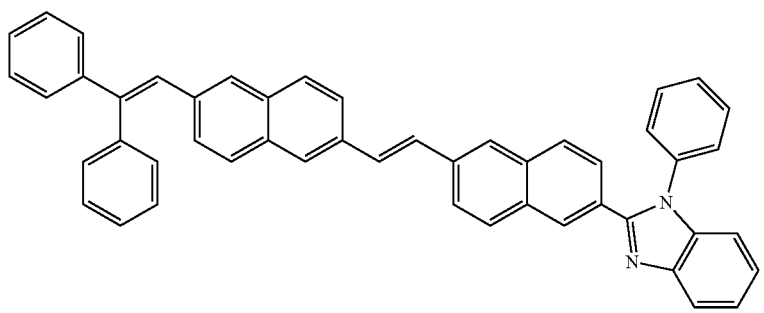
C38

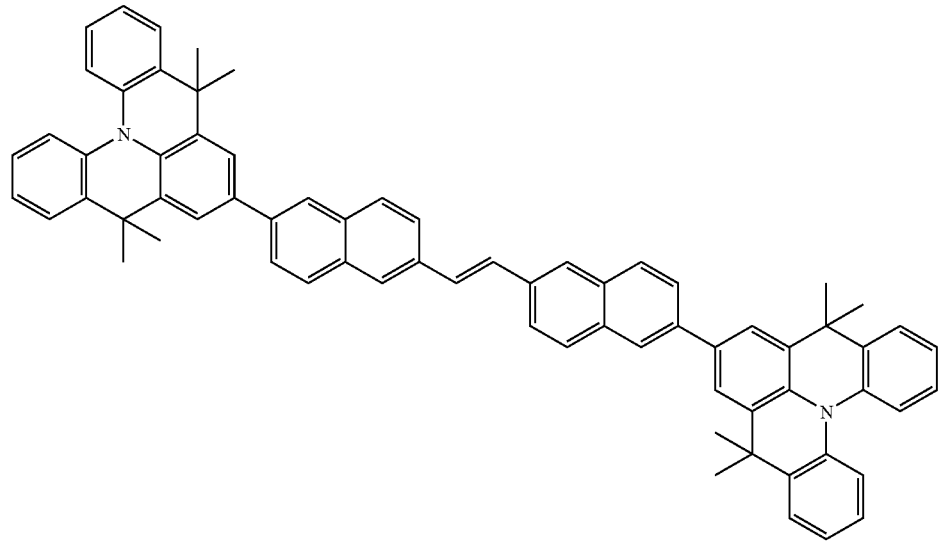
C39
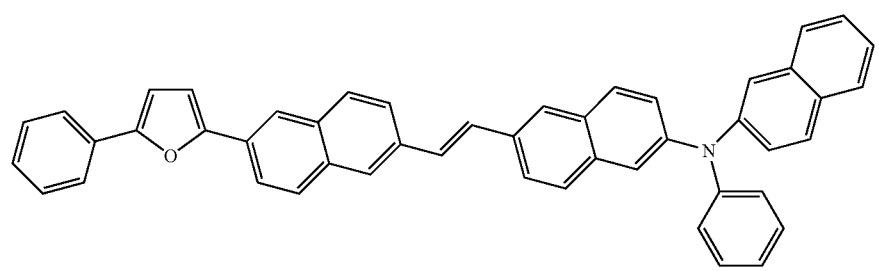
C40
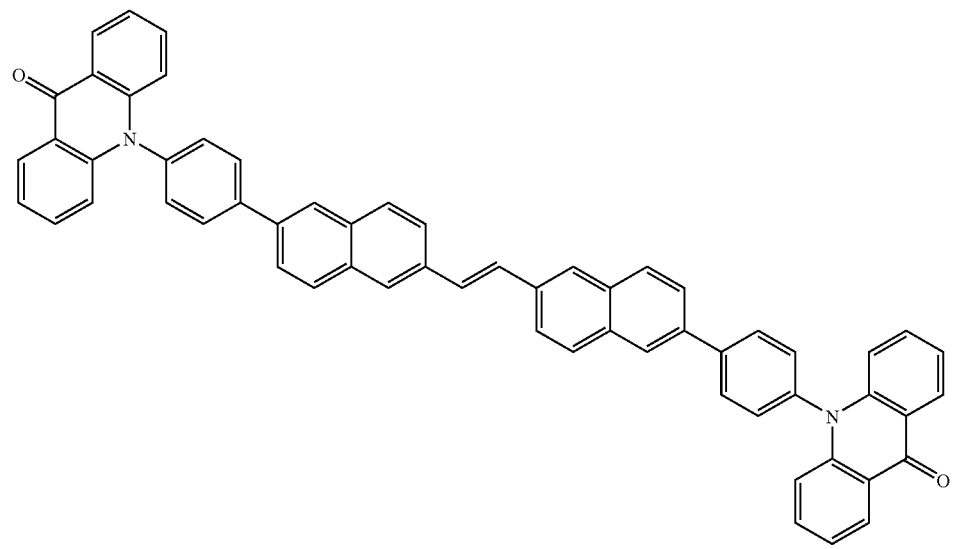
C41

C42
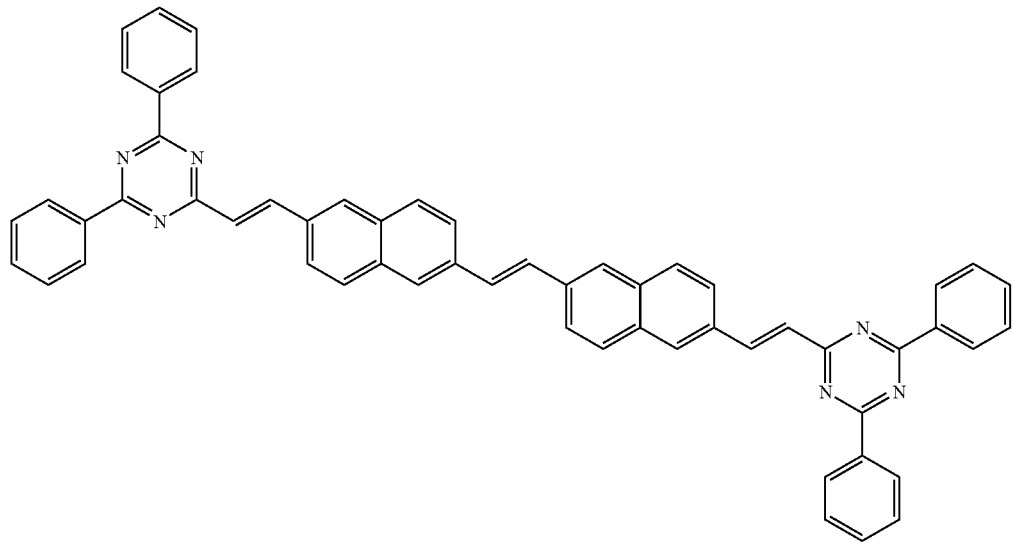
C43
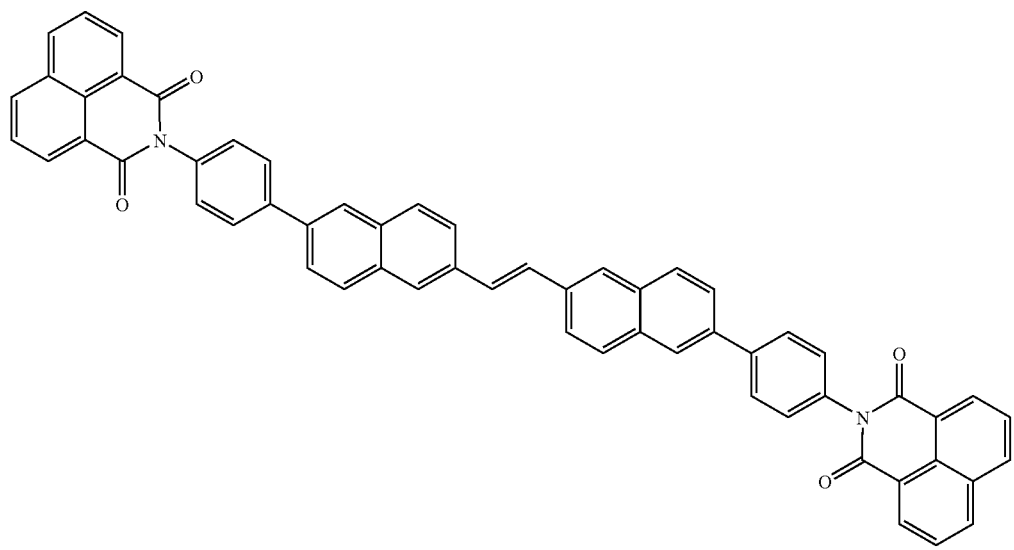
C44
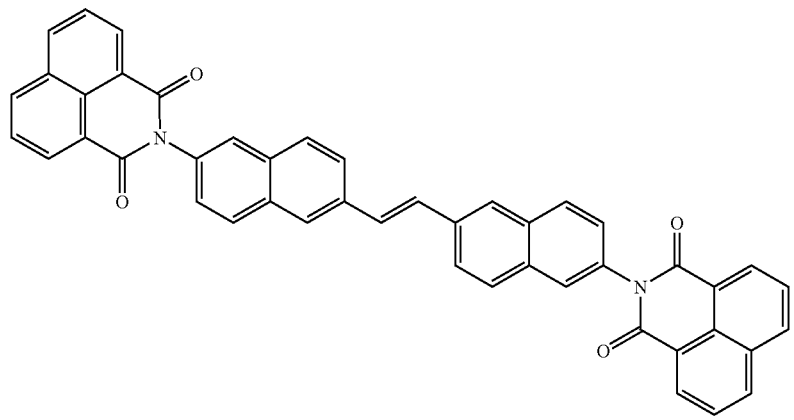

-continued
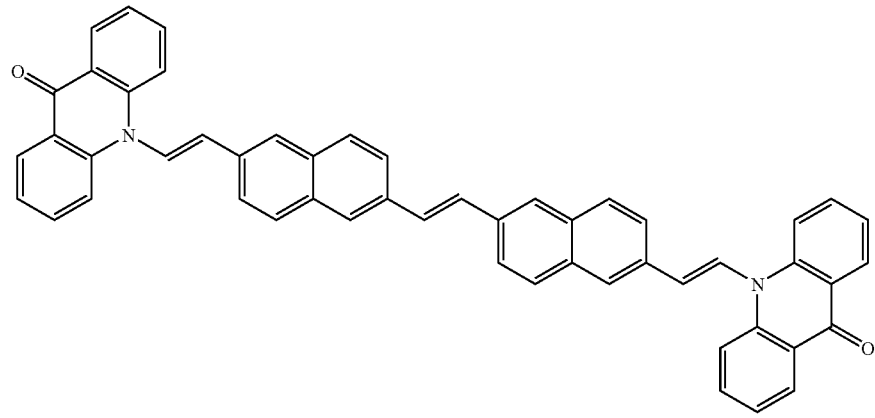
C45
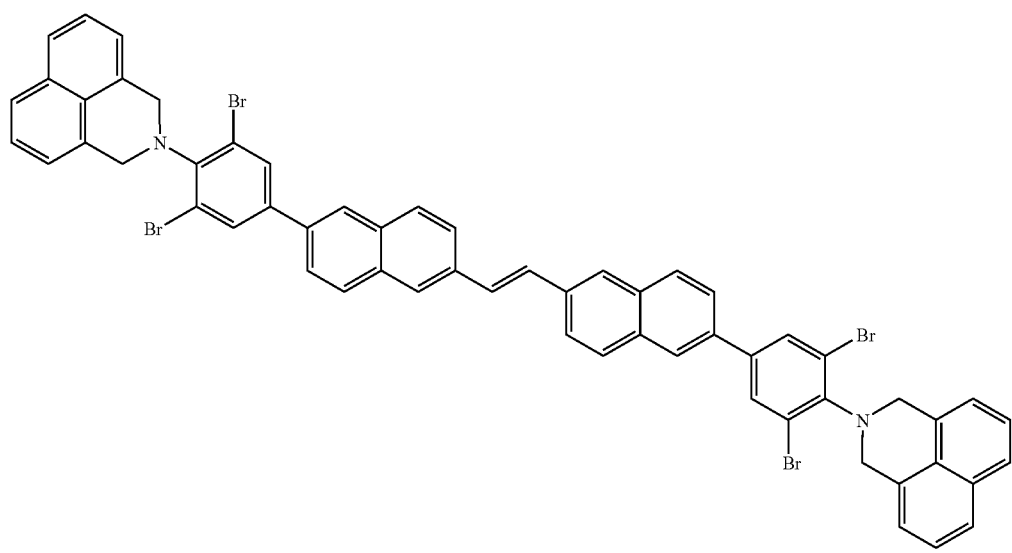
C46
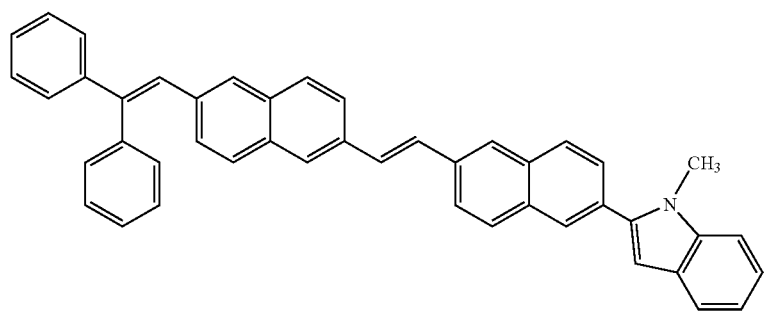
C47
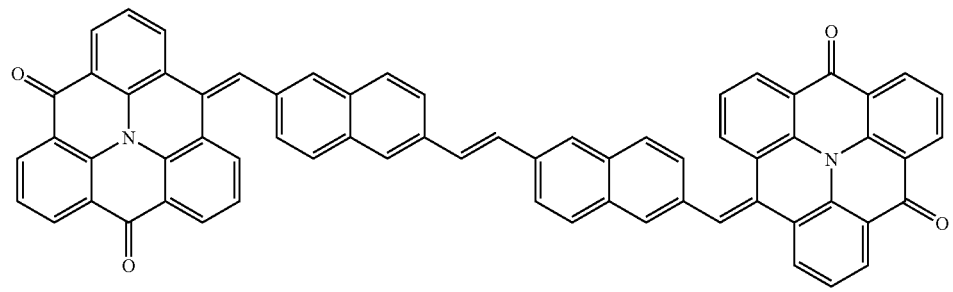
C48

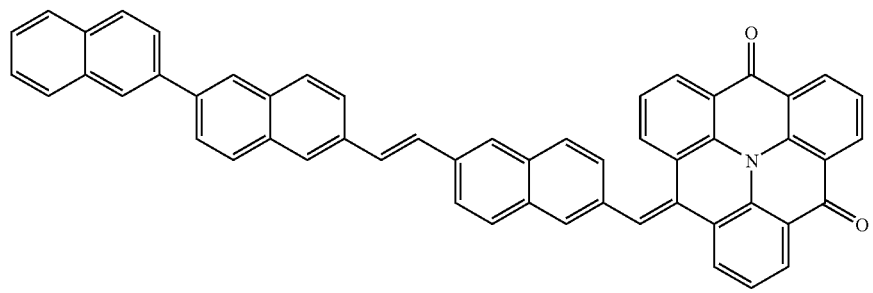
C49
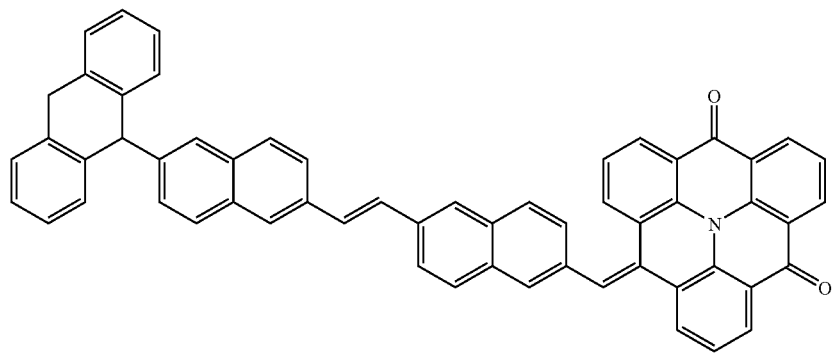
C50
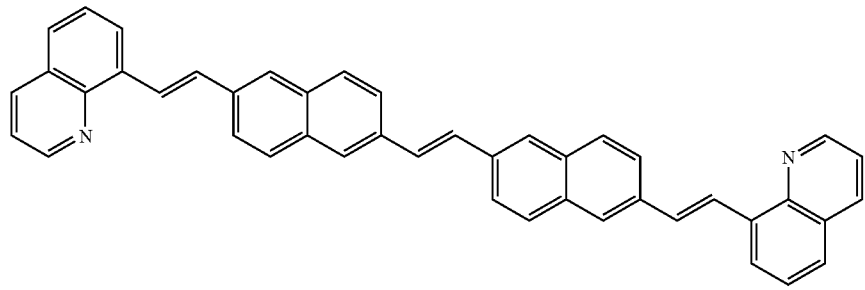
C51
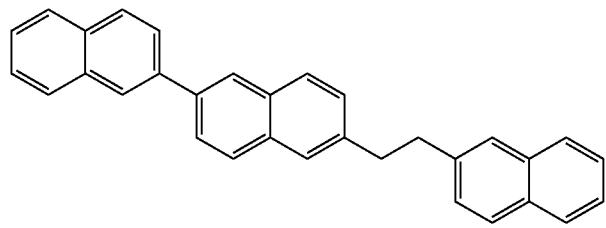
C52
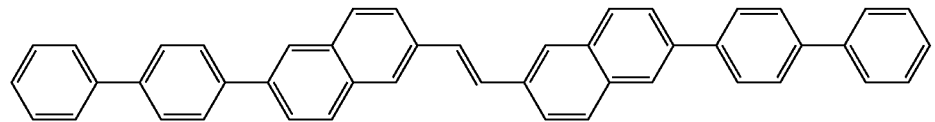
C53

C54
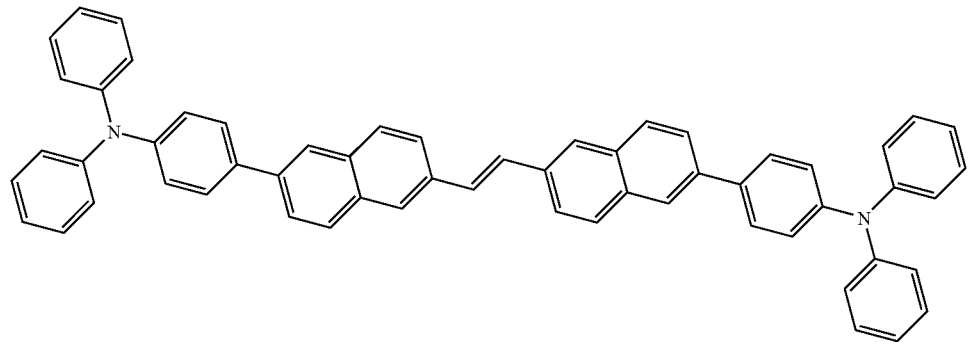
C55
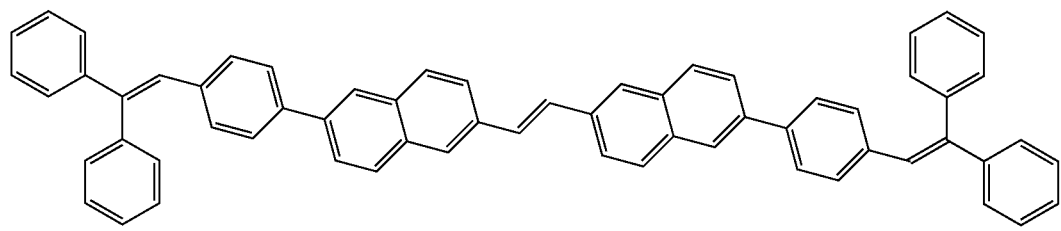
C56
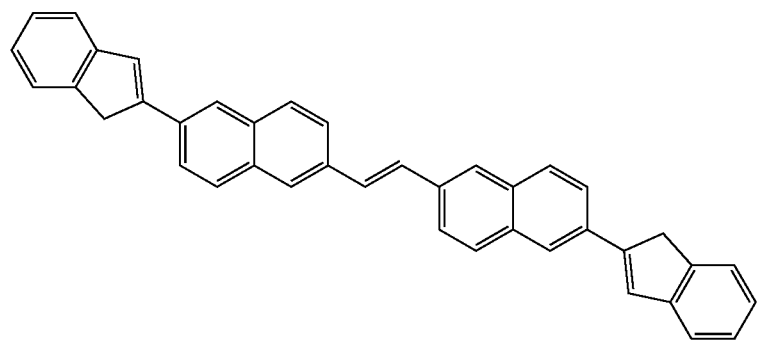
C57
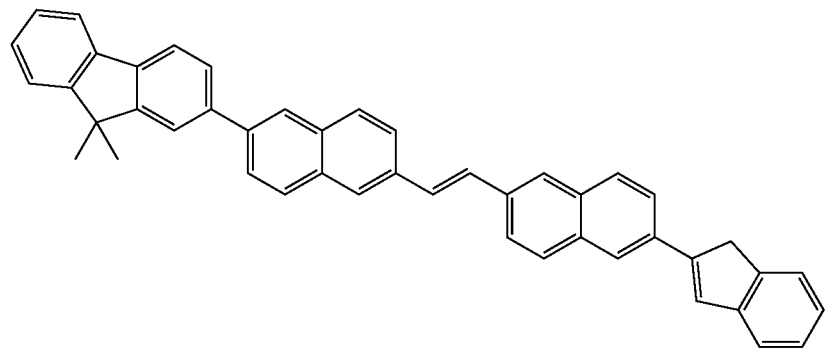

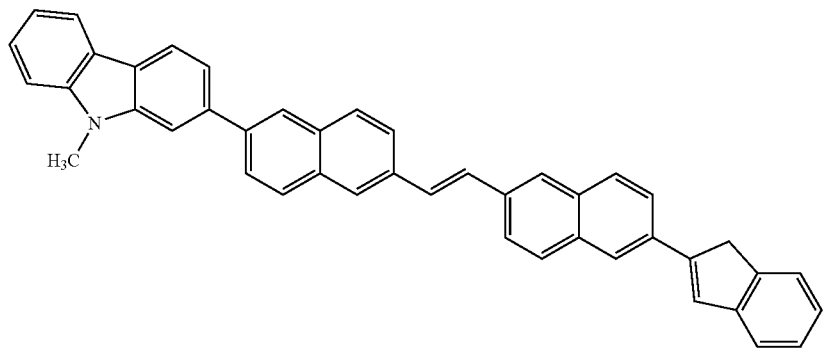
C58
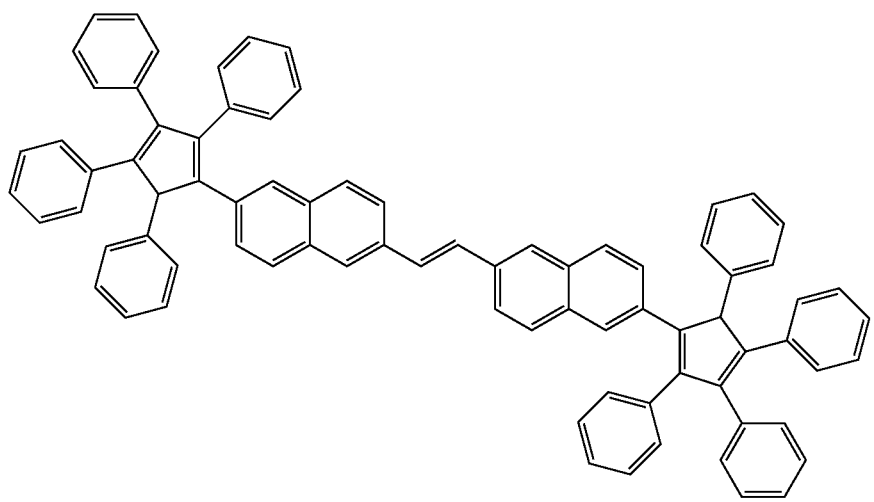
C59
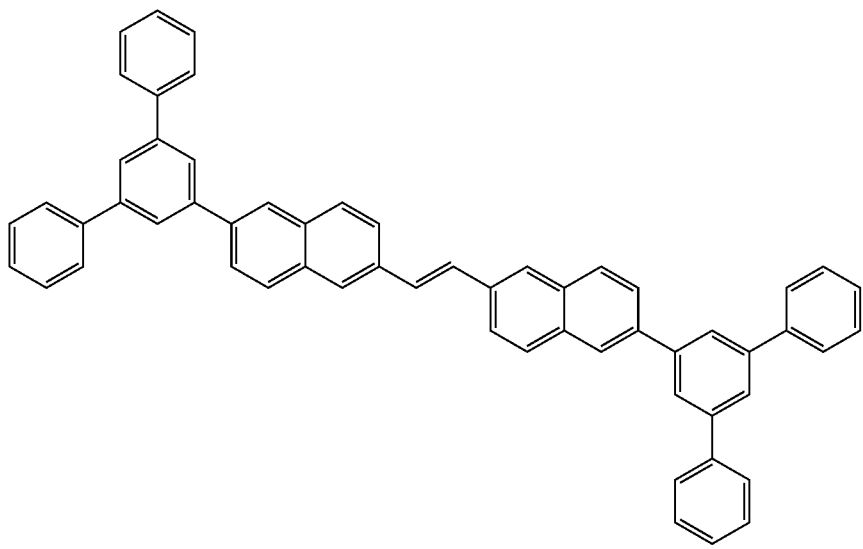
C60

-continued
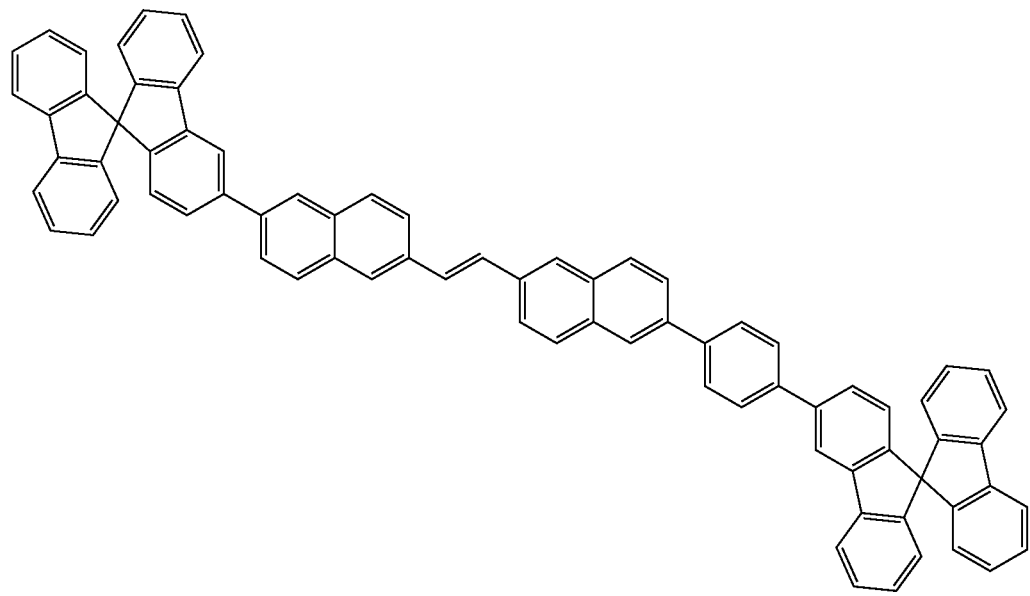
C61
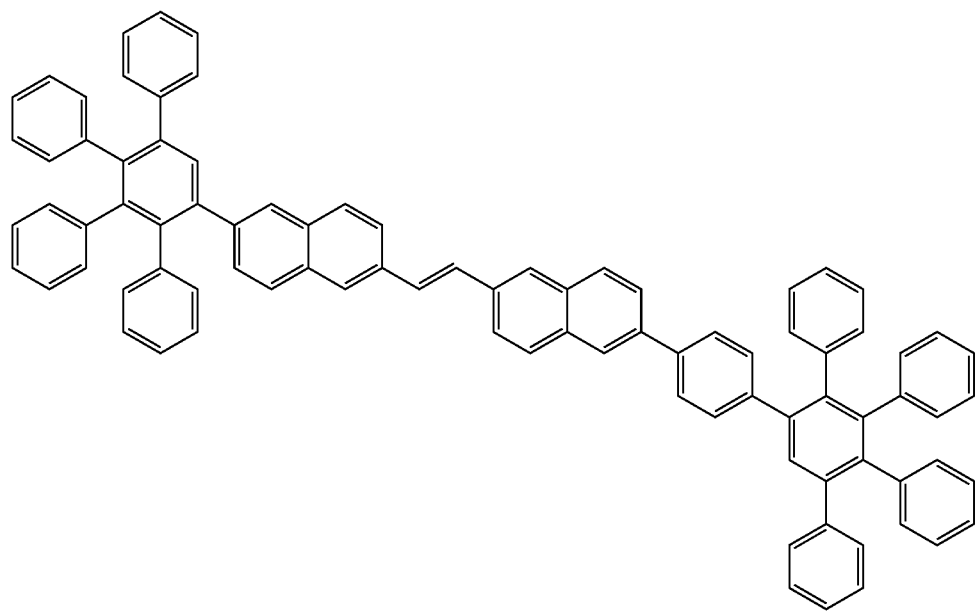
C62
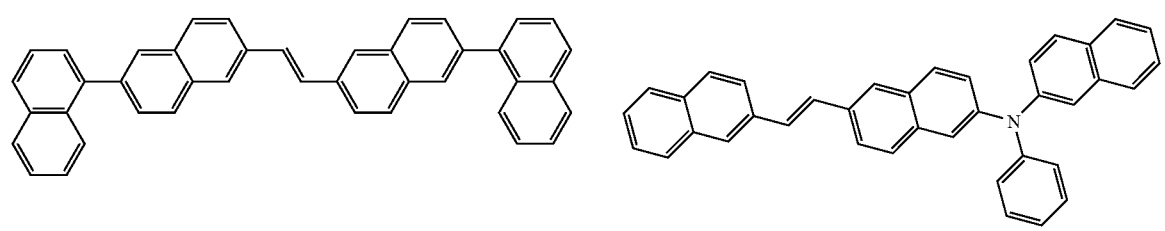
C63     C64

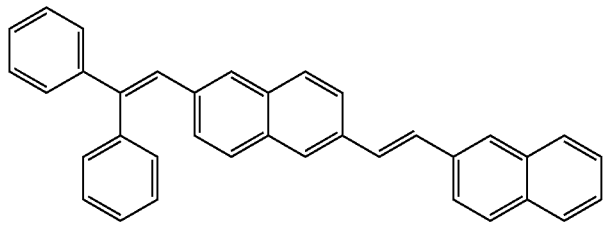
C65
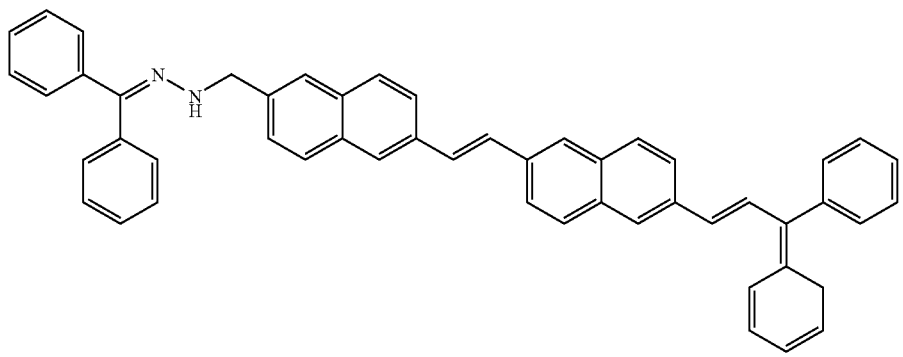
C66
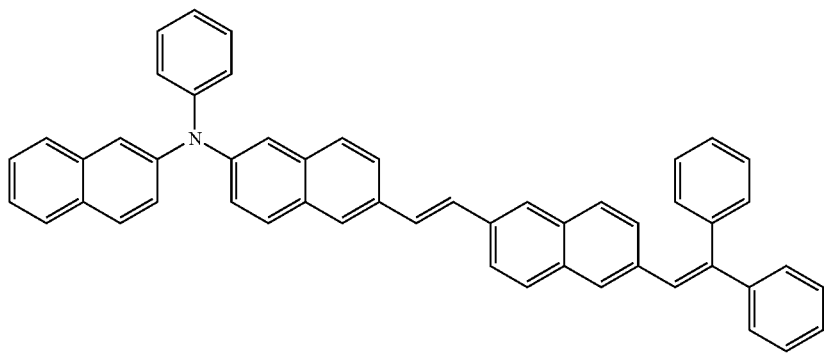
C67
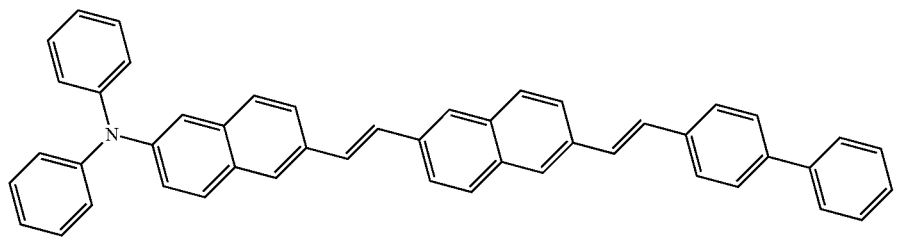
C68
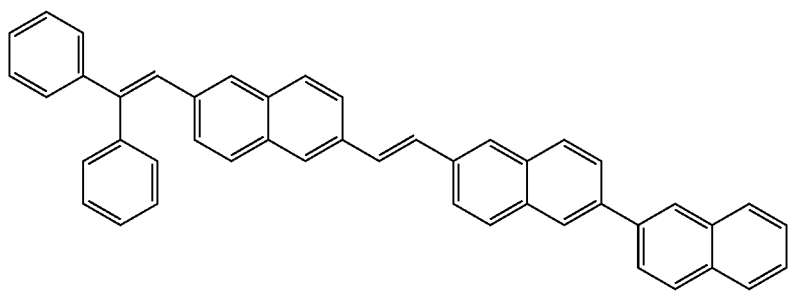
C69

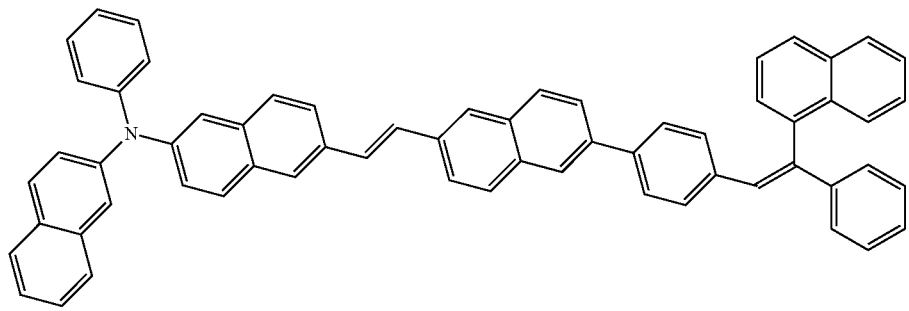
C70
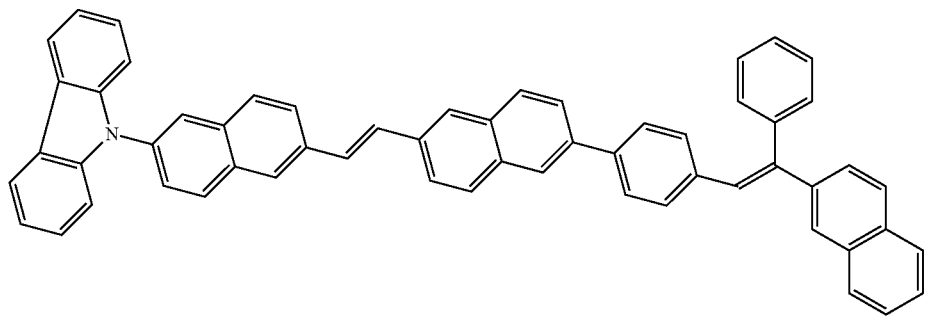
C71
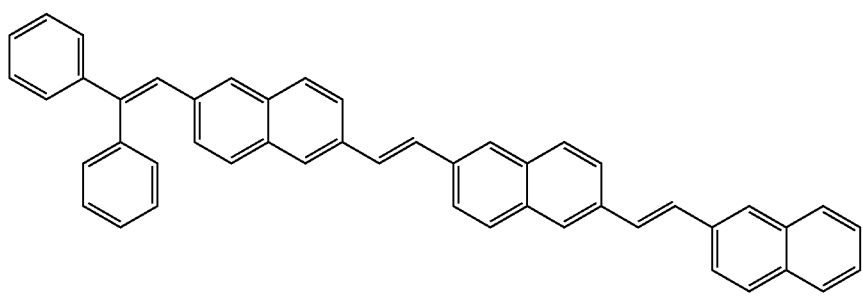
C72
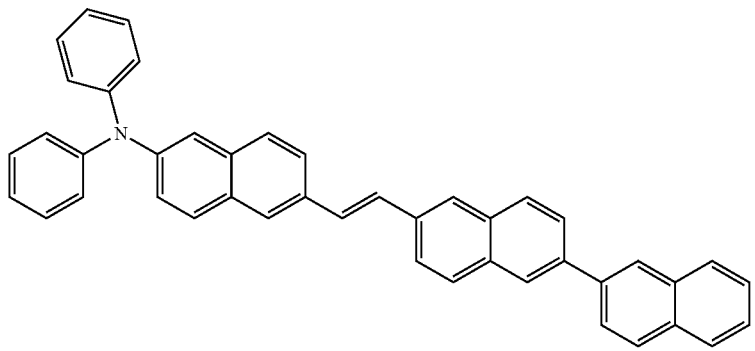
C73
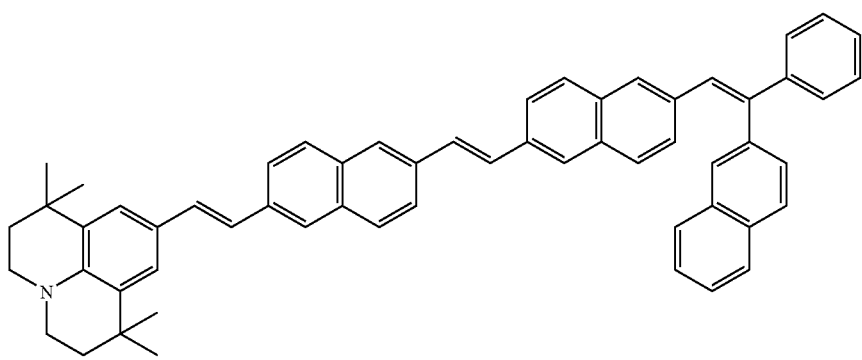
C74

-continued
C75
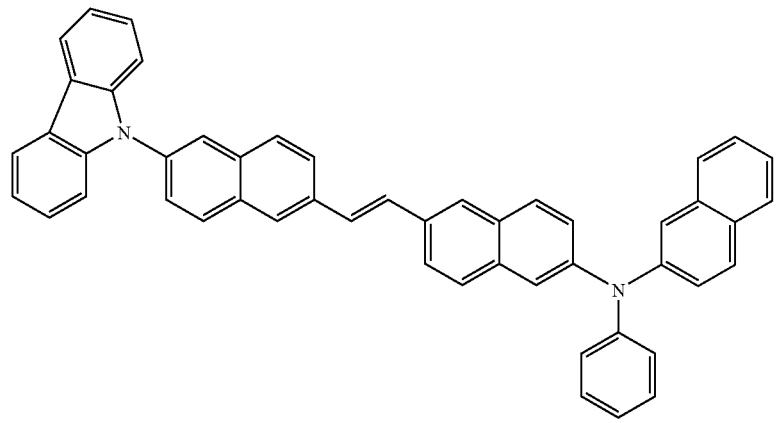
C76
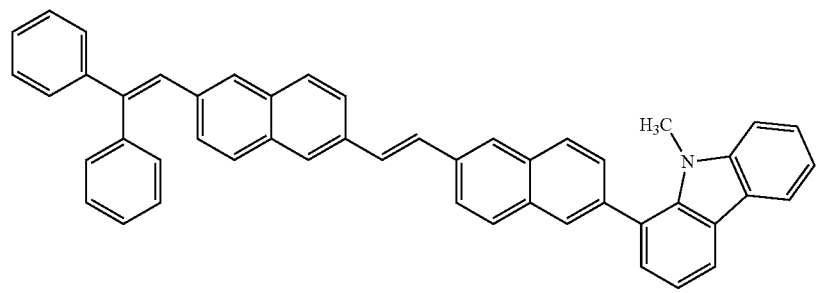
C77
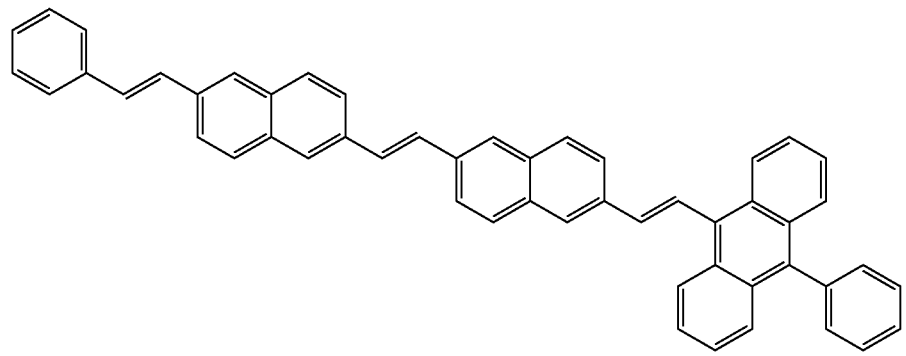
C78
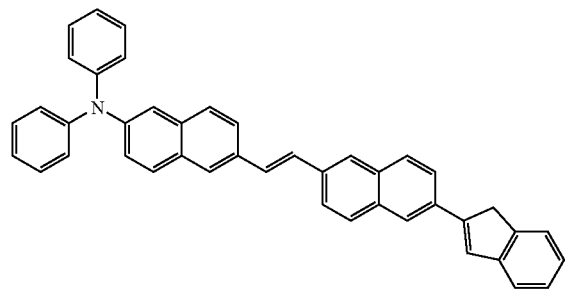
C79
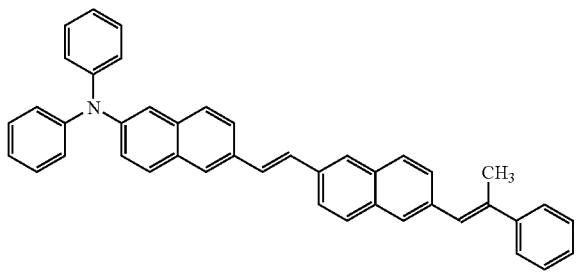

C80
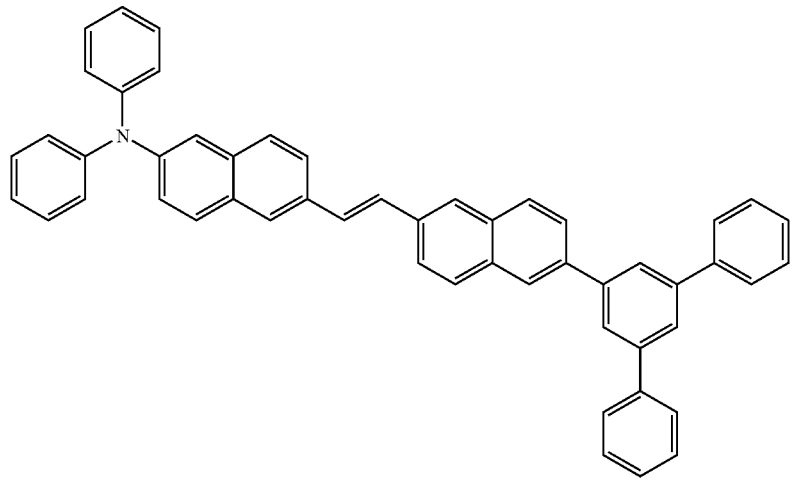
C81
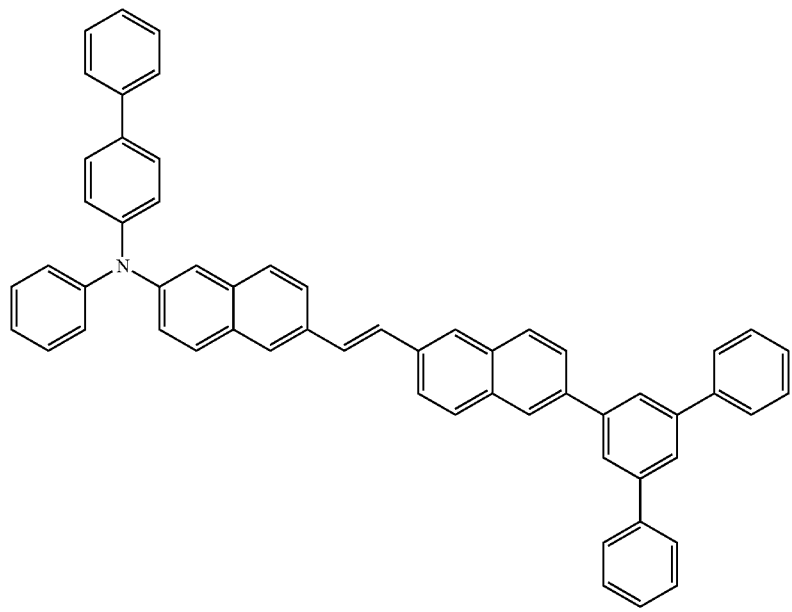
C82
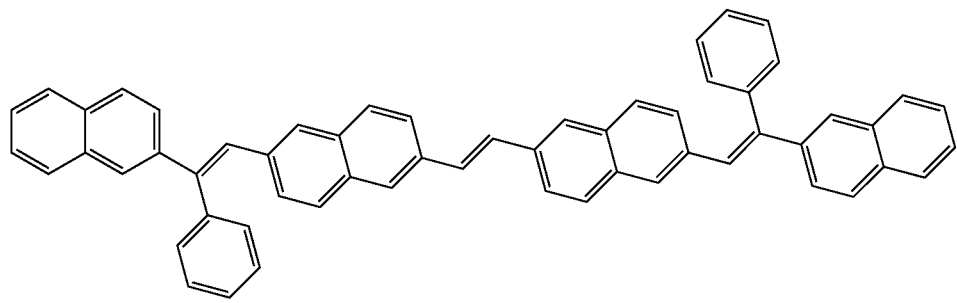
C83
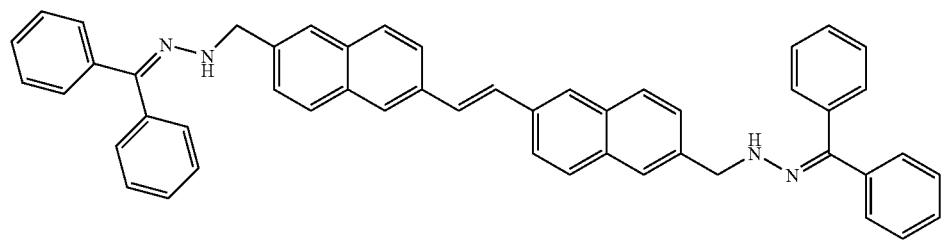

-continued
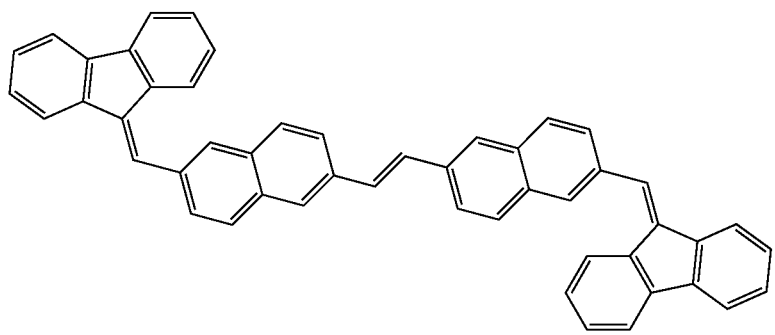
C84
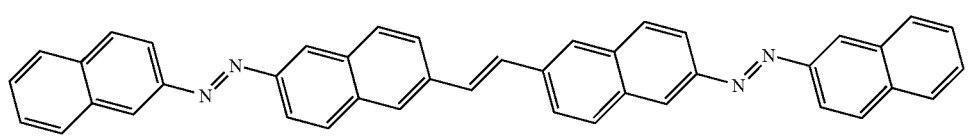
C85
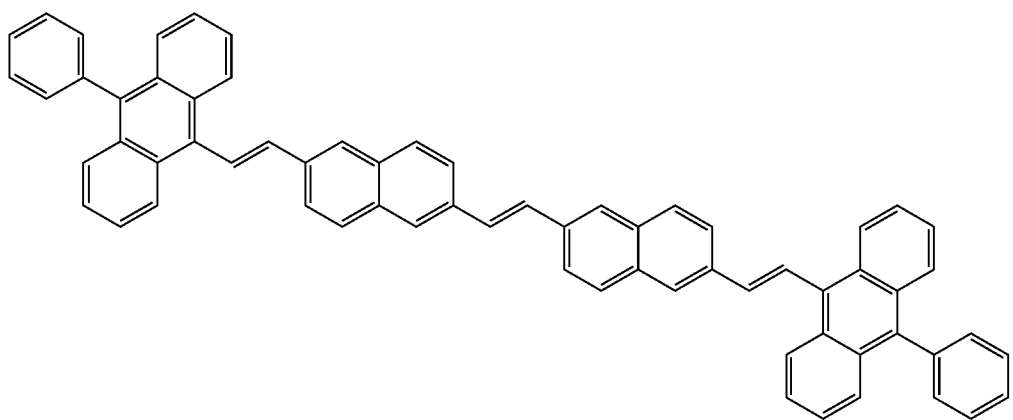
C86
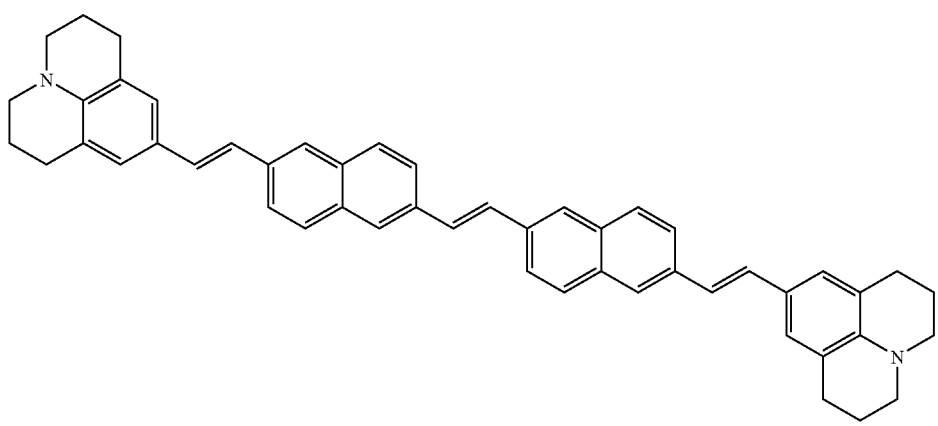
C87

C88
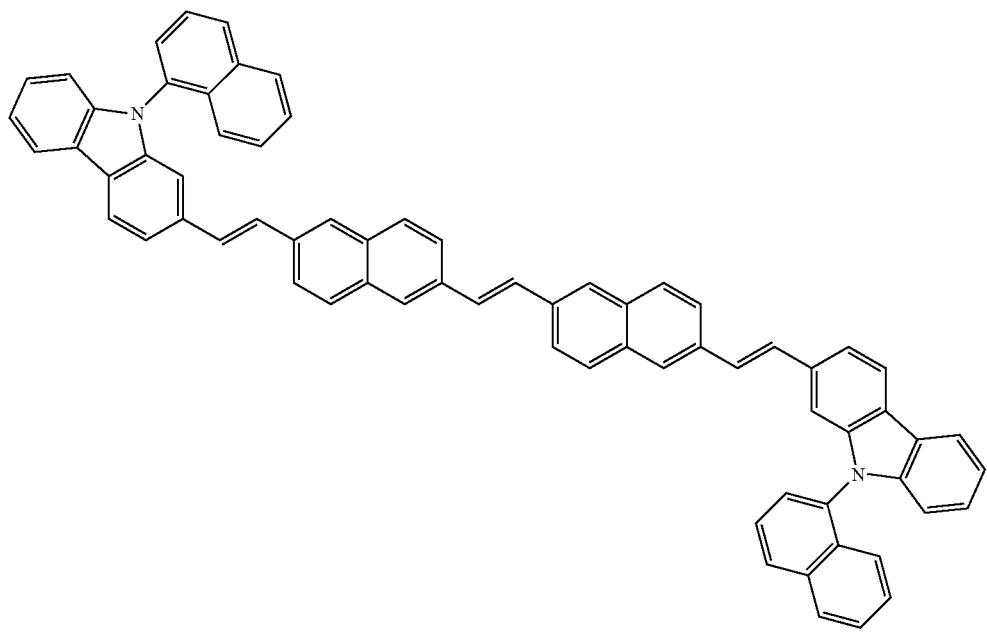
C89
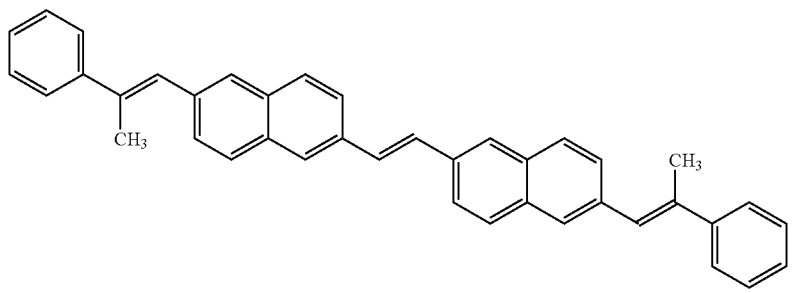
C90
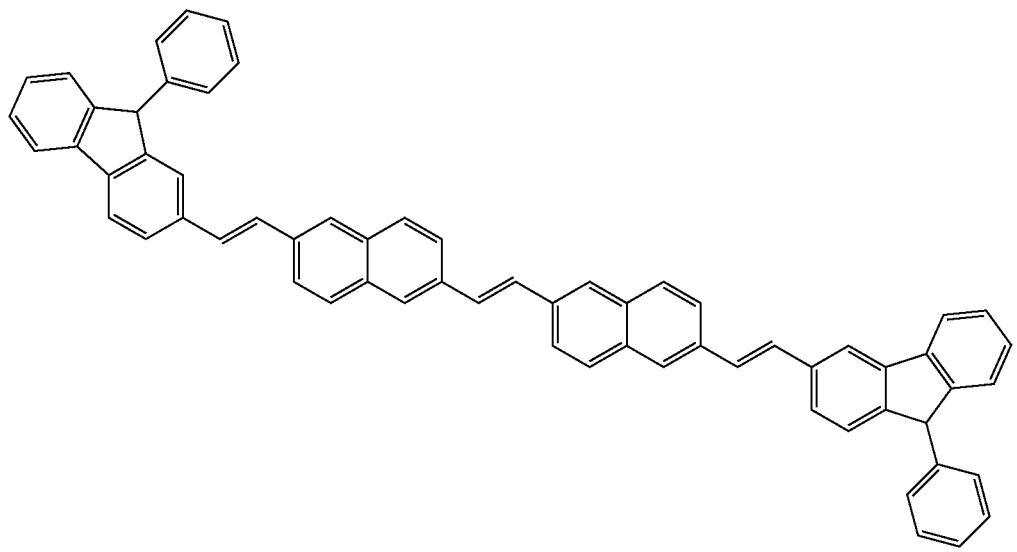

-continued
C91
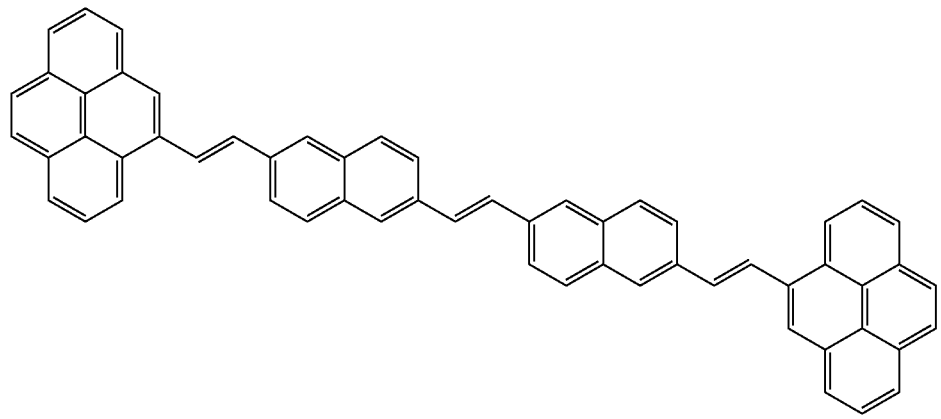
C92
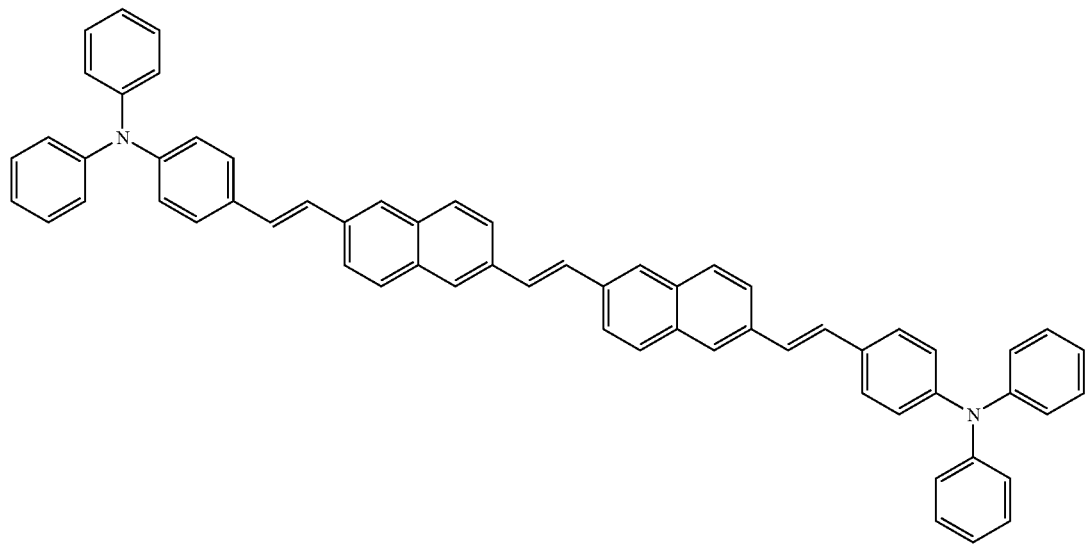
C93
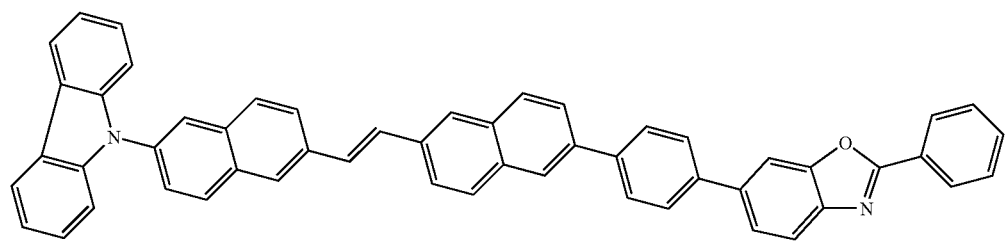
C94
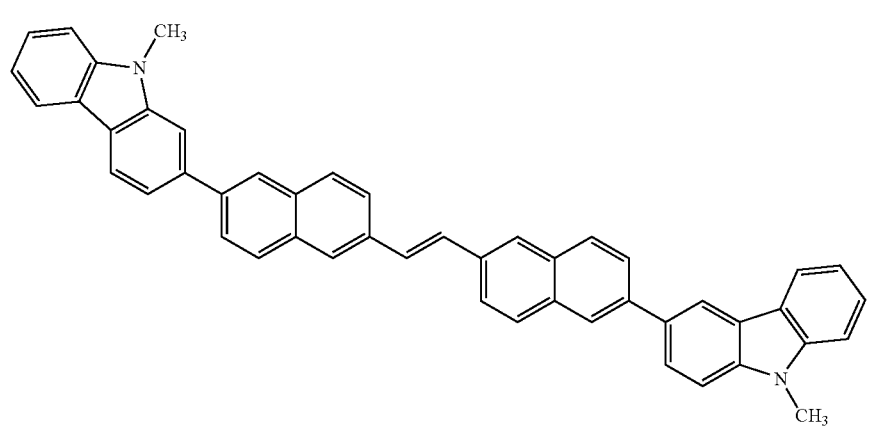

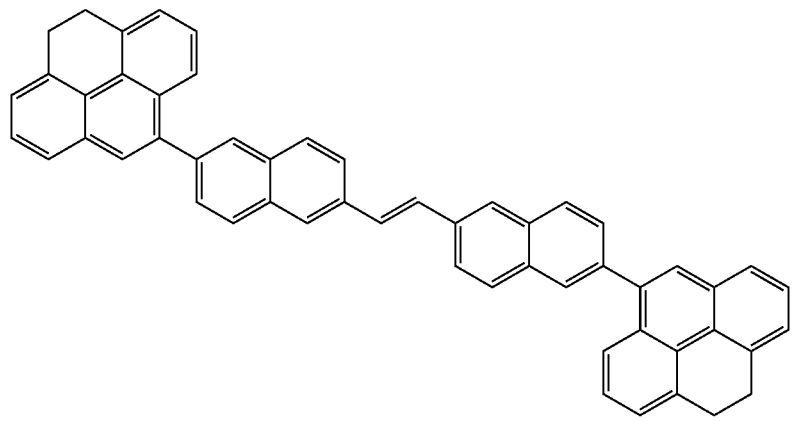

-continued
C100
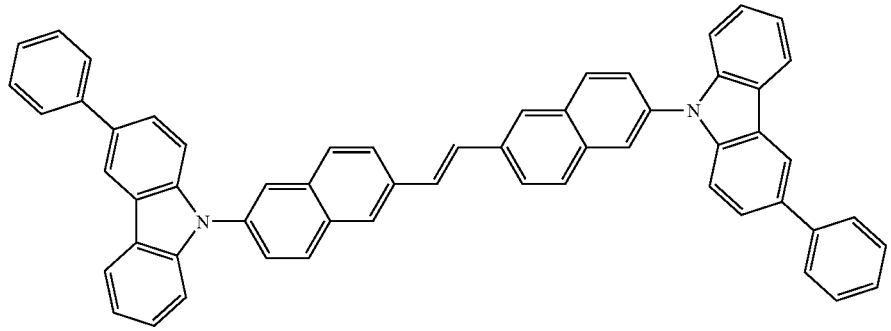
C101
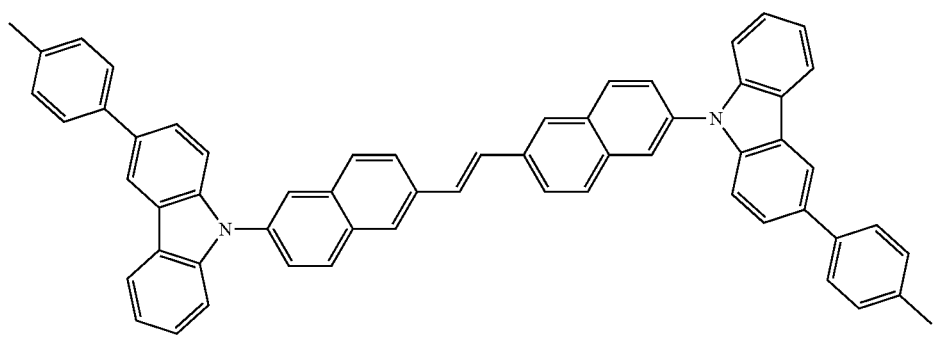
C102
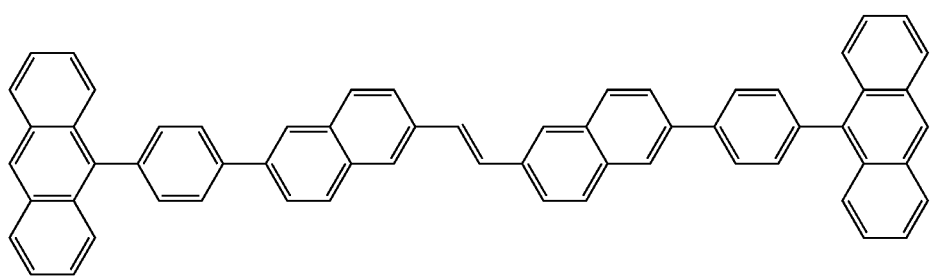
C103
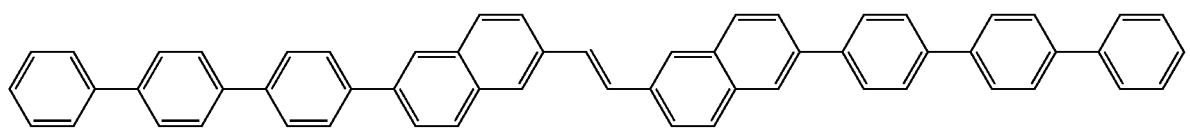
C104
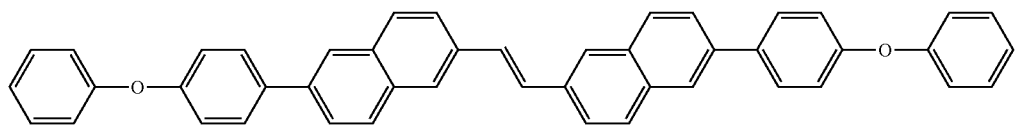
C105
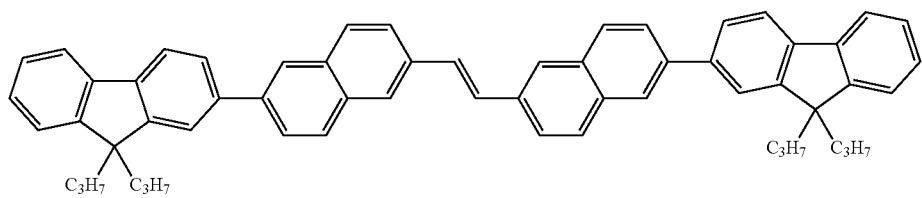

-continued
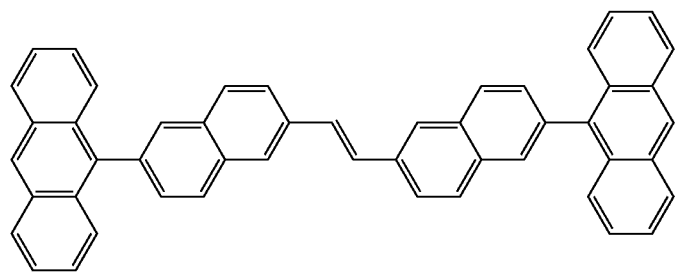
C106
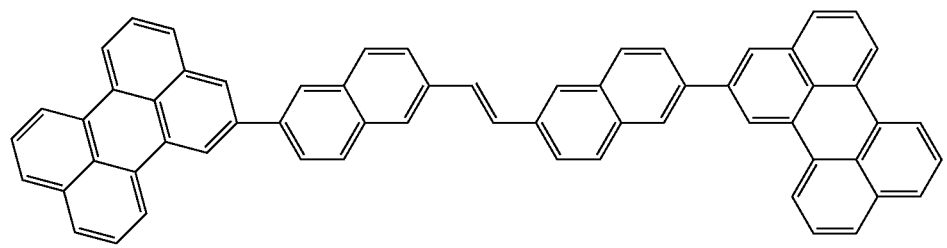
C107
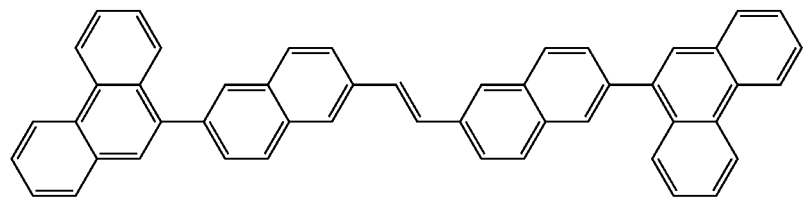
C108
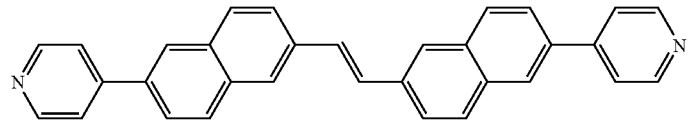
C109
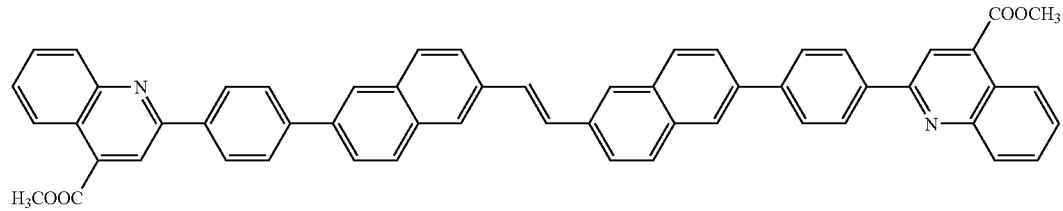
C110
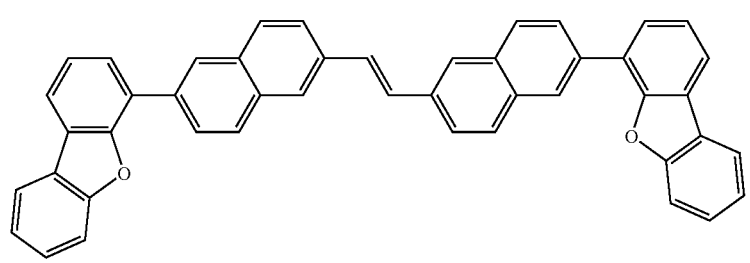
C111
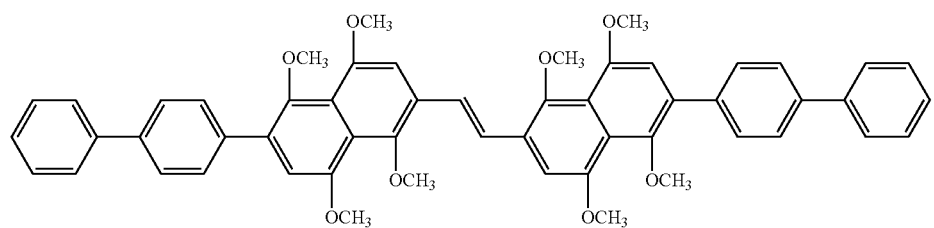
C112

C113
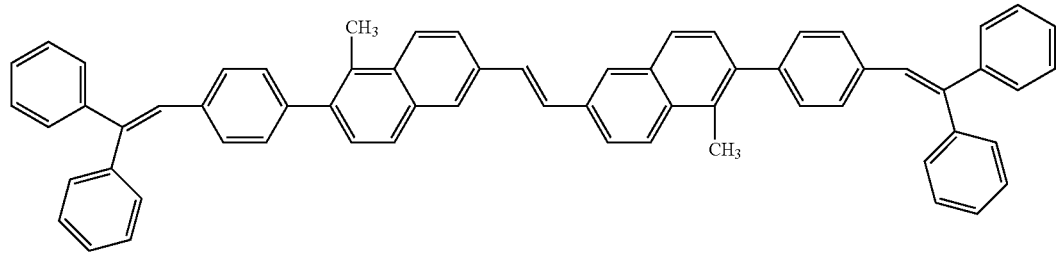
C114
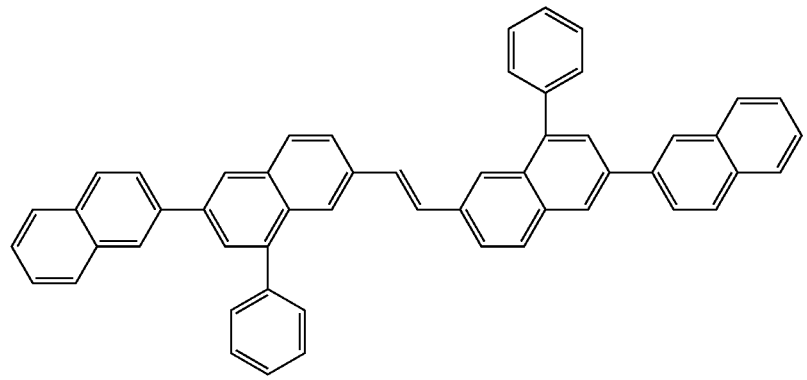
C115
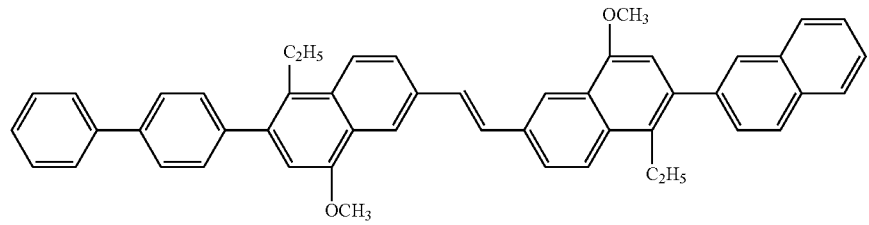
C116
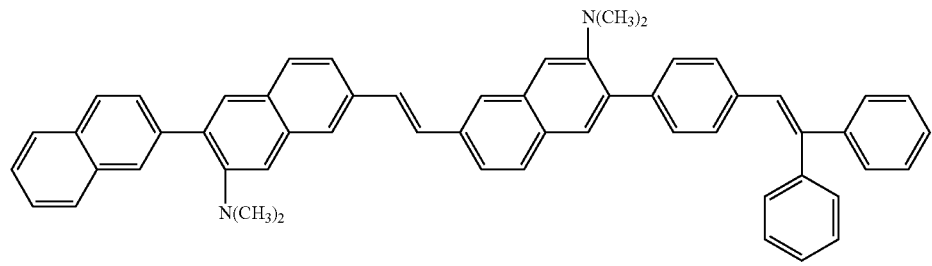
C117
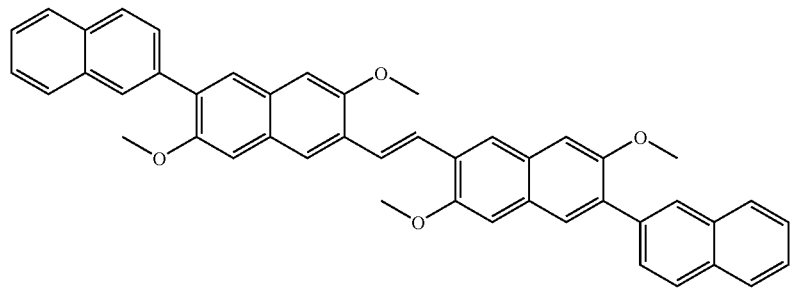

C118
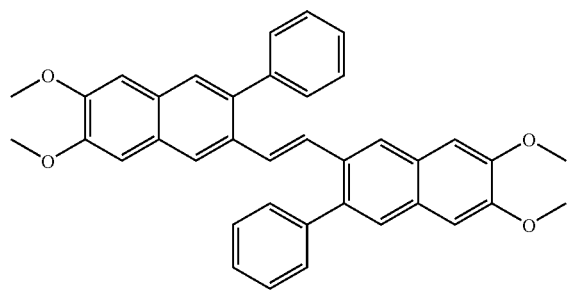
C119
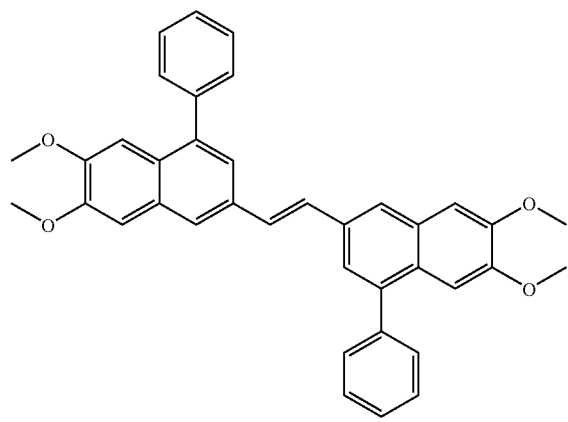
C120
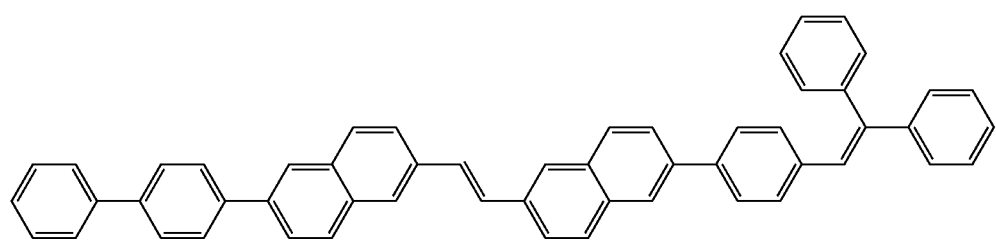
C121
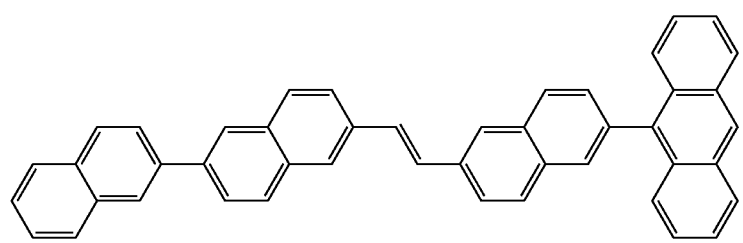
C122
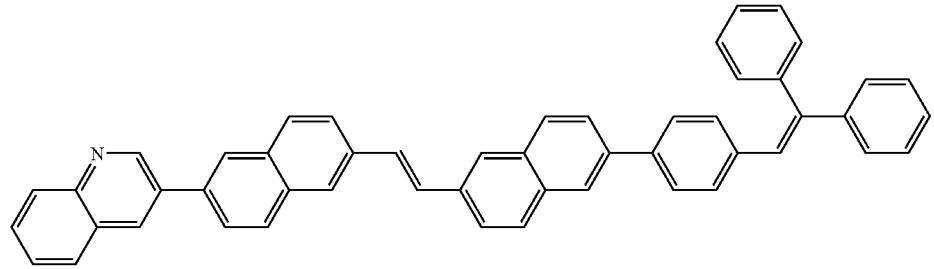
C123
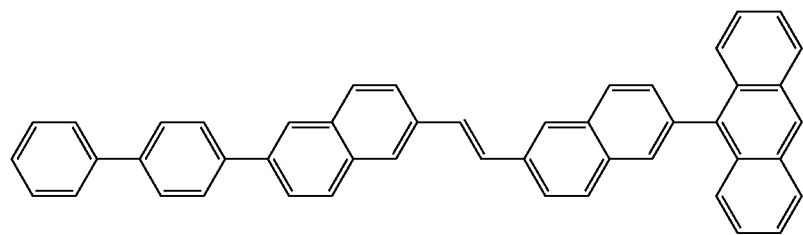
C124
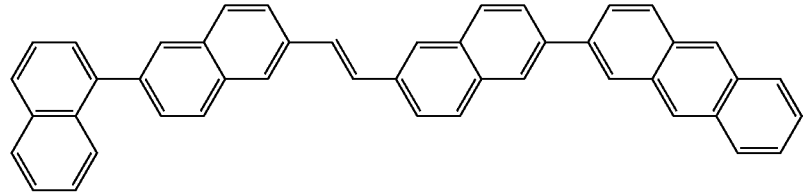

-continued
C125
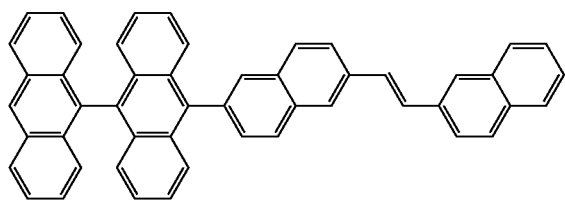
C126
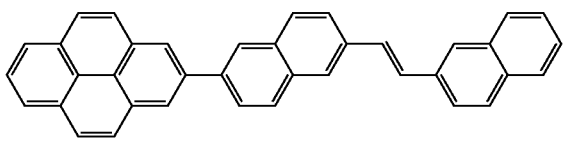
C127
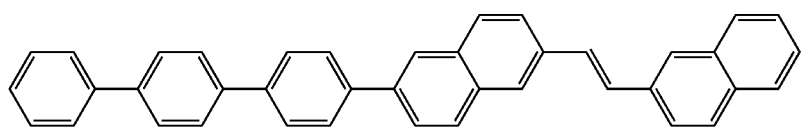
C128
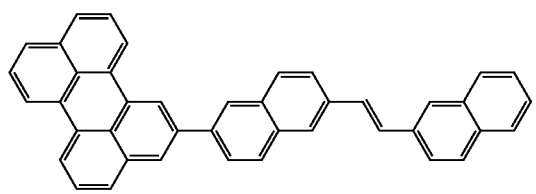
C129
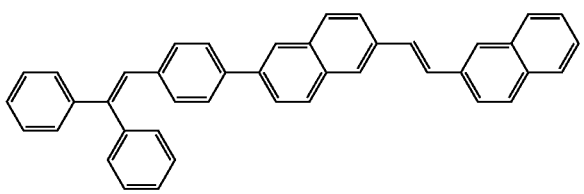
C130
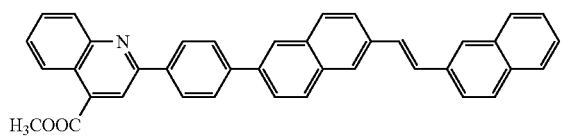
C131
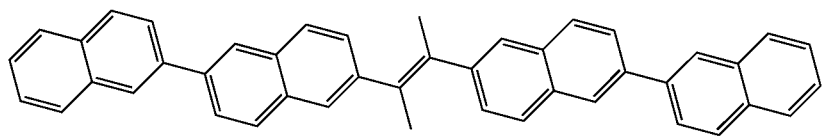
C132
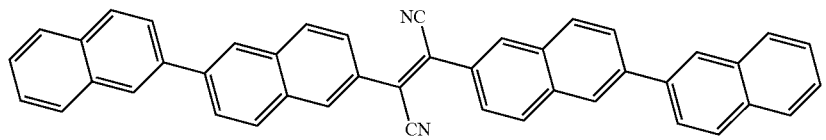
C133
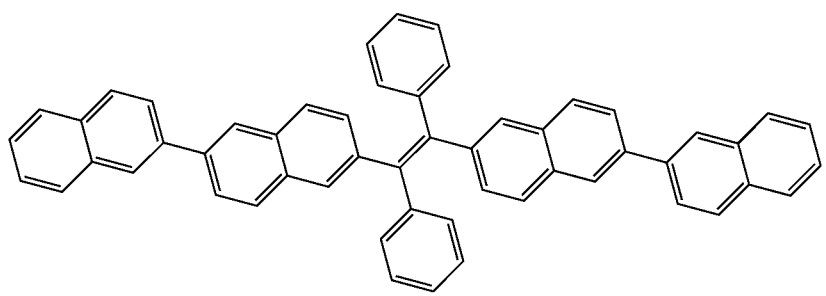
C134
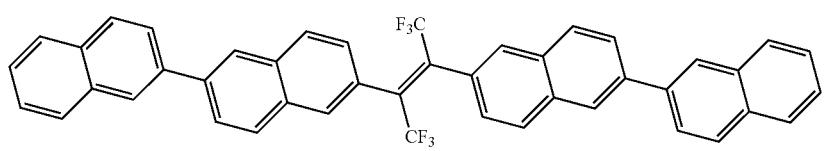

-continued
C135
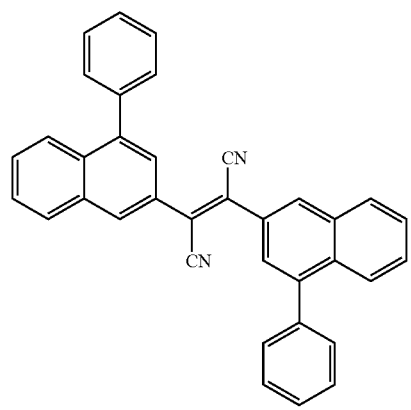
C136
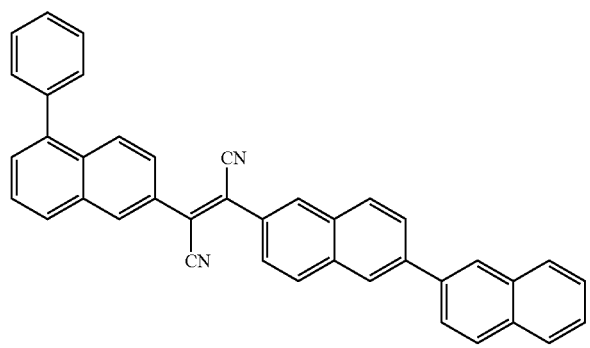
C137
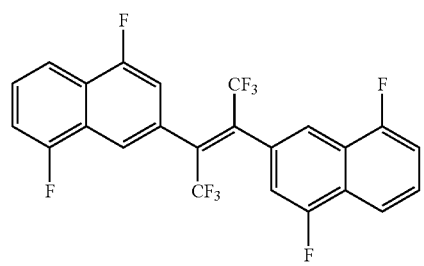
C138
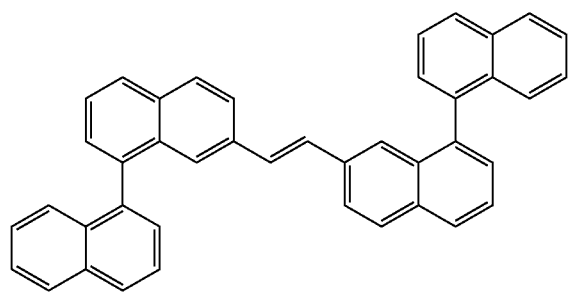
C139
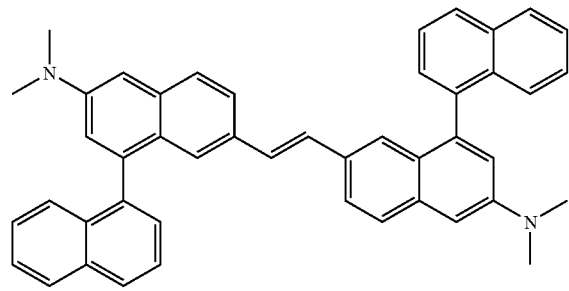
C140
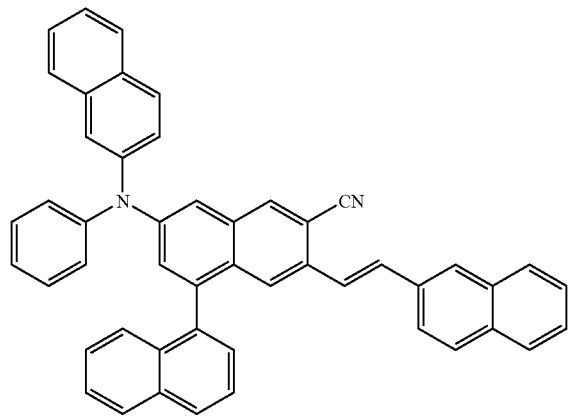
C141
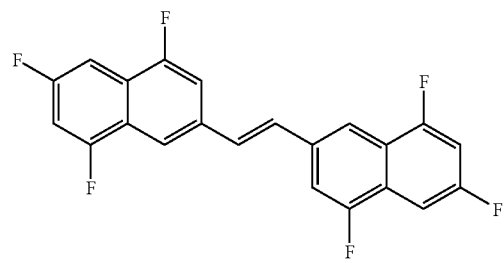

The dinaphthyl ethylene derivative represented by the above formula (I) can be prepared by one of the following processes a), b), c) and d):

a) reacting a compound of formula (I-a) with a compound of formula (I-b) in the presence of $TiCl_4$ and Zn, preferably Zn dust, in an inert solvent, preferably tetrahydrofuran, under an inert gas atmosphere, preferably Ar or $N_2$, and then optionally introducing the substituents where necessary;

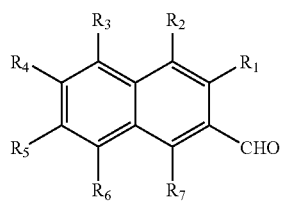
(I-a)

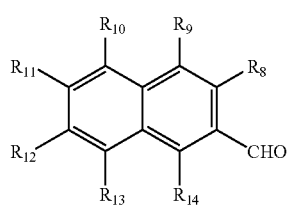
(I-b)

Wherein $R_1$-$R_{14}$ are defined as above;

b) reacting a compound of formula (I-a') with a compound of formula (I-b') in the presence of $TiCl_4$ and Zn, preferably Zn dust, in an inert solvent, preferably tetrahydrofuran, under an inert gas atmosphere, preferably Ar or $N_2$, and then optionally introducing the substituents where necessary;

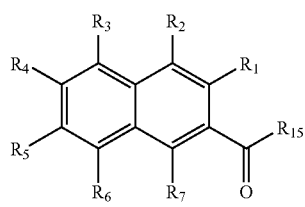
(I-a')

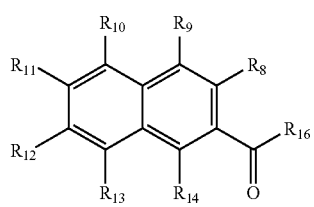
(I-b')

Wherein $R_1$-$R_{16}$ are defined as above;

c) reacting a compound selected from the group consisting of compounds of formula (I-a), formula (1-a'), formula (1-b) and formula (1-b') above with a compound of formula (I-c), in the presence of an alkali, preferably an alkali metal hydride, an alkali metal alcoholate, or an alkaline earth metal alcoholate, and especially sodium hydride, sodium ethylate, sodium methylate, sodium tertiary butoxide, or potassium tertiary butoxide, in an inert solvent, preferably tetrahydrofuran, and then optionally introducing the substituents where necessary;

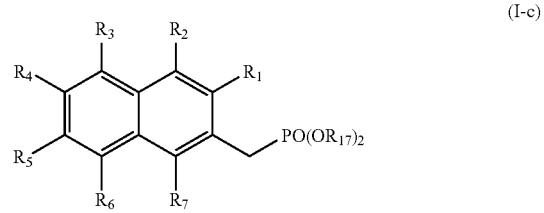
(I-c)

Wherein $R_1$-$R_7$ are defined as above, and $R_{17}$ is a linear or branched alkyl containing 1-6 carbon atoms, preferably a linear or branched alkyl containing 1-3 carbon atoms, and especially is a methyl or a ethyl; and d) reacting a compound of formula (I-d) with a compound of formula (I-e) in the presence of an alkali metal or alkali-earth metal alcoholate, preferably $NaOCH_3$, and $I_2$ in an inert solvent, preferably ethylene glycol dimethyl ether, and then optionally introducing the substituents where necessary.

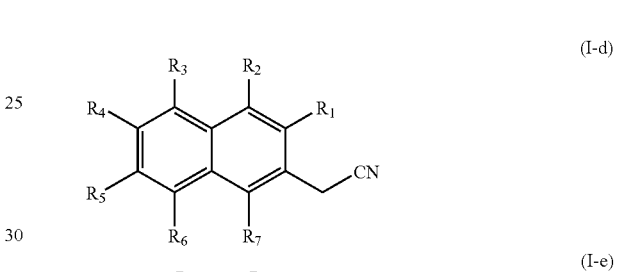
(I-d)

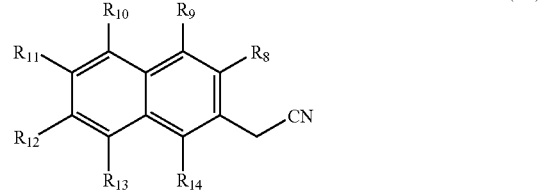
(I-e)

Wherein $R_1$-$R_{14}$ are defined as above.

The starting materials used in the process for preparing the compound of formula (I) are known in the art, or can be synthesized by a process known in the art, or can be synthesized by the process similar to that illustrated in the following examples.

The film according to the invention is prepared from the dinaphthyl ethylene derivative represented by the above formula (I) wherein the symbols are defined as above, said film useful in the manufacture of an OLED, the film is supported on a substrate and is deposited, by a known process, including evaporation or sputtering, on the substrate.

The OLED of the invention includes a film prepared from the dinaphthyl ethylene derivative represented by the above formula (I) wherein the symbols are defined as above.

The dinaphthyl ethylene derivative represented by the above formula (I) wherein the symbols are defined as above can be used in the manufacture of an OLED. This dinaphthyl ethylene derivative can use as host or dye in light-emitting layer as well as electron transporting layer or hole-blocking layer.

OLEDs including a film prepared from the dinaphthyl ethylene derivative of the present invention show excellent performances, such as high color purity and high luminescent efficiency.

It is to be understood that the foregoing statements, including the definitions of the substituents and the groups, in connection with the general description of the dinaphthyl ethylene derivative represented by the above formula (I), its preferred embodiment, further preferred embodiments, still further preferred embodiment, particularly preferred embodiments, the more particularly preferred embodiment and the specific compounds listed also apply in the process for preparing it, the film, the use, the OLEDs of the invention, and constitute the general description of the process for preparing it, the film, the use, the OLEDs of the invention, their respective preferred embodiments, further preferred embodiments, still further preferred embodiments, particularly preferred embodiments, the more particularly preferred embodiments and the specific embodiments.

The present invention will be described in more detail in the following examples. However, the examples are merely for illustration purpose and should not be considered as limiting the invention in any way. In the examples, unless indicated otherwise, the starting materials are commercially available.

Preparation of the Starting Materials

1. Preparations of the Aryl Substituted Boronic Acids

Synthesis of 4-biphenyl Boronic Acid

Synthesis scheme:

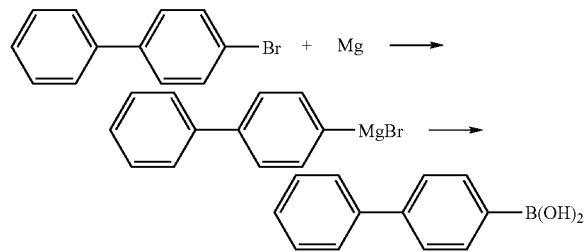

To a dry three-necked flask (100 ml) provided with a reflux condenser was added magnesium turnings (0.85 g, 0.035 mol), bromoethane (0.5 ml) and anhydrous THF (15 ml) under a flow of argon and with magnetic stirring. 4-bromobiphenyl (5.83 g, 0.025 mol) are dissolved in anhydrous THF (20 ml) and a portion of this solution (1.0 ml) was added to the reaction mixture. Reaction was initiated by warming, and then the remaining portion of the 4-bromobiphenyl solution was added to the reaction mixture over 10 minutes. The mixture was kept under reflux for 2 hours. The resulting Grignard reagent was cooled to −78° C. in an ethanol-liquid nitrogen bath, and then to it was added dropwise slowly fresh distilled trimethyl borate (3.25 ml, 0.03 mol). The cooling bath was removed and the mixture was stirred over night at room temperature. To the mixture was added hydrochloric acid solution (10%, 20 ml) slowly, and then stirring was continued for 30 minutes. The mixture was extracted with ether (50 ml×3). The organic layers were combined, washed with water until the washing solution was neutral, and dried over anhydrous magnesium sulphate. The organic phase was then filtered under reduced pressure and the solvent was removed to afford a sticky matter which was treated with petroleum ether (60 ml) to afford a offwhite powder, which was 4-biphenyl boronic acid (3.2 g).

Other aryl substituted boronic acids or aryl substituted dimethyl boronate were synthesized by a similarly process.

2. The Preparation of the Bromo-Substituted Naphthalene Derivates

Synthesis scheme:

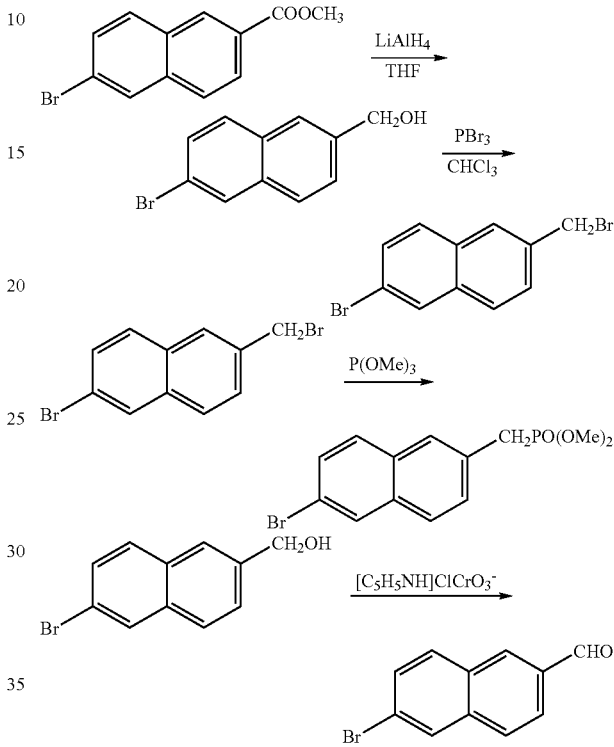

Synthesis of (6-bromonaphthalen-2-yl)methanol

To a three-necked flask (5 L) cooled with an ice-bath was added lithium aluminum hydride (40 g, 1.05 mol), and anhydrous THF (500 mL) under nitrogen protection. To this suspension, Methyl 6-bromo-2-naphthoate (141 g, 0.534 mol) dissolved in anhydrous THF (1200 mL) was added dropwise slowly through a dropping funnel. Cooling bath was removed and the reaction mixture was kept under stirring for additional 2 hours. The reaction mixture was cooled with an ice-bath again, and to it was added methanol (150 mL) dropwise carefully until there was no gas release. The mixture was kept under stirring for half an hour and then was acidified with concentrated hydrochloric acid to a PH of about 4. The resulting solid was removed by filtering under reduced pressure and the filtrate was concentrated, and then poured into deionized water (2 L). The resulting precipitate was collected by suction filter, and washed with deionized water, followed by a little ethanol, and dried in vacuum to afford (6-bromonaphthalen-2-yl)methanol (95.4 g).

Synthesis of 2-bromo-6-(bromomethyl)naphthalene

To a three-necked flask (2 L) was added (6-bromonaphthalen-2-yl)methanol (47.7 g, 0.201 mol) and chloroform (600 ml). The mixture was then cooled with an ethanol-liquid nitrogen bath to −35□. To the suspension was added phosphorus tribromide (28.6 ml, 0.603 mol) dropwise slowly over 25 minutes. The cooling bath was removed and the reaction mixture was kept under stirring for additional 2.5 hours at room temperature. The mixture was cooled again and to it was added methanol (250 mL) dropwise slowly and released quickly was hydrogen bromide, which was absorbed with a potassium hydrate solution. The mixture was warmed to room temperature and the resulting precipitate was collected by filtering under reduced pressure. The filter cake was washed with ethanol and dried to afford a white solid, 2-bromo-6-(bromomethyl)naphthalene (35 g).

Synthesis of dimethyl (6-bromonaphthalen-2-yl)methylphosphonate

To a three-necked flask (250 ml) was added 2-bromo-6-(bromomethyl)naphthalene (35.0 g, 0.117 mol) and trimethyl phosphite (18 mL, 0.152 mol). The reaction mixture was then heated to 150□ for 3 hours with a magnetic stirring. The redundant trimethyl phosphite was removed by vacuum distillation. The residue was cooled to room temperature to afford white solid. The solid was crushed to power, then washed with petroleum ether, collected by filtering under reduced pressure and finally dried in vacuum to afford a white solid (6-bromonaphthalen-2-yl)methylphosphonate (43 g).

Synthesis of 6-bromo-2-naphthaldehyde

To a three-necked flask (250 ml) was added (6-bromonaphthalen-2-yl)methanol (40.0 g, 0.170 mol) and dichloromethane (1.6 L) with magnetic stirring under nitrogen to form a clear solution. To this solution, Pyridinium chlorochromate (40.0 g, 0.186 mol) was added, and the resulting mixture turned black at once. Stirring was continued for 1 hour. The mixture was filtered through a short silica gel column, eluted with dichloromethane; the filtrate was dried over anhydrous magnesium sulphate, and then filtered under reduced pressure. The solvent was removed to afford a light brown solid, which was recrystallized from ethanol-water solution (50%) to afford a white solid 6-bromo-2-naphthaldehyde (31 g).

EXAMPLES FOR SYNTHESIZING THE COMPOUNDS OF THE PRESENT INVENTION

Example 1

Synthesis of Compound C1

Synthesis of Intermediate C1-1

To a three-necked flask (500 ml) was added 2-bromothiophene (16.30 g, 100 mmol), phenyl boronic acid (15.24 g, 125 mmol), Palladium (II) acetate (0.22 g, 1 mmol), triphenyl phosphine (0.53 g, 2 mmol), potassium carbonate (34.50 g, 250 mmol) and toluene (250 ml) under nitrogen with a magnetic stirring. The resulting mixture was heated under reflux for 4 hours, and then cooled to room temperature, and poured into a silica gel column (15 cm), eluted with petroleum ether. The solvent was removed by vacuum distillation to afford C1-1 (14.2 g).

Synthesis of Intermediate C1-2

To a three-necked flask (250 ml) was added 2-phenylthiophene (8.01 g, 50 mmol) and anhydrous THF (100 ml) under a flow of argon with magnetic stirring. The resulting mixture was cool to −78□ with an ethanol-liquid nitrogen bath. To this mixture was added n-BuLi solution in n-hexane (2.5M, 24 mL, 60.0 mmol) dropwise; then stirring was continued for 1.5 hours at −78□. Fresh distilled trimethyl borate (3.25 ml, 0.03 mol) was added dropwise slowly (8.5 ml, 75.6 mmol). The cooling bath was removed and the mixture was stirred overnight at room temperature. Hydrochloric acid (10%, 20 ml) was added to the mixture. The organic layer was separated, dried over anhydrous magnesium sulphate, and filtered. The solvent was removed from the filtrate by vacuum distillation. To the residue, petroleum ether was added and the precipitate was filtered under reduced pressure to afford a light green solid C1-2 (9.1 g).

Synthesis of Intermediate C1-3

The synthesis process for C1-1 was repeated, except that C1-2 and 6-bromo-2-naphthaldehyde were used instead of phenyl boronic acid and 2-bromothiophene respectively, affording C1-3 (4.2 g).

Synthesis of Compound C1

To a three-necked flask (100 ml) was added zinc dust (3.9 g, 60 mmol), and anhydrous THF (30 ml) under a flow of Synthesis scheme:

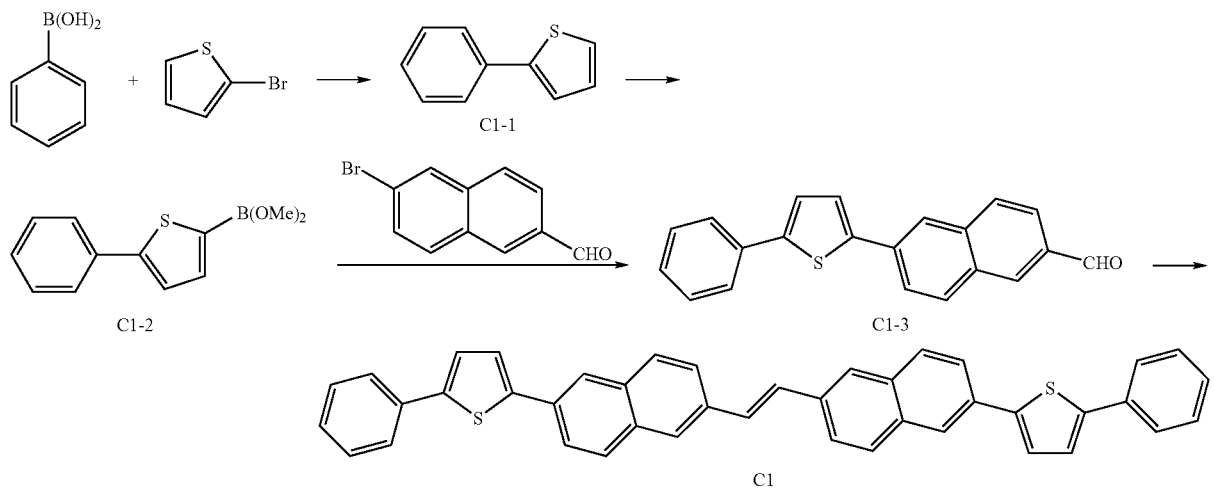

argon with magnetic stirring. The resulting mixture was cooled to −10□ with an ice-bath. To this cooled mixture, titanium tetrachloride (6.6 ml, 30 mmol) was added dropwise through a dry dropping funnel over 30 minutes; the resulting mixture was then heated under reflux for 2 hours, and then cooled. To this cooled mixture, C1-3 (3.14 g, 10 mmol) dissolved in anhydrous THF (30 ml) was added dropwise over 10 minutes, and the resulting mixture was heated under reflux overnight. The reaction mixture was cooled to room temperature, and filtered under reduced pressure. The filter cake was washed with THF (5 ml) to afford a green-yellow solid, which was then suspended in deionized water and the supernatant solid was filtered, dried in vacuum to afford compound C1 (2.8 g).

| | |
|---|---|
| MS (m/e) of compound C1: | 596; |
| Element analysis ($C_{48}H_{28}S_2$): | Calculated C: 84.53%, H: 4.73%, S: 10.75; Found C: 84.51%, H: 4.78%, S: 10.71%. |

Example 2

Synthesis of Compound C12

Synthesis of Intermediate C12-1

To a three-necked flask (250 ml) was added 2-bromoindole (7.00 g, 35.7 mmol), copper acetate (0.8 g, 4.8 mmol), 2,4-dimethylpyridine (2 mL), myristic acid (1.104 g, 4.8 mmol), phenyl boronic acid (5.8 g, 48 mmol) and toluene (100 mL) under a ambience of oxygen and then magnetic stirred for 24 hours. The mixture was filtered by a short silica gel column to remove the black mass, and the filtrate was evaporated under reduced pressure. The residue was crystallized from petroleum ether to afford a white crystal C12-1 (5.8 g).

Syntheses of C12-2, C12-3 and C12 the processes were the same as example 1, finally affording a yellow solid C12 (2.4 g).

| | |
|---|---|
| MS (m/e) of compound C: | 662; |
| Elemental analysis ($C_{50}H_{34}N_2$): | Calculated C: 90.59%, H: 5.13%, N: 4.22%; Found C: 90.60%, H: 5.17%, N: 4.23%. |

Synthesis scheme:

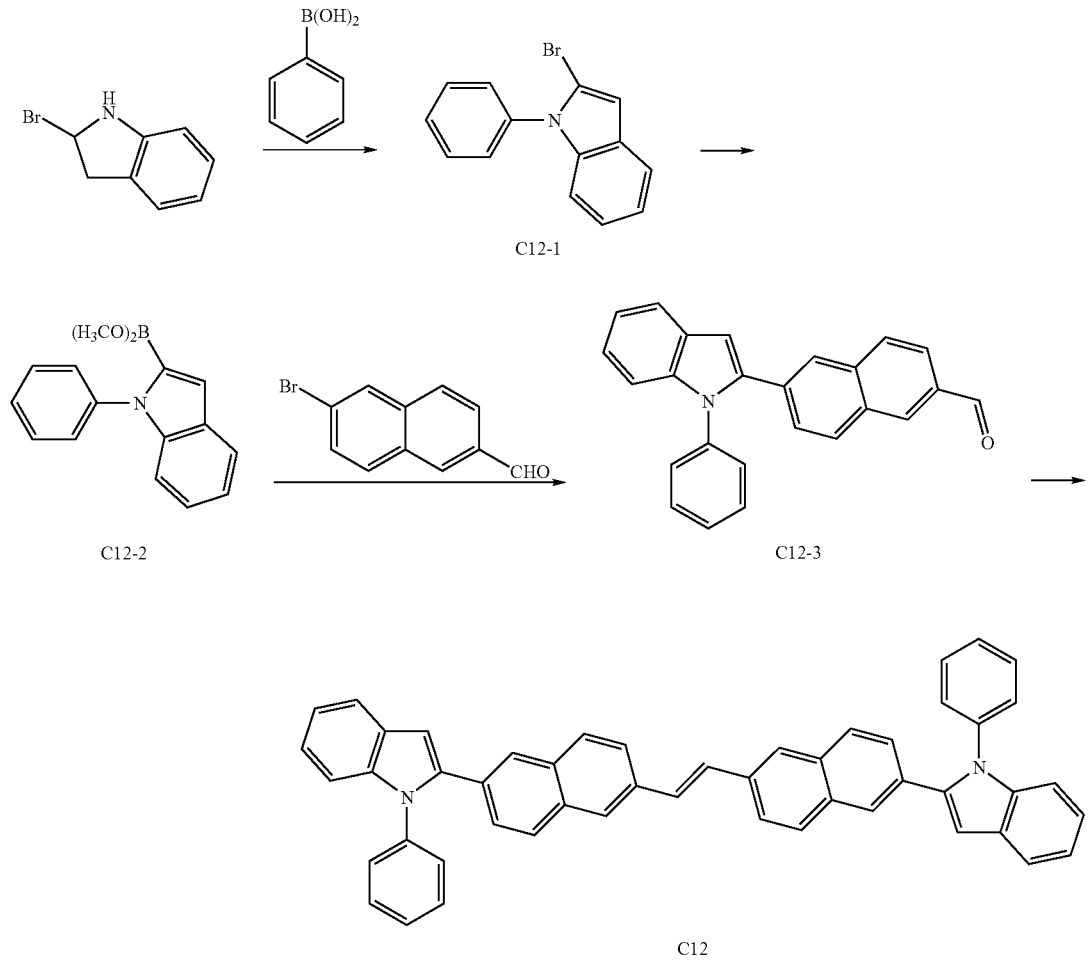

Example 3

Synthesis of Compound C19

Synthesis scheme:

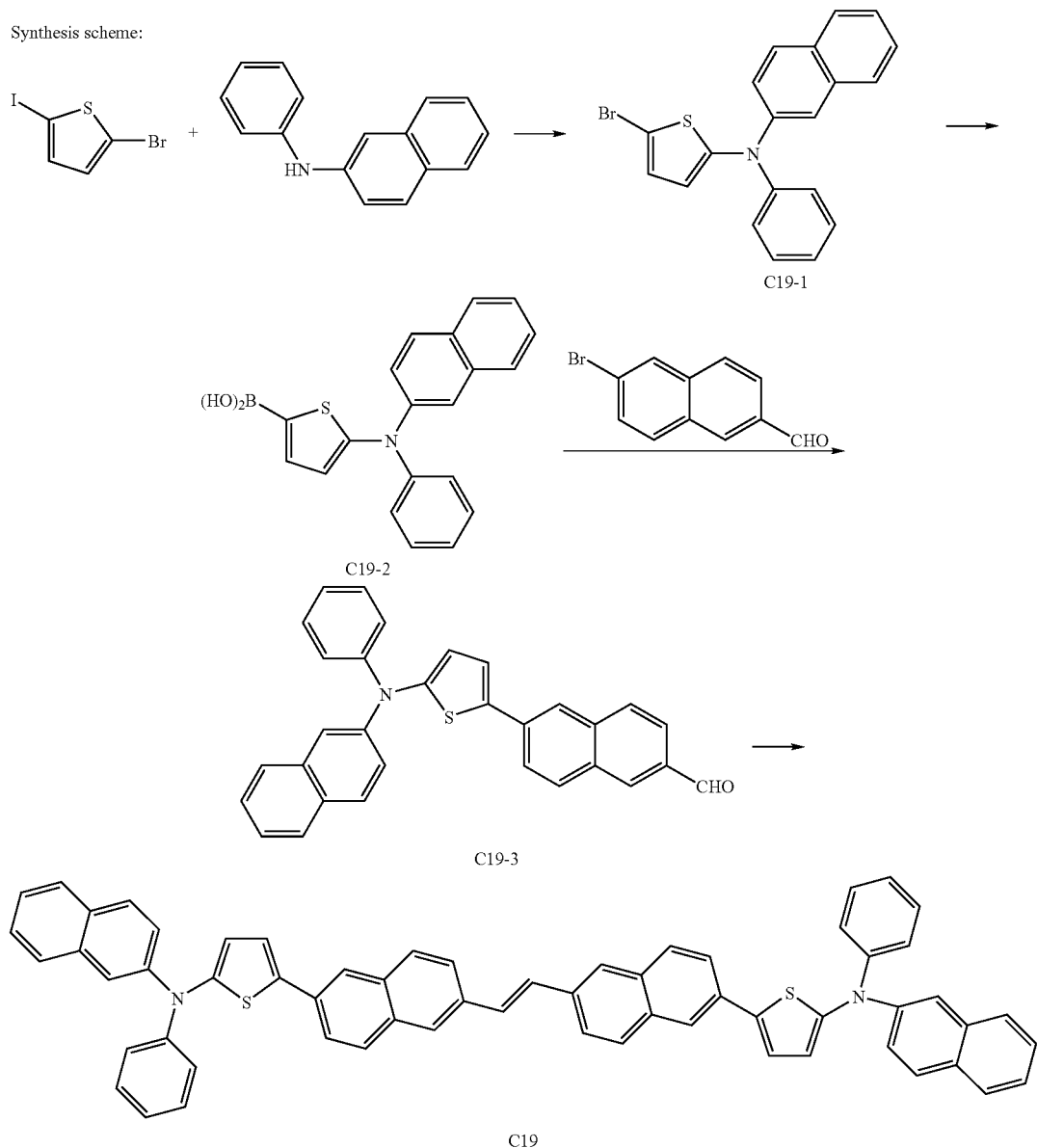

Synthesis of Intermediate C19-1

To a three-necked flask (500 ml) was added 2-bromo-5-iodothiophene (28.9 g, 100 mmol), N-phenyl-2-naphthalamine (24.1 g, 110 mmol), cuprous iodide (1.9 g, 10 mmol), anhydrous potassium phosphate (53 g, 200 mmol), and o-xylene (250 ml) under nitrogen protection and heated to reflux with magnetic stirring for 24 hour. The mixture was cooled to room temperature, and filtered under reduced pressure. The solvent was removed from the filtrate by vacuum distillation. The crude product was purified by a silica gel column, eluted with petroleum ether to afford C19-1 (19.6 g).

The following process was the same as example 1, to afford compound C19 (1.2 g).

| | |
|---|---|
| MS (m/e) of compound C: | 879; |
| Elemental analysis ($C_{62}H_{42}S_2N_2$): | Calculated C: 84.70%, H: 4.82%, S: 7.29, N: 3.19%; Found C: 84.71%, H: 4.78%, S: 7.31%, N: 3.20%. |

Example 4

Synthesis of Compound C32

Synthesis scheme:

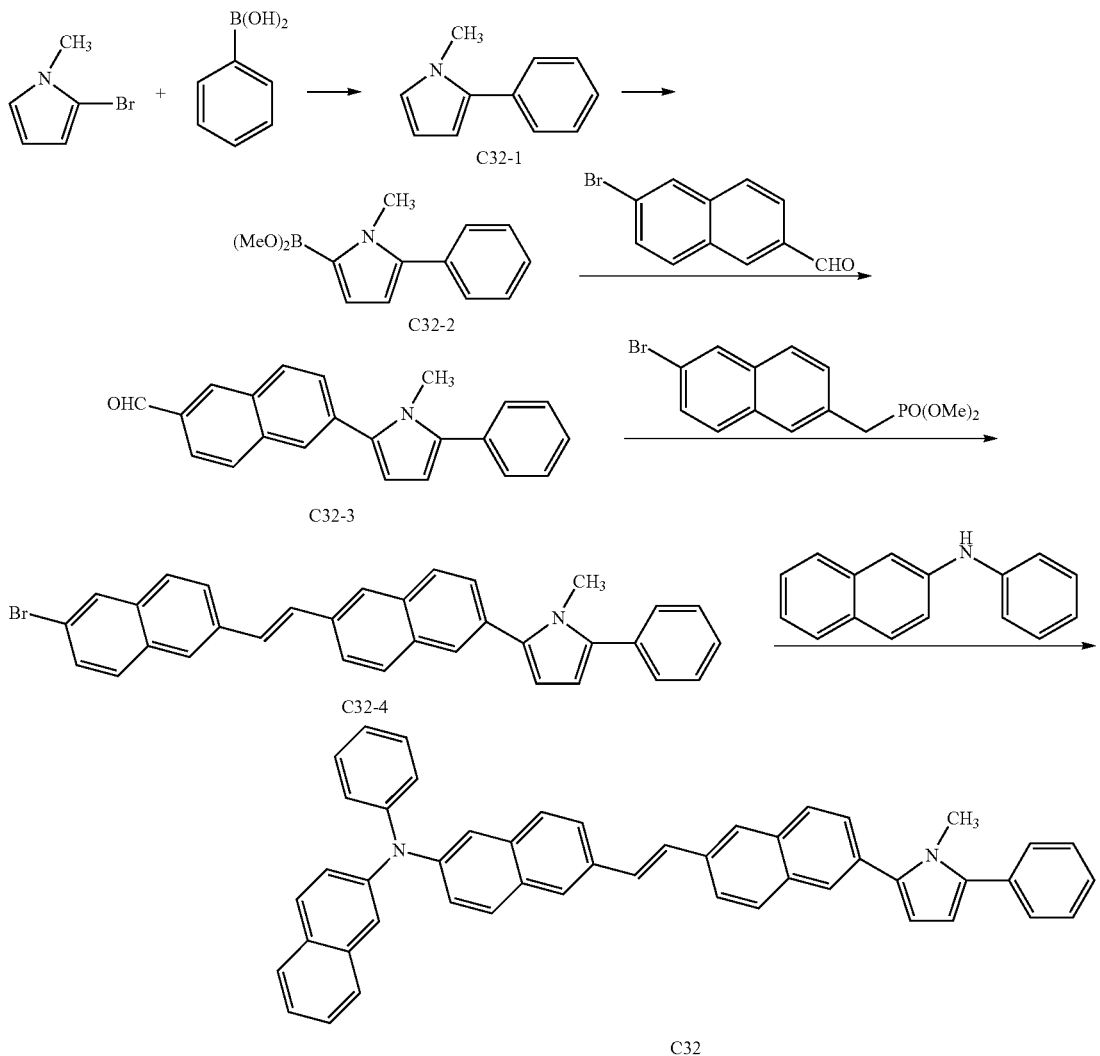

Synthesis of Intermediate C32-3

The process was the same as that for C1-3 (example 1), except that N-methyl-2-bromopyrrole was used instead of 2-bromothiophene.

Synthesis of Intermediate C32-4

To a three-necked flask (100 ml) was added C32-3 (6.22 g, 0.020 mol), dimethyl (6-bromonaphthalen-2-yl) methylphosphonate (7.24 g, 0.022 mol), sodium hydride (55% by weight, 1.28 g, 0.030 mol) and anhydrous THF (25 ml) under nitrogen. The resulting mixture was heated to reflux with a magnetic stirring for 15 hours. The mixture was cooled to room temperature and to it methanol (2 ml) was added carefully. The mixture was poured into water (50 ml), filtered under reduced pressure and the filtered cake was recrystallized from ethyl acetate to afford C32-4 (6.1 g).

Synthesis of Compound C32

To a three-necked flask (50 ml) was added C32-4 (5.14 g, 0.01 mol), Sodium tert-butoxide (2.87 g, 0.030 mol), N-phenyl-2-naphthalamine (2.4 g, 0.011 mol), Palladium (II) acetate (0.1 g, 0.5 mmol), triphenyl phosphine (0.26 g, 1 mmol) and anhydrous toluene (60 mL) under a flow of argon with magnetic stirring. The mixture was heated to reflux overnight. The mixture was cooled to room temperature, and filtered through a short silica gel column, eluted with toluene to removed the black mass and afford a sticky matter. The sticky matter was cooled to solidify, triturated to powder, dissolved in anhydrous ethanol and filtered to afford yellow powder C32 (5.52 g).

| | |
|---|---|
| MS (m/e) of compound C: | 652; |
| Elemental analysis ($C_{49}H_{36}N_2$): | Calculated C: 90.15%, H: 5.56%, N: 4.29%; Found C: 90.00%, H: 5.49%, N: 4.23%. |

Example 5

Synthesis of Compound C34

Synthesis scheme:

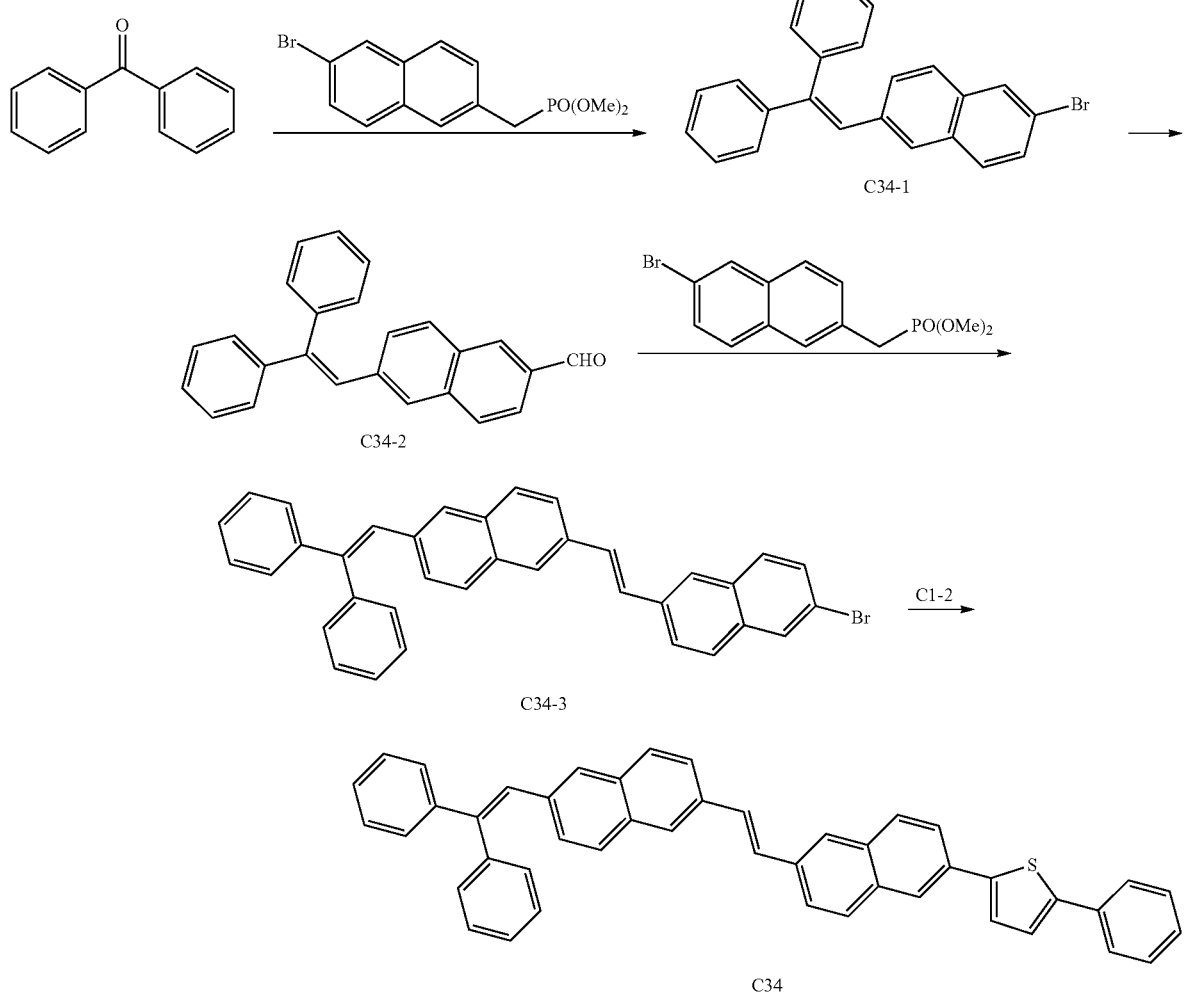

Synthesis of Intermediate C34-1

The process was the same as that for C32-4 (example 4), except that benzophenone was used instead of dimethyl (6-bromonaphthalen-2-yl)methylphosphonate to afford C34-1 (13 g).

Synthesis of Intermediate C34-2

To a three-necked flask (250 ml) was added C34-1 (7.71 g, 0.020 mol), tetramethylethylenediamine (5.3 ml, 0.040 mol) and anhydrous THF (60 mL) under a flow of argon with magnetic stirring. The mixture was cooled to −78□ in an ethanol-liquid nitrogen bath. To the mixture, an n-BuLi solution in n-hexane (2.5M, 16 ml, 0.040 mol) was added dropwise slowly to form a deep blue solution and then kept under continued stirring for 1 hour under −78□. Dimethyl formamide (15.1 ml, 0.2 mol) dissolved in THF (15 ml) was added dropwise slowly. The cool bath was removed and hydrochloric acid (10%, 55 mL) was added to the mixture at room temperature. The resulting reaction mixture was stirred for 1 hour. The mixture was extracted with ethyl acetate. The combined organic layers were dried over anhydrous magnesium sulphate and the solvent was removed under reduced pressure to afford a solid which was recrystallized from ethanol-ethyl acetate (V/V=2:1), to afford a light yellow solid C34-2 (6.7 g).

Synthesis of Compound C34

The process was the same as that for C1-3 (example 1), except that C34-2 was used instead of C1-2 to afford a yellow solid C34 (6.7 g).

| | |
|---|---|
| MS (m/e) of compound C: | 616; |
| Elemental analysis ($C_{46}H_{32}$): | Calculated C: 89.57%, H: 5.23%, S: 5.20%; Found C: 89.50%, H: 5.28%, S: 5.18%. |

Example 6

Synthesis of Compound C53

Synthesis scheme:

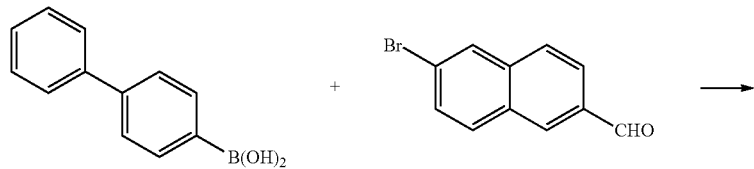

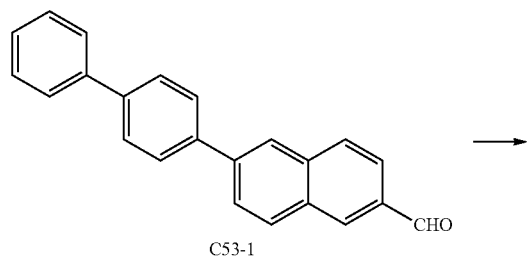

C53-1

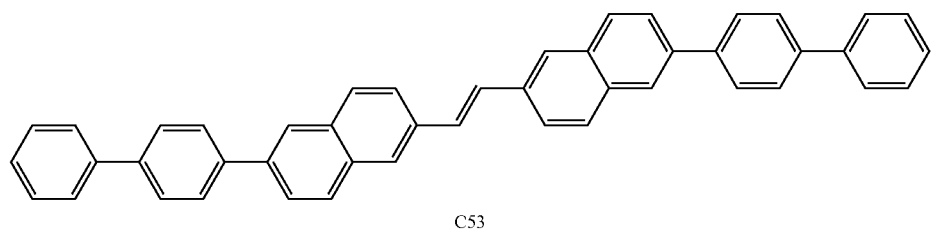

C53

The process was the same as example 1, except that 4-biphenyl boronic acid was used instead of C1-2 to afford compound C53 (3.8 g).

| MS (m/e) of compound C: | 584; |
|---|---|
| Elemental analysis ($C_{46}H_{32}$): | Calculated C: 94.48%, H: 5.52%; Found C: 94.41%, H: 5.58%. |

Example 7

Synthesis of Compound C55

The process was the same as example 6, except that 4-(2',2'-diphenylvinyl)phenyl boronic acid was used instead of 4-biphenylboronic acid, to afford a yellow powder C55.

| MS (m/e) of compound C: | 788; |
|---|---|
| Elemental analysis ($C_{62}H_{44}$): | Calculated C: 94.38%, H: 5.62%; Found C: 94.41%, H: 5.60%. |

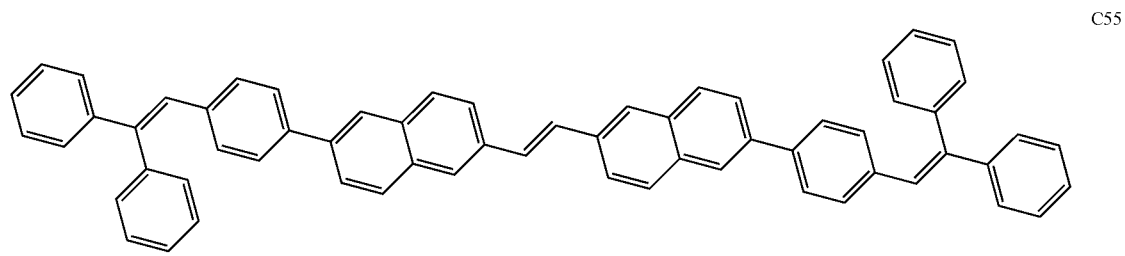 [SMILES: C(=C(c1ccccc1)c1ccccc1)c1ccc(-c2ccc3cc(/C=C/c4ccc5cc(-c6ccc(C=C(c7ccccc7)c7ccccc7)cc6)ccc5c4)ccc3c2)cc1]

C55

Example 8

Synthesis of Compound C60

Synthesis scheme:

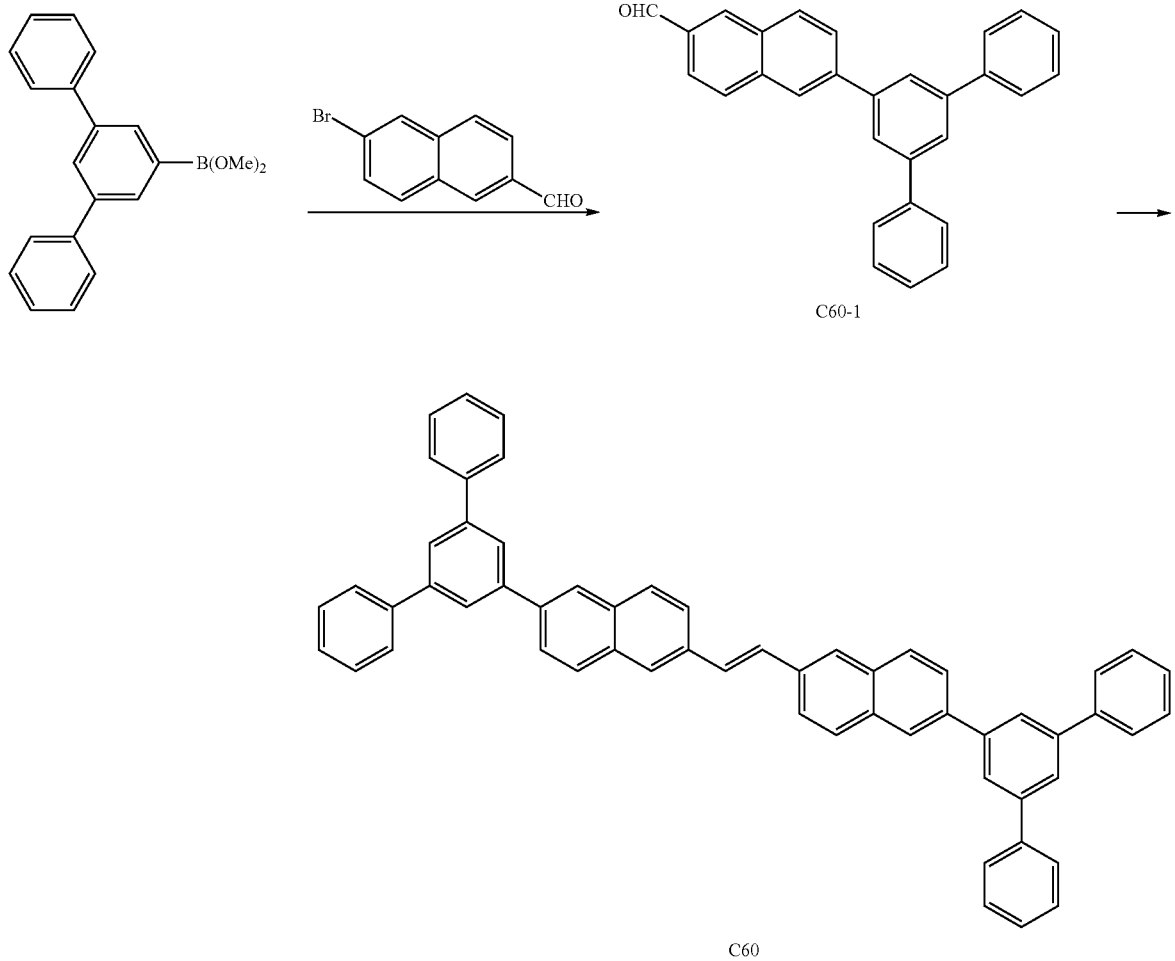

Synthesis of Intermediate C60-1

The process was the same as that for C53-1 (example 6), except that 3,5-diphenyl phenyl boronic acid was used instead of 4-biphenyl boronic acid, to afford a light yellow powder C60-1 (2.6 g).

Synthesis of Compound C60

The process was the same as that for C53, except that C60-1 was used instead of C53-1, to afford a yellow solid C60 (1.8 g).

MS (m/e) of compound C: 736;
Elemental analysis ($C_{58}H_{40}$): Calculated C: 94.53%, H: 5.47%; Found C: 94.50%, H: 5.44%.

Example 9

Synthesis of Compound C67

Synthesis scheme:

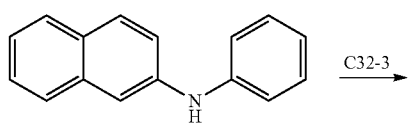

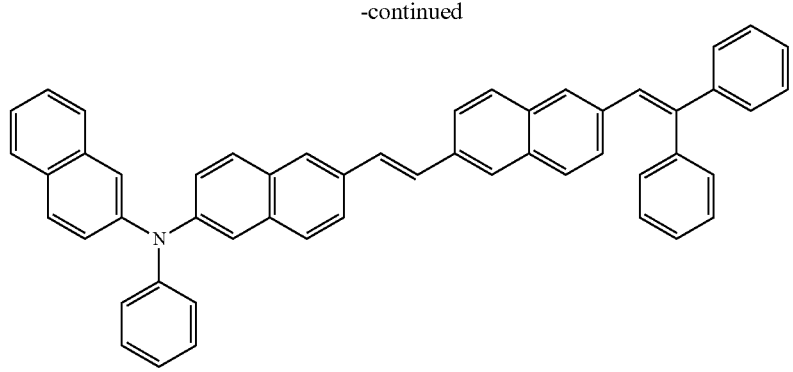
C67
The process was the same as that for C32 (example 4), to afford a yellow solid C67 (3.3 g).
| | |
|---|---|
| MS (m/e) of compound C: | 675; |
| Elemental analysis ($C_{52}H_{37}N$): | Calculated C: 92.41%, H: 5.52%, N: 2.07%; Found C: 92.45%, H: 5.50%, N: 2.00%. |
Example 10
Synthesis of Compound C68
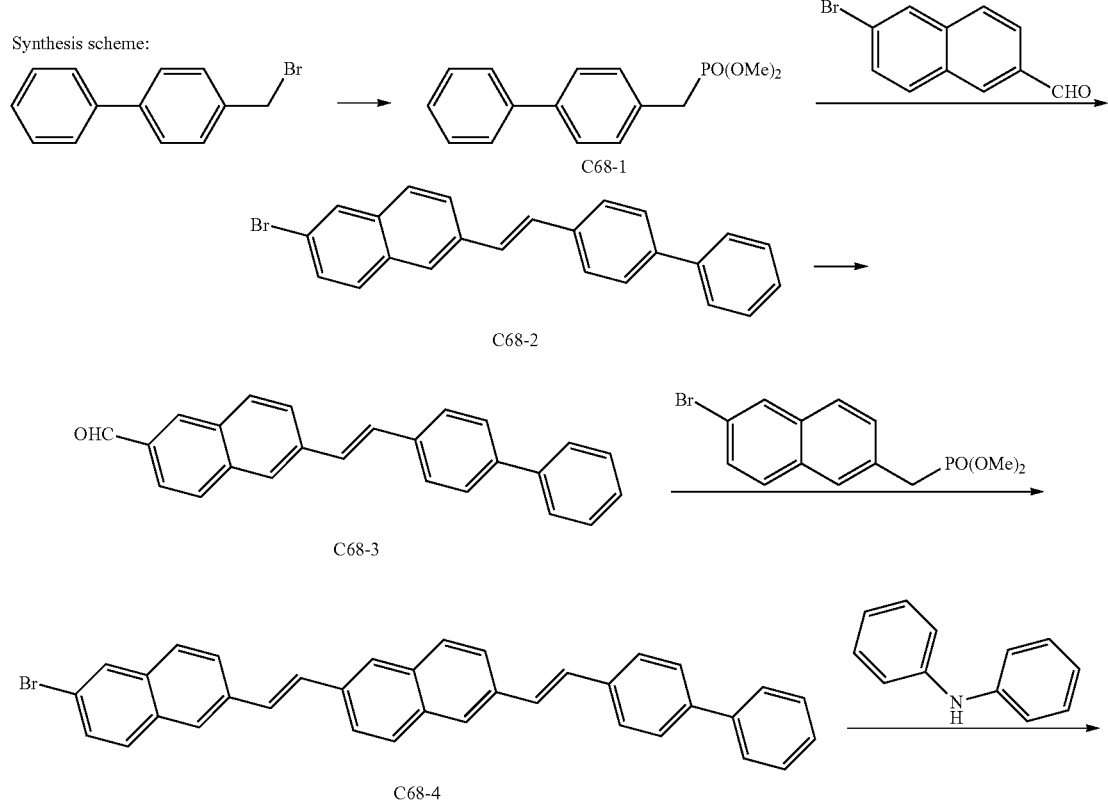

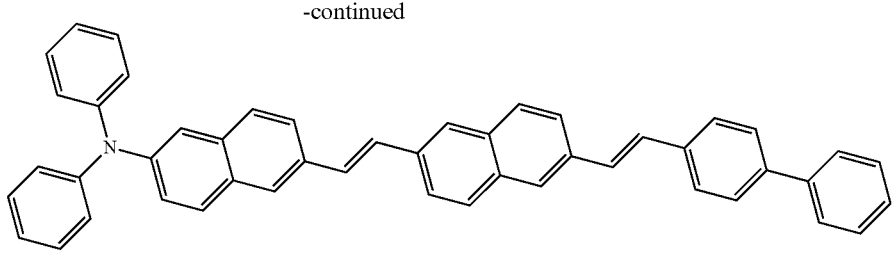

C68

Synthesis of Intermediate C68-1

The process was the same as that for dimethyl (6-bromonaphthalen-2-yl)methylphosphonate, except that 4-bromomehtyl biphenyl was used instead of 2-bromo-6-(bromomethyl)naphthalene, to afford a white solid C68-1 (4.6 g).

Synthesis of Intermediate C68-2

The process was the same as that for C34-1 (example 5), except that C68-1 and 6-bromo-2-naphthaldehyde was used instead of benzophenone and dimethyl (6-bromonaphthalen-2-yl)methylphosphonate respectively, to afford a white solid C68-2 (4.2 g).

Synthesis of Intermediate C68-3

The process was the same as that for C34-2 (example 5), except that C68-2 was used instead of C34-1, to afford a light yellow solid C68-3 (2.2 g).

Synthesis of Intermediate C68-4

The process was the same as that for C34-3 (example 5), except that C68-3 was used instead of C34-2, to afford a light yellow solid C68-4 (2.5 g).

Synthesis of Compound C68

The process was the same as that for C32 (example 4), except that diphenyl amine and C68-4 was used instead of 2-naphthalphenylamine and C32-4 respectively, to afford a yellow solid C68 (2.3 g).

| | |
|---|---|
| MS (m/e) of compound C: | 625; |
| Elemental analysis ($C_{48}H_{35}N$): | Calculated C: 92.12%, H: 5.64%, N: 2.24%; Found C: 92.10%, H: 5.60%, N: 2.22%. |

Example 11

Synthesis of Compound C75

Synthesis scheme:

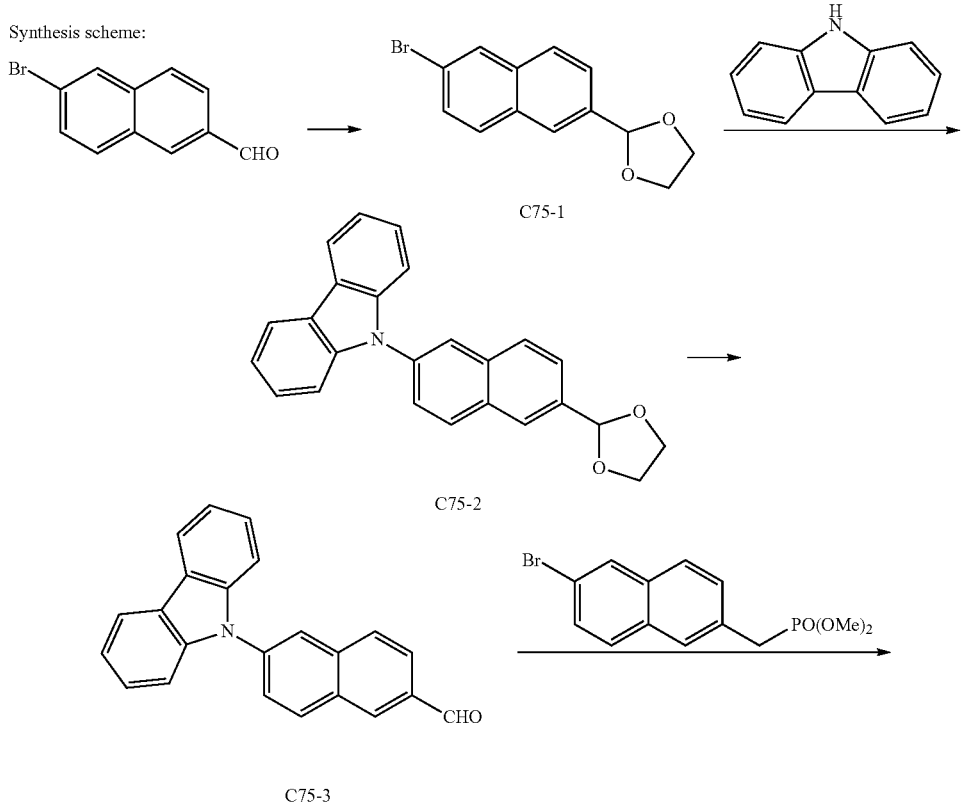

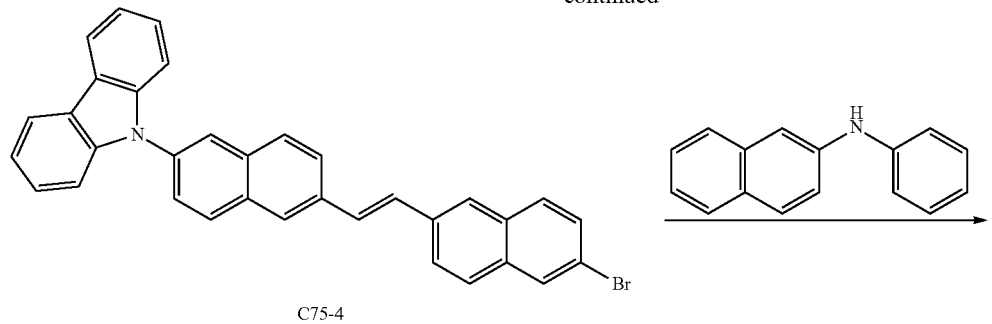

C75-4

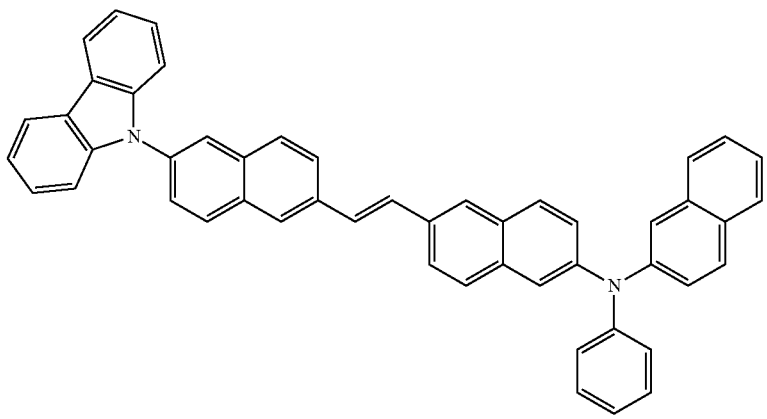

C75

Synthesis of Intermediate 75-1

To a three-necked flask (100 ml) was added 6-bromo-2-naphthaldehyde (20.0 g, 0.085 mol), glycol (40 ml, 0.715 mol), iodine (0.24 g, 0.9 mmol) and toluene (20 ml) under a flow of nitrogen with magnetic stirring. The mixture was heated to reflux. After 6 hours, to the mixture, anhydrous sodium carbonate (21.2 g, 0.2 mol) was added, and then the resulting mixture was kept under reflux overnight. The mixture was cooled to room temperature and poured into deionized water (200 ml), filtered under reduced pressure. The filter cake was recrystallized from chloroform, and the crystal was dried in vacuum to afford a yellow solid 75-1 (16.8 g).

Synthesis of Intermediates C75-2 and C75-3

To a three-necked flask (100 ml) was added 75-1 (4.17 g, 0.015 mol), carbazole (2.76 g, 0.016 mol), cuprous iodide (2.86 g, 0.016 mol), anhydrous potassium carbonate (4.17 g, 0.030 mol), 18-Crown-6 (0.08 g, 0.002 mol) and DMPU (45 ml) under a flow of argon. The mixture was heated under reflux for 4 hours. The mixture was cooled and kept under continued stirring overnight at room temperature. Deionized water (50 ml) was added to it, and the resulting solid was filtered out under reduced pressure. The filter cake was washed with deionized water, and then dissolved in acetone; the resulting mixture was filtered through a short silica gel column, eluted with acetone. The filtrate was concentrated and an equal volume of hydrochloric acid (15%) was added to it. The resulting mixture was then kept under continued stirring for 8 hours at room temperature. The precipitate was filtered under reduced pressure and recrystallized from ethyl acetate to afford a light yellow solid C75-3 (1.9 g).

Synthesis of Intermediate C75-4

The process was the same as that for C34-3 (example 5), except that C75-3 was used instead of C34-2, to afford a light yellow solid C75-4 (2.36 g).

Synthesis of Compound C75

The process was the same as that for C32 (example 4), except that C75-4 was used instead of C32-4, to afford yellow solid C75 (2.65 g).

| | |
|---|---|
| MS (m/e) of compound C: | 662; |
| Elemental analysis ($C_{50}H_{34}N_2$): | Calculated C: 90.60%, H: 5.17%, N: 2.23%; Found C: 90.59%, H: 5.20%, N: 2.20%. |

Example 12
Synthesis of Compound C80
Synthesis scheme:
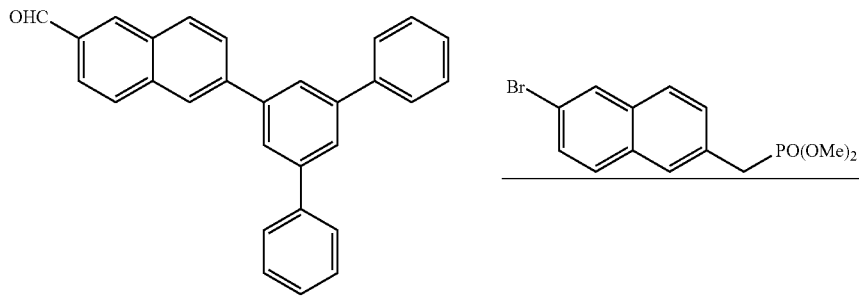
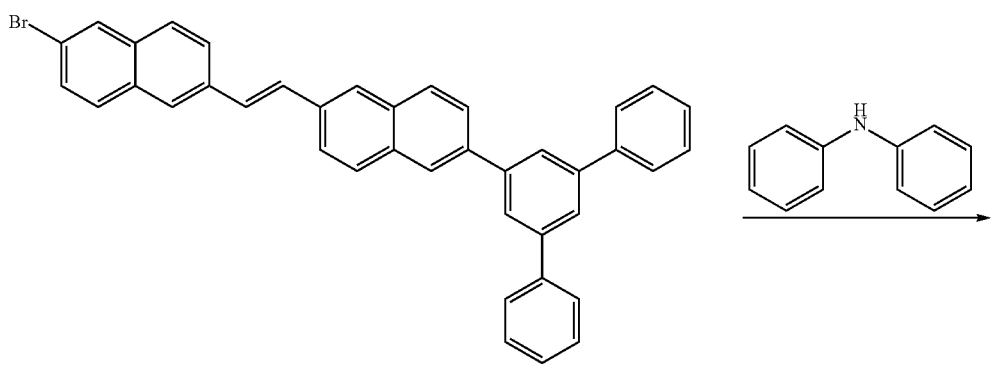
C80-1
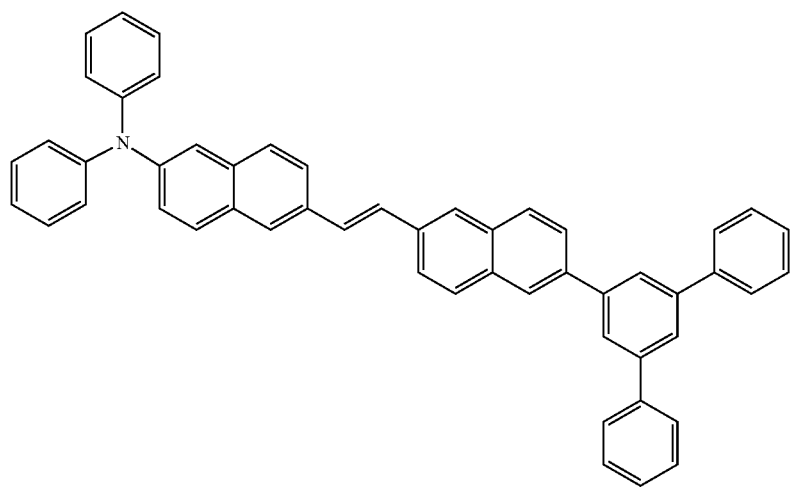
C80
Synthesis of Intermediate C80-1
The process was the same as that for C34-3 (example 5), except that C60-1 was used instead of C34-2, to afford a yellow solid C80-1 (2.55 g).
Synthesis of Compound C80
The process was the same as that for C68 (example 10), except that C80-1 was used instead of C68-4, to afford a yellow solid C80 (2.34 g).

| | |
|---|---|
| MS (m/e) of compound C: | 675; |
| Elemental analysis ($C_{52}H_{37}N$): | Calculated C: 92.41%, H: 5.52%, N: 2.07%;<br>Found C: 92.40%, H: 5.55%, N: 2.07%. |

Example 13

Synthesis of Compound C81

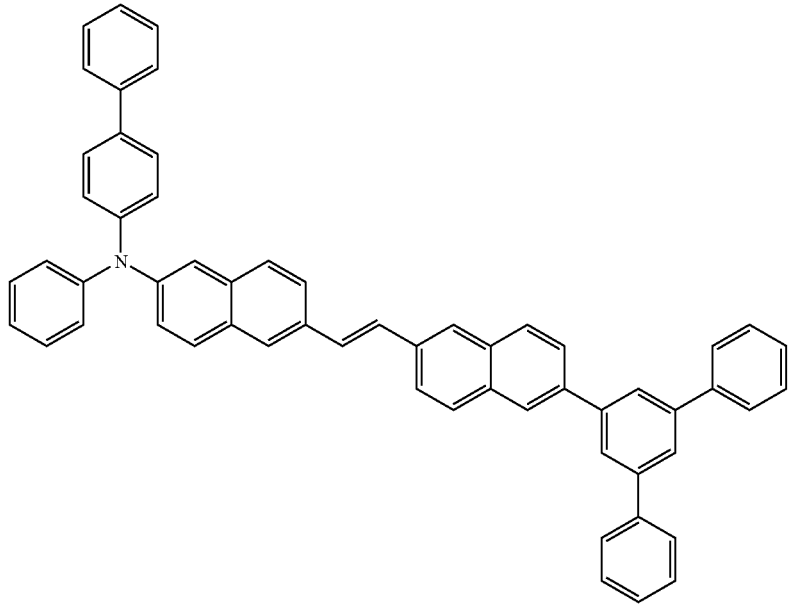

C81

The process was the same as that for the C80 (example 12), except that 4-biphenyl aniline was used instead of diphenylamine, to afford a yellow solid C81 (1.6 g).

| | |
|---|---|
| MS (m/e) of compound C: | 751; |
| Elemental analysis ($C_{58}H_{41}N$): | Calculated C: 92.64%, H: 5.50%, N: 1.86%;<br>Found C: 92.66%, H: 5.50%, N: 1.90%. |

Example 14

Synthesis of Compound C82

Synthesis scheme:

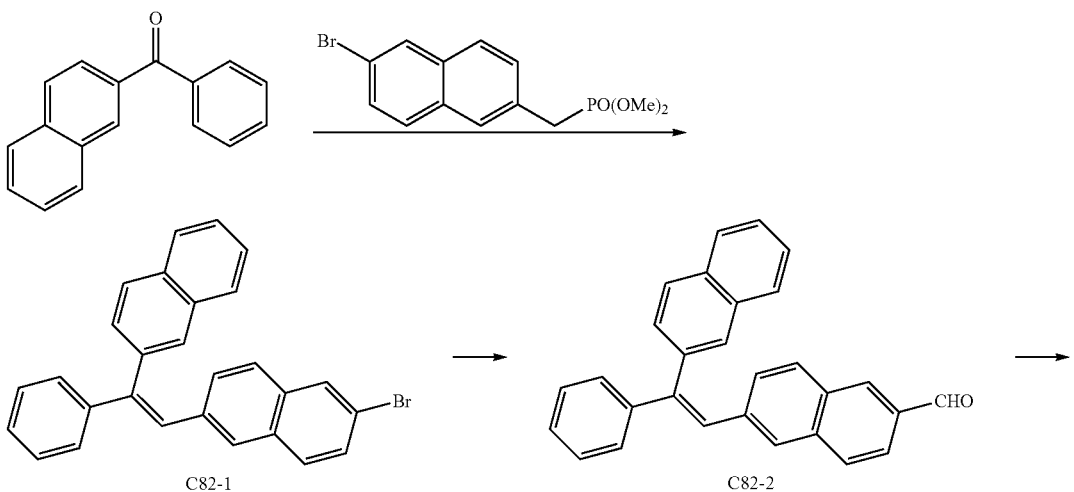

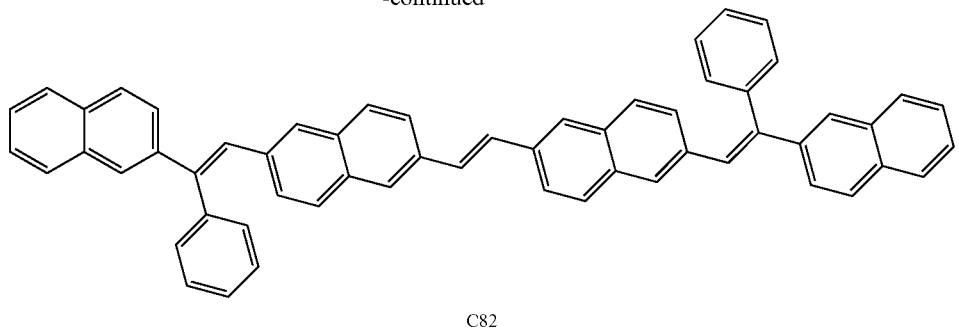

C82

Synthesis of Intermediate C82-1

The process was the same as that for C34-1 (example 5), except that 1-benzoyl naphthalene was used instead of benzophenone, to afford a white solid C82-1 (9.7 g).

Synthesis of Intermediate C82-2

The process was the same as that for C34-2 (example 5), except that C82-1 was used instead of C34-1, to afford a yellow solid C82-2 (4.28 g).

Synthesis of Compound C82

The process was the same as that for the C53 (example 6), except that C82-2 was used instead of C53-1, to afford a yellow solid C82 (5.6 g).

| | |
|---|---|
| MS (m/e) of compound C: | 736; |
| Elemental analysis ($C_{58}H_{40}$): | Calculated C: 94.53%, H: 5.47%; Found C: 94.51%, H: 5.44%. |

Example 15

Synthesis of Compound C98

Synthesis scheme:

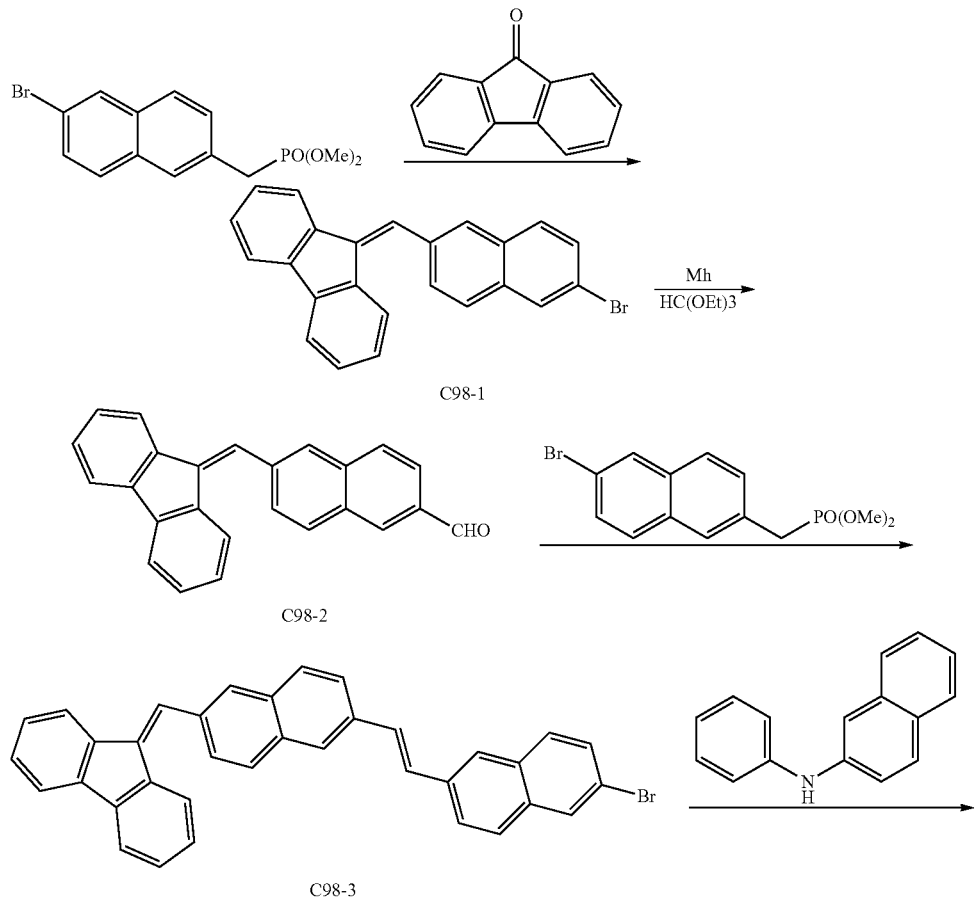

-continued

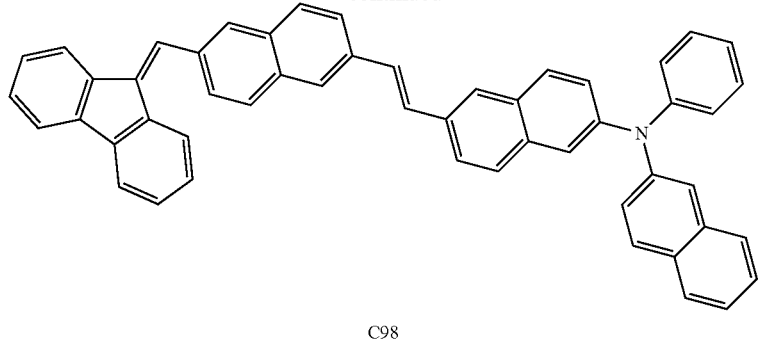

C98

Synthesis of Intermediate C98-1

The process was the same as that for C34-1 (example 5), except that fluorenone was used instead of benzophenone, to afford a yellow solid C98-1 (8.5 g).

Synthesis of Intermediate C98-2

To a dry three-necked flask (250 ml) was added anhydrous THF (20 ml), magnesium turnings (0.72 g, 0.030 mol) and a small amount of iodine under a flow of argon with magnetic stirring. The reaction was initiated by warming; the solution of C98-1 (5.74 g, 0.015 mol) dissolved in anhydrous THF (100 ml) was added to the reaction mixture and then the reaction mixture was heated to reflux for 20 hours. After the additions are completed, but while the reaction is still in progress, the Grignard reagent begins to precipitate on the walls of the flask. A dry, thiophene-free benzene (10 ml) is added from the Pyrex separatory funnel at such a rate as to keep the Grignard reagent in solution. After the refluxing due to the exothermic reaction stopped, the mixture was heated under mild reflux with stirring for 4 hours.

The mixture was allowed to cool until refluxing ceased. Then, to the mixture, triethyl orthoformate (2.22 g, 0.015 mol) was added dropwise over 5 minutes, and then the resulting mixture was heated up to reflux for 6 hours. When the mixture was cooled with an ice-bath, cool hydrochloric acid (10%, 7.5 ml) was added dropwise slowly. The organic layer was separated and concentrated under reduced pressure. To the residue, sulphuric acid solution (25%, 7.5 ml) was added and the resulting mixture was heated to reflux for 12 hours.

The mixture is then cooled in an ice bath. The acid is decanted, and the residue is washed twice with water. The residue is dissolved in benzene (7.5 ml) in the same flask, and to the resulting mixture, water (11 ml) and sodium bisulfite (9 g) were added. The mixture was stirred vigorously overnight.

The mixture was filtered, and the filter cake was washed on the Büchner funnel with benzene (5 ml).

The filter cake was broken up and returned to the same flask (50 ml). A saturated solution of sodium bicarbonate was added slowly with stirring until there was no further sign of decomposition of any compound. The mixture was stirred for additional 2 hours. The solution was made alkaline throughout by adding sodium bicarbonate if necessary. The crude aldehyde was collected by filtering under reduced pressure and the filter cake was washed with water, and allowed to dry. The crude aldehyde was recrystallized from ethyl acetate-anhydrous ethanol to afford a light yellow solid C98-2 (2.0 g).

Synthesis of Intermediate C98-3

The process was the same as that for C32-4 (example 4), except that C98-2 was used instead of C32-3, to afford a yellow solid C98-3 (2.75 g).

Synthesis of Compound C98

The process was the same as that for C32 (example 4), except that C98-3 was used instead of C32-4, to afford a yellow solid C98 (4.23 g).

MS (m/e) of compound C: 673;
Elemental analysis (C$_{52}$H$_{35}$N): Calculated C: 92.69%, H: 5.24%, N: 2.08%; Found C: 92.66%, H: 5.18%, N: 2.08%.

Example 16

Synthesis of Compound C101

Synthesis scheme:

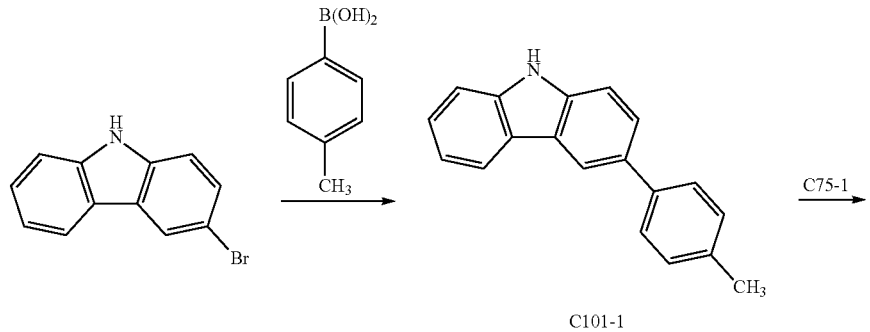

C101-1

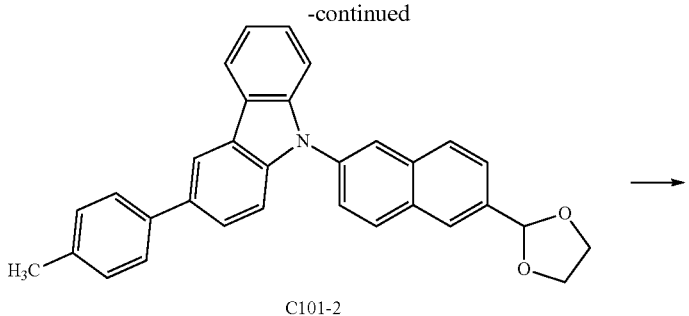

C101-2

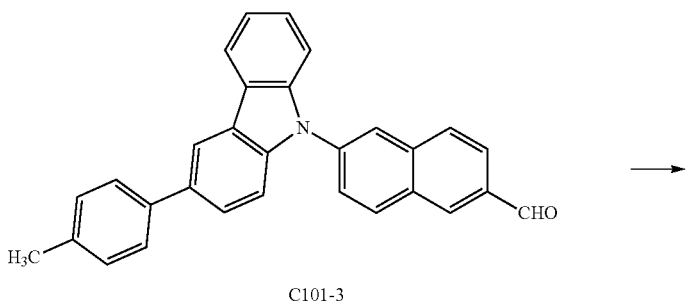

C101-3

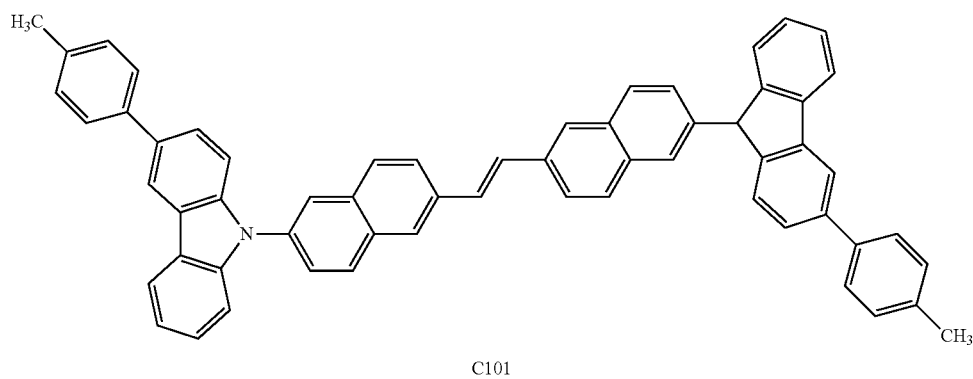

C101

Synthesis of Intermediate C101-1

The process was the same as that for C1-1 (example 1), except that 3-bromocabazole and 4-methylphenyl boronic acid was used instead of 2-bromothiophene and phenyl boronic acid, to afford a white solid C101-1 (3.7 g).

Synthesis of Intermediates C101-2 and C101-3

The process was the same as that for C75-2 and C75-3 (example 11), except that C101-1 was used instead of carbazole, to afford a light yellow solid C101-3 (1.77 g).

Synthesis of Compound C101

The process was the same as that for C60 (example 8), except that C101-3 was used instead of C60-1, to afford a yellow solid C101 (2.98 g).

| | |
|---|---|
| MS (m/e) of compound C: | 790; |
| Elemental analysis ($C_{60}H_{42}N_2$): | Calculated C: 91.11%, H: 5.35%, N: 3.54%; Found C: 91.10%, H: 5.35%, N: 3.54%. |

Example 17

Synthesis of Compound C103

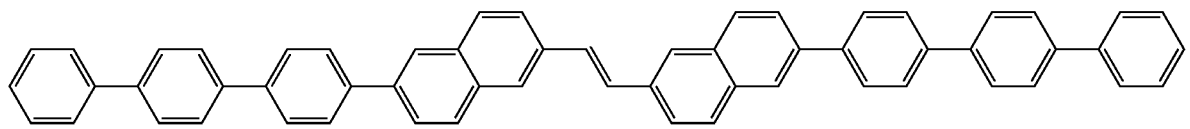

C103

The process was the same as example 6, except that 4-(4'-biphenyl)phenyl boronic acid was used instead of 4-biphenylboronic acid, to afford a light yellow solid C103 (1.6 g).

| | |
|---|---|
| MS (m/e) of compound C: | 736; |
| Elemental analysis ($C_{58}H_{40}$): | Calculated C: 94.53%, H: 5.47%; Found C: 94.42%, H: 5.57%. |

Example 18

Synthesis of Compound C107

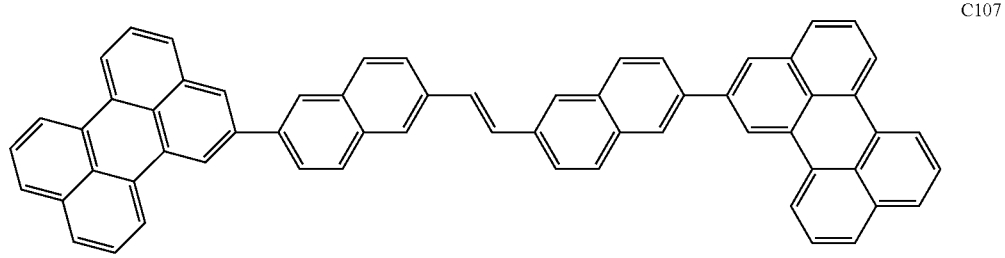 [SMILES: C(=C\c1ccc2cc(-c3cc4cccc5c6cccc7cccc(c(c3)c45)c76)ccc2c1)/c1ccc2cc(-c3cc4cccc5c6cccc7cccc(c(c3)c45)c76)ccc2c1]

The process was the same as example 6, except that perylen-2-yl boronic acid was used instead of 4-biphenyl boronic acid, to afford a yellow solid C107 (1.10 g).

| | |
|---|---|
| MS (m/e) of compound C: | 780; |
| Elemental analysis ($C_{62}H_{36}$): | Calculated C: 95.35%, H: 4.65%; Found C: C: 95.32%, H: 4.60%. |

Example 19

Synthesis of Compound C113

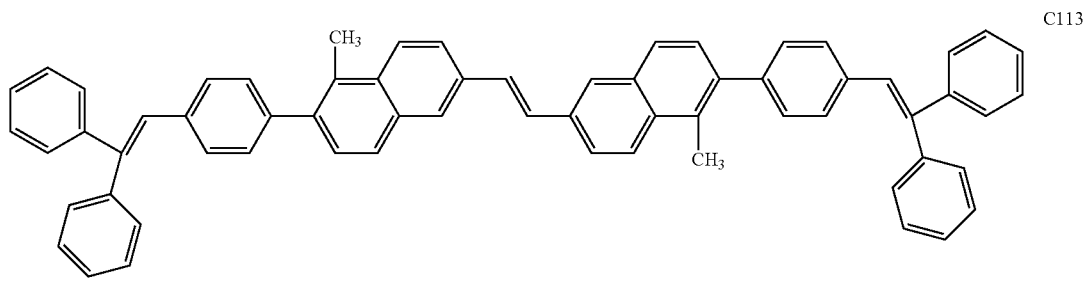 [SMILES: Cc1c(-c2ccc(C=C(c3ccccc3)c3ccccc3)cc2)ccc2cc(/C=C/c3ccc4c(C)c(-c5ccc(C=C(c6ccccc6)c6ccccc6)cc5)ccc4c3)ccc12]

The process was the same as example 6, except that 4-(2',2'-diphenylvinyl)phenyl boronic acid and 6-bromo-5-methyl-2-naphthaldehyde were used instead of 4-biphenyl boronic acid and 6-bromo-2-naphthaldehyde, to afford a yellow solid C113 (1.8 g).

| | |
|---|---|
| MS (m/e) of compound C: | 816; |
| Elemental analysis ($C_{64}H_{48}$): | Calculated C: 94.08%, H: 5.92%; Found C: 94.10%, H: 5.92%. |

Example 20
Synthesis of Compound C116

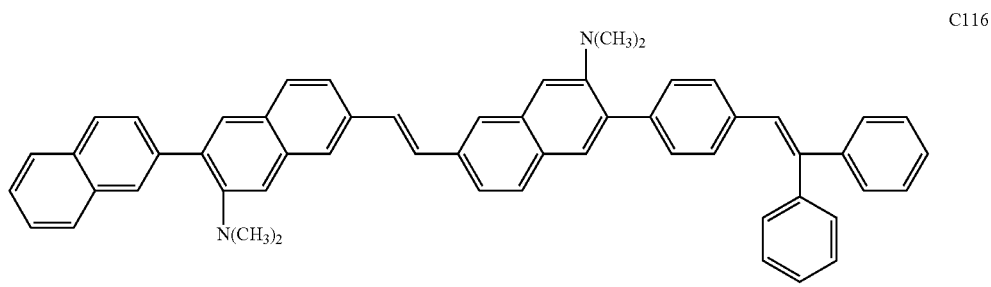 [SMILES: CN(C)c1cc2cc(/C=C/c3ccc4cc(-c5ccc6ccccc6c5)c(N(C)C)cc4c3)ccc2cc1-c1ccc(C=C(c2ccccc2)c2ccccc2)cc1]

The process was the same as example 19, except that naphthalen-2-yl boronic acid, 6-bromo-7-(N,N-dimethylamino)-2-methylnaphthalene, and 6-bromo-7-(N,N-dimethylamino)-2-naphthaldehyde were used instead of 4-(2',2'-diphenylvinyl)phenyl boronic acid, 6-bromo-2-methylnaphthalene and 6-bromo-2-naphthaldehyde, to afford a yellow solid C116 (1.2 g).

| | |
|---|---|
| MS (m/e) of compound C: | 746; |
| Elemental analysis ($C_{56}H_{46}N_2$): | Calculated C: 90.04%, H: 6.21%, N: 3.75%; Found C: 90.00%, H: 6.21%, N: 3.74%. |

Example 21
Synthesis of Compound C120

Synthesis scheme:

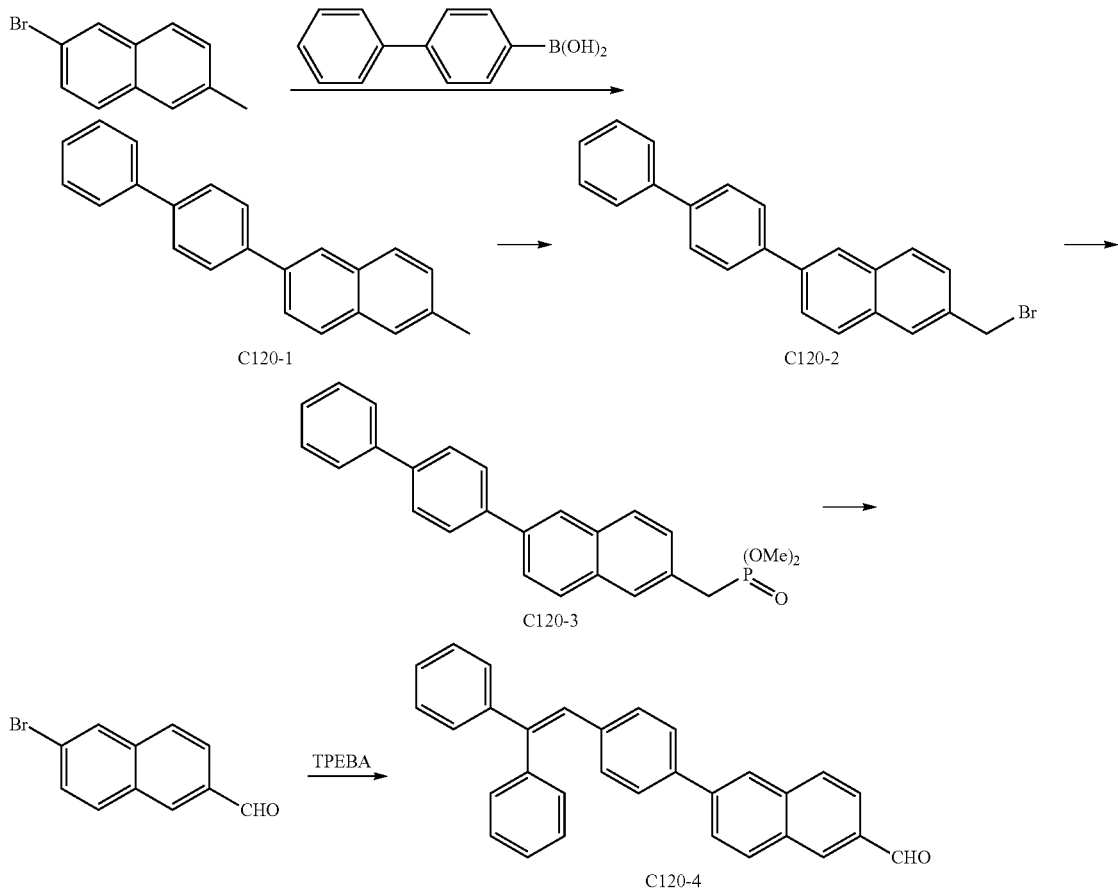

C120-3
+
C120-4

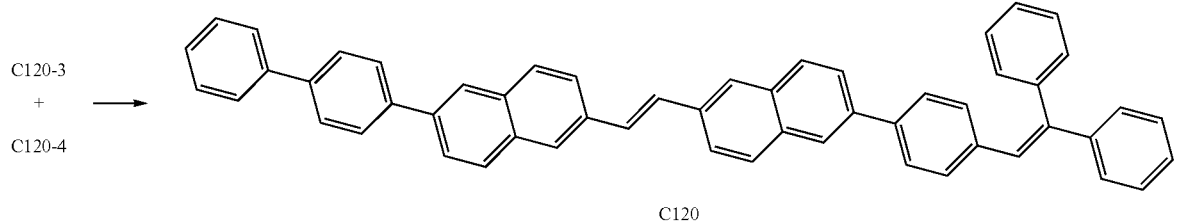

C120

Synthesis of Intermediate C120-1

The process was the same as that for C53-1 (example 6), except that 6-bromo-2-methylnaphthalene was used instead of 6-bromo-2-naphthaldehyde, to afford a light yellow solid powder C120-1 (48 g).

Synthesis of Intermediate C120-2

To a three-necked flask (1000 ml) were added C120-1 (29.4 g, 0.1 mol) and anhydrous THF (400 ml) with magnetic stirring. To this mixture was added a solution of N-bromosuccinimide (17.8 g) dissolved in anhydrous THF (100 ml) dropwise. The resulting mixture was kept under continued stirring 12 hours at room temperature. The mixture was poured into a saturated solution of sodium bicarbonate (300 ml), and extracted with ethyl acetate (200 ml×3). The combined organic layers was washed with deionized water until the washing water was neutral, and dried over anhydrous magnesium sulphate. The organic layer was filtered and the solvent was removed to afford a white solid C120-2 (24.5 g).

Synthesis of Intermediate C120-3

The process was the same as that for dimethyl (6-bromonaphthalen-2-yl)methylphosphonate, to afford a white solid C120-3 (38.6 g).

Synthesis of Intermediate C120-4

The process was the same as that for C12-3 (example 2), except that 4-(2',2'-diphenylvinyl)phenyl boronic acid was used instead of C12-2, to afford a light yellow powder C120-4 (64 g).

Synthesis of Compound C120

The process was the same as that for C32-4 (example 4), except that C120-3 and C120-4 were used instead of dimethyl (6-bromonaphthalen-2-yl)methylphosphonate and C32-3, to afford a yellow powder C120 (2 g).

| MS (m/e) of compound C: | 686; |
|---|---|
| Elemental analysis ($C_{54}H_{38}$): | Calculated C: 94.42%, H: 5.58%; Found C: 94.38%, H: 5.57%. |

Example 22

Synthesis of Compound C128

Synthesis scheme:

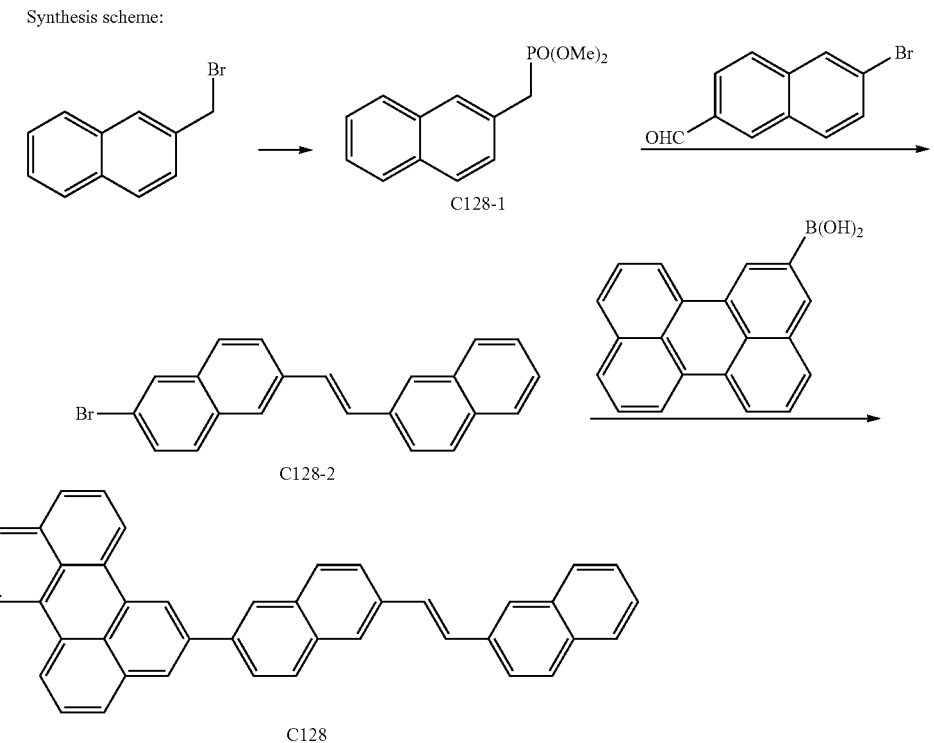

Synthesis of Intermediate C128-1

The process was the same as that for C120-3 (example 21), except that 2-bromomethyl naphthalene was used instead of C120-2, to afford a white solid C128-1 (2.9 g).

Synthesis of Intermediate C128-2

The process was the same as that for C68-2 (example 10), except that C128-1 was used instead of C68-1, to afford a white solid C128-2 (2.69 g).

Synthesis of Compound C128

The process was the same as that for C1-1 (example 1), except that perylen-2-yl boronic acid and C128-2 were used instead of phenyl boronic acid and 2-bromothiophene, to afford a yellow solid C128 (2.38 g).

| | |
|---|---|
| MS (m/e) of compound C: | 530; |
| Elemental analysis ($C_{42}H_{26}$): | Calculated C: 95.06%, H: 4.94%; Found C: 95.05%, H: 4.90%. |

Example 23

Synthesis of Compound C129

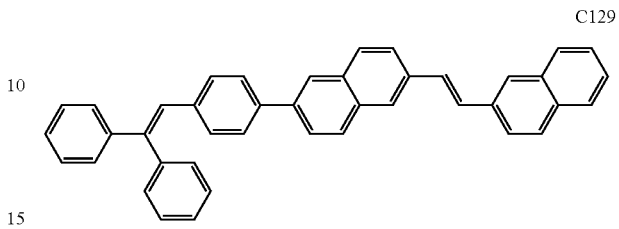

The process was the same as that for C128 (example 22), except that 4-(2',2'-diphenylvinyl)phenylboronic acid was used instead of perylen-2-yl boronic acid, to afford a yellow solid C129 (1.73 g).

MS (m/e) of compound C: 534:

Elemental analysis ($C_{42}H_{30}$): Calculated C, 94.34%; H, 5.66%;

Found C, 94.35%; H, 5.60%.

Example 24

Synthesis of Compound C132

Synthesis scheme:

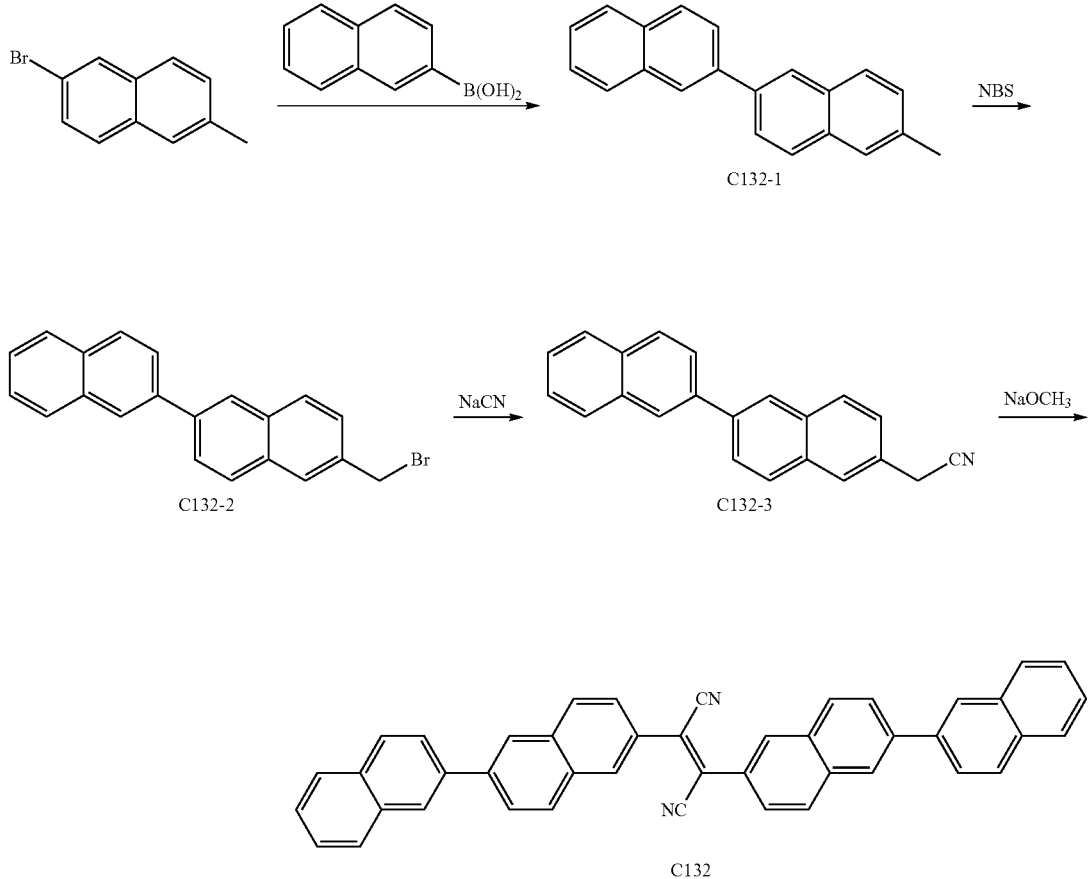

Synthesis of Intermediate C132-1

The process was the same as that for C120-1 (example 21), except that naphthalen-2-ylboronic acid was used instead of 4-biphenylboronic acid, to afford a white solid powder C132-1 (4.0 g).

Synthesis of Intermediate C132-2

The process was the same as that for C120-2 (example 21), except that C132-1 was used instead of C120-1, to afford a white solid C132-2 (2.1 g).

Synthesis of Intermediate C132-3

To a three-necked flask (100 ml) were added sodium cyanide (0.98 g, 0.176 mol), and N'N'-dimethyl formamide (DMSO, 20 ml) with magnetic stirring under nitrogen. The mixture was heated up to 90□ for 1 hour. To the mixture was added a solution of C132-2 (3.46 g, 0.010 mol) in DMSO (20 ml) dropwise slowly without exceeding 160□. Then, the mixture continued to be heated under reflux for 1 hour. The mixture was cooled to room temperature, and to it was added deionized water (50 ml). the mixture was extracted with chloroform (50 ml×2). The combined organic layer was washed with saturated sodium chloride (30 ml) solution, dried over anhydrous magnesium sulphate, and filtered; the solvent was then removed from the filtrate by a Rotary Evaporator to afford a white solid C132-3 (1.51 g).

Synthesis of Compound C132

To a three-necked flask (100 ml) were added C132-3 (2.93 g, 0.010 mol), iodine (1.27 g, 0.01 mol), and ethylene glycol diethyl ether (30 ml). The mixture was cooled to -78□ in an ethanol-liquid nitrogen bath with magnetic stirring. To the mixture was added a solution of sodium methoxide (1.08 g) in methanol (20 ml) dropwise slowly and the temperature was kept at -78□ for 1 hour. The cooling bath was removed and the temperature rose up to 0□. After 4 hours at 0□, the mixture was neutralized (until PH=7) with hydrochloric acid (3%). The mixture was then filtered under reduced pressure and the filter cake was washed with deionized water (10 ml) and then was dried to afford a light yellow solid C132 (2.61 g).

| | |
|---|---|
| MS (m/e) of compound C: | 582; |
| Elemental analysis ($C_{44}H_{26}N_2$): | Calculated C: 90.69%, H: 4.50%, N: 4.81%; Found C: 90.70%, H: 4.50%, N: 4.80%. |

Example 25

Synthesis of Compound C133

Synthesis scheme:

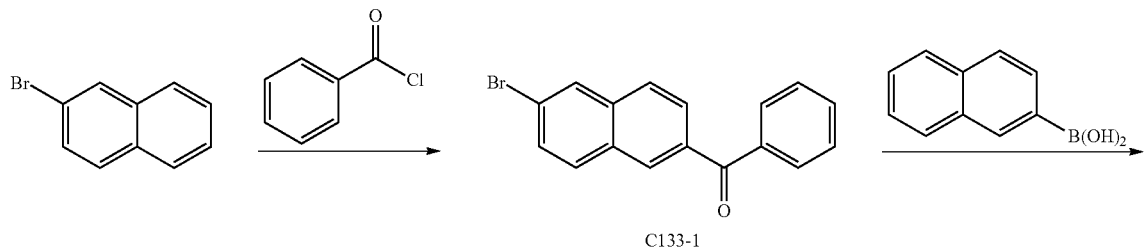

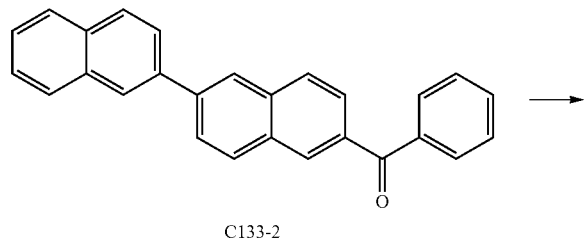

C133-2

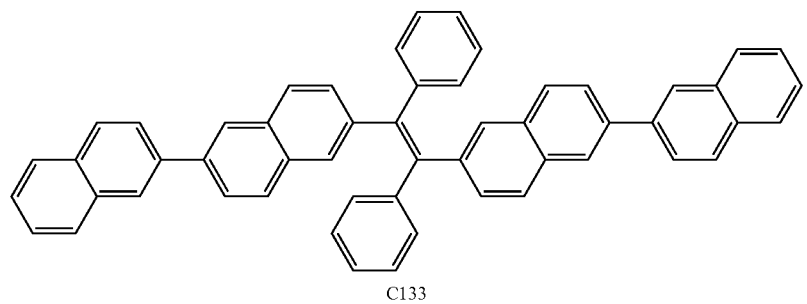

C133

Synthesis of Intermediate C133-1

To a three-necked flask (250 ml) were added anhydrous aluminum trichloride (19.8 g, 0.148 mol) and 1,2-dichloroethane (50 ml) with magnetic stirring under nitrogen. The suspension was cooled below −10☐ and benzoyl chloride (14 g, 0.010 mol) was added dropwise slowly to it at this temperature. After 1 hour at this temperature, a solution of 2-bromonaphthanlene (20.7 g) dissolved in 1,2-dichloroethane (100 ml) was added. The mixture was kept under continued stirring for 2 hours at room temperature, then poured into ice-water mixture (300 g) and neutralized (PH=5) with hydrochloric acid. The mixture was extracted with dichloromethane (50 ml×2) and the combined organic layer was wash with saturated sodium chloride solution, dried over anhydrous magnesium sulphate, filtered. The solvent was then removed from the filtrate by a Rotary Evaporator to afford a yellow solid C133-1 (24.1 g).

Synthesis of Intermediate C133-2

The process was the same as that for C132-1 (example 24), except that C133-1 was used instead of 6-bromo-2-methylnaphthalene, to afford a white solid C133-2 (2 g).

Synthesis of Compound C133

The process was the same as that for C1 (example 1), except that C133-2 was used instead of C1-3, to afford a yellow powder C133 (0.71 g).

| | |
|---|---|
| MS (m/e) of compound C: | 684; |
| Elemental analysis ($C_{54}H_{36}$): | Calculated C: 94.70%, H: 5.30%; Found C: 94.90%, H: 5.10%. |

USE EXAMPLES

Organic Light Emitting Devices Containing the Compounds of the Present Invention The following processes are preferred for making the OLED of the present invention:

The typical structure of the OLED is: substrate/anode/hole transporting layer (HTL)/organic luminescence layer charge transporting layer (ETL)/cathode.

The substrate is transparent and can be attached to a glass or flexible substrate. The flexible substrate can be polyester, such as polyimide. Material used in anode can be inorganic materials, such as metal oxide, including tin indium oxide (ITO), zinc oxides, tin oxides, ect., or metals, such as auru, silver and copper, which have high power function. ITO is most preferred. Material used in anode also can be organic conductive polymer, with polythiophene/Poly(3,4-ethylenedioxythiophene) poly(styrenesulfonate) (PEDOT:PSS) or polyaniline (PANI) being preferred. In general, metal which has a low power function, such as lithium, magnesium, calcium, strontium, aluminum, indium or their alloy auru, silver and copper, or an electrode layer formed by alternate layers of metal and metal fluoride, can be used as cathode material. Alloy of magnesium and silver, silver, LiF, and aluminum are preferred. Triarylamine materials are used in hole transporting layer, with N,N'-Di(naphthalen-1-yl)-N,N'-diphenyl-benzidine (NPB) being preferred. In charge transporting layer may be used metal complexes, such as tris-(8-hydroxyquinolinato)aluminum ($Alq_3$), tris-(8-hydroxyquinolinato)gallium ($Gaq_3$), (salicylidene-o-aminophenolato) (8-quinolinoato) gallium [Ga(Saph-q)], or derivates of phenathroline such as 4,7-diphenyl-1,10-phenanthroline (Bphen), ect. Small molecule organic material can be used in organic luminescent layer, where fluorescence material or phosphorescence dyestuff can be use as a dopant. The materials used in the organic luminescent layer containing the compounds of the present invention, which is formed into a film. The film can be used singly as the luminescent layer, or can also be use as a dopant together with a corresponding host material, which preferably is $Alq_3$, $Gaq_3$ or Ga(Saph-q).

A series of organic light emitting devices (OLEDs) were made as follows:

(1) Firstly, the glass substrate was washed with, on a consecutive basis, a detergent, deionized water and an organic solvent;

(2) Secondly, the hole transporting material was heated to evaporate and deposited on the substrate as the hole transporting layer;

(3) Thirdly, a blue luminescent material of the present invention was heated to evaporate and deposited on the hole transporting layer as the emitting layer;

(4) Fourthly, a charge transporting layer was deposited over the luminescent layer;

(5) Lastly, metal cathode was formed on the charge transporting layer by vapor-depositing or sputtering, and thus a blue OLED was made.

Use Example 1

Making of Devices OLED-1 to OLED-3

Making of OLED-1:

A glass substrate coated with a conductive ITO layer was treated with a commercially available detergent with ultrasound wave and washed with deionized water. The oil was eliminated from the substrate by using a mixture of acetone-ethanol with ultrasound wave and the substrate was dried completely to eliminate deionized water under a clean condition, and then was subjected to a low energy cation beam bombardment directed to its surface.

The ITO substrate was mounted in a vapor-depositing machine. Pressure in the vapor-depositing machine was reduced to $1 \times 10^{-5}$ to $9 \times 10^{-3}$ Pa. NPB (N,N'-Di(naphthalen-1-yl)-N,N'-diphenyl-benzidine) in the first quartz crucible was heated to evaporate and deposited on the substrate as the hole transporting layer to a thickness of 55 nm at a rate of 0.1 nm/s. Then, compound of C55 of the present invention (see example 7) in the second quartz crucible and $Alq_3$ in the third quartz were heated to evaporate and deposited on the hole transporting layer to a total thickness of 30 nm to form the luminescent layer at a total rate of 0.1 nm/s, where the ratio between C55 and $Alq_3$ was 1:100. Further, An electron transporting layer made of $Alq_3$ was formed over the luminescent layer and had a 20 nm thickness at a rate of 0.1 nm/s. Lastly, an cathode membrane of Mg:Ag alloy of 100 nm thickness at a rate of 2.0-3.0 nm/s and then Ag of 100 nm thickness at a rate of 0.3 nm/s with 100 nm thickness were successively formed on the electron transporting layer to constitute OLED1.

The structure of the device made as above was:

ITO/NPB(50 nm)/BH04(40 nm):C[x %]/$Alq_3$(20 nm)/Mg:Ag(100 nm)/Ag(100 nm)

Wherein C is the luminescent material of the present invention and x % is the doping consistency of C.

OLED-2 and OLED-3 have the same structures and layer compositions as OLED-1, except for the weight of compound C55 of the present invention (based on the total weight of the luminescent layer) doped in Alq₃. The performance of OLED1-3 is shown in table 1:

TABLE 1

| | | Performance of OLED1-3 | | | |
|---|---|---|---|---|---|
| Device | X % | Luminescent Wavelength (nm) | Current Intensity (A/m²) | CIE (x, y) | Current Efficiency (cd/A) |
| OLED-1 | 7% | 440 | 592 | 0.16, 0.13 | 2.18 |
| OLED-2 | 10% | 444 | 579 | 0.16, 0.14 | 1.94 |
| OLED-3 | 20% | 444 | 617 | 0.16, 0.15 | 1.61 |

The results are also shown in FIG. 1.

Use Example 2

Devices OLED-4 to OLED-6

Use example 1 was repeated except that C67 (example 9) in the luminescent layer was used instead of C55.

The performance of the OLED4-6 is shown in table 2:

TABLE 2

| | | Performance of OLED4-6 | | | |
|---|---|---|---|---|---|
| Device | X % | Luminescent Wavelength (nm) | Current Intensity (A/m²) | CIE (x, y) | Current Efficiency (cd/A) |
| OLED-4 | 3% | 456 | 843 | 0.15, 0.16 | 2.91 |
| OLED-5 | 7% | 460 | 1006 | 0.15, 0.19 | 3.59 |
| OLED-6 | 11% | 462 | 1000 | 0.16, 0.20 | 3.41 |

Figure 2:
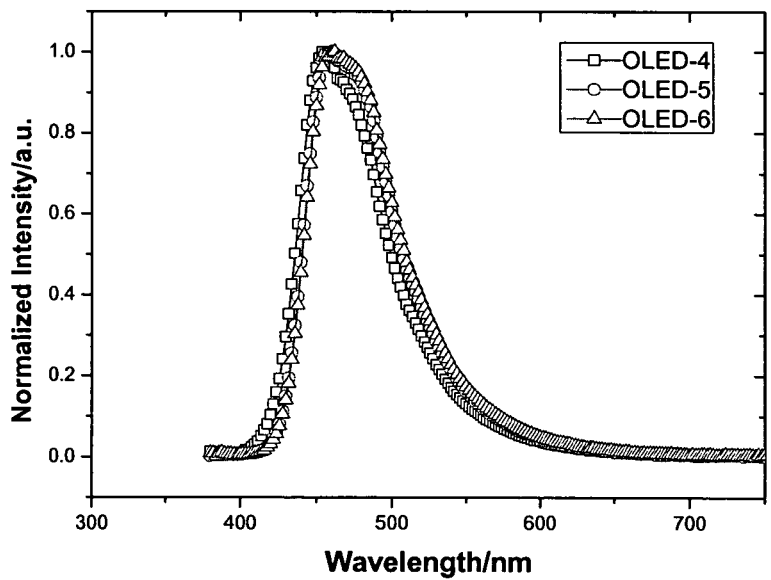
FIG. 2 shows the electroluminescence spectra of OLED-4 to OLED-6.

The results are also shown in FIG. 2.

Use Example 3

Devices OLED-7 to OLED-9

Use example 1 was repeated except that C82 (see example 14) in the luminescent layer was used instead of C55.

The performance of the OLED7-9 is shown in table 3:

TABLE 3

| | | Performance of OLED7-9 | | | |
|---|---|---|---|---|---|
| Device | X % | Luminescent Wavelength (nm) | Current Intensity (A/m²) | CIE (x, y) | Current Efficiency (cd/A) |
| OLED-7 | 3% | 466 | 982 | 0.17, 0.24 | 5.27 |
| OLED-8 | 7% | 470 | 987 | 0.16, 0.26 | 3.67 |
| OLED-9 | 11% | 468 | 1032 | 0.17, 0.29 | 4.51 |

Figure 3:
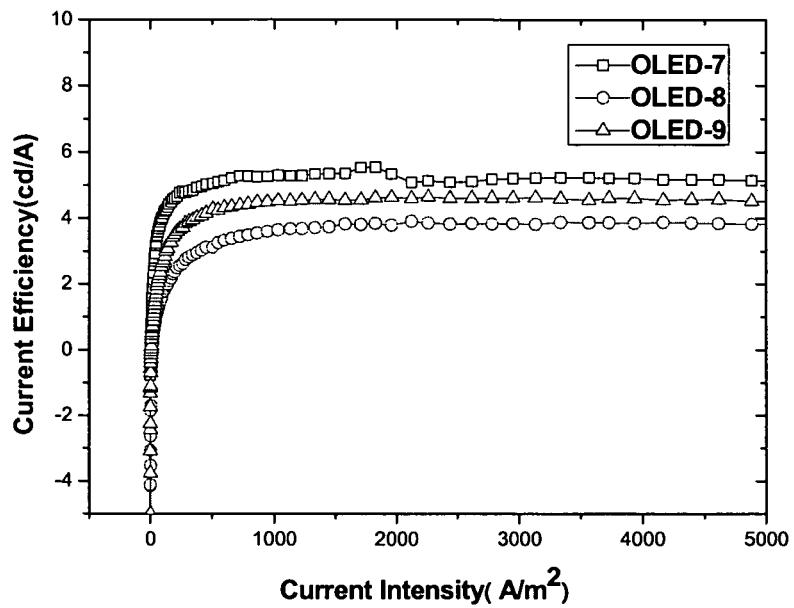
FIG. 3 shows the efficiency-current intensity curves of OLED-7 to OLED-9.

The results are also shown in FIG. 3.

Use Example 4

Devices OLED-10 to OLED-12

Use example 1 was repeated except that C133 (see example 25) in the luminescent layer was used instead of C55.

The performance of the OLED7-9 is shown in table 4:

TABLE 4

| | | Performance of OLED10-12 | | | |
|---|---|---|---|---|---|
| Device | X % | Emission Wavelength (nm) | Current Intensity (A/m²) | CIE (x, y) | Current Efficiency (cd/A) |
| OLED-10 | 3% | 460 | 425 | 0.14, 0.17 | 2.00 |
| OLED-11 | 7% | 468 | 425 | 0.14, 0.19 | 4.81 |
| OLED-12 | 11% | 468 | 425 | 0.14, 0.19 | 2.7 |

Figure 4:
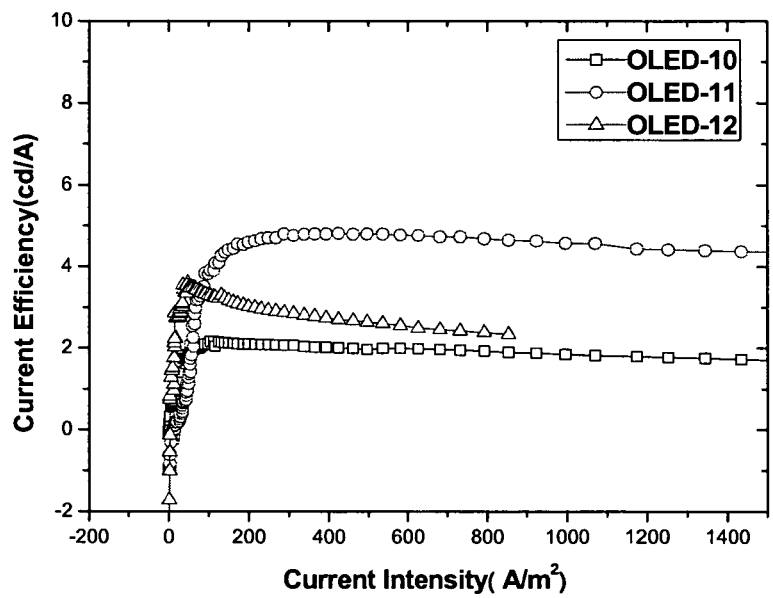
FIG. 4 shows efficiency-current intensity curves of OLED-10 to OLED-12.

The results are also shown in FIG. 4.

The invention has been described in detail with reference to certain preferred embodiments. However, variations and modifications can be effected within the spirit and scope of the invention.

What is claimed is:

1. A device comprising a cathode, an anode, and a layer disposed between the cathode and the anode comprising a compound represented by the formula:

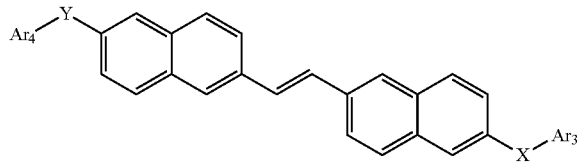

wherein X and Y are

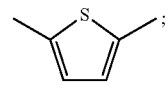

and wherein Ar₃ and Ar₄ are independently selected from the group consisting of

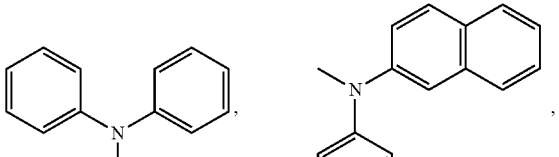

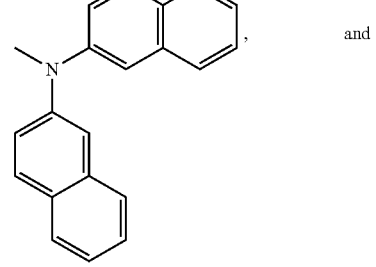

and

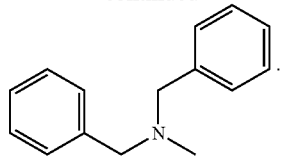
2. The device of claim 1, wherein the device is an OLED.
3. The device of claim 1, wherein the layer disposed between the cathode and the anode comprises
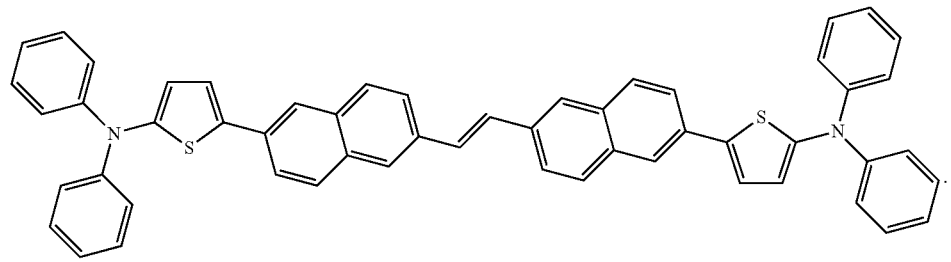 [SMILES: C(=C\c1ccc2cc(-c3ccc(N(c4ccccc4)c4ccccc4)s3)ccc2c1)/c1ccc2cc(-c3ccc(N(c4ccccc4)c4ccccc4)s3)ccc2c1]
4. The device of claim 1, wherein the device further comprises a substrate.
* * * * *